(12) United States Patent
Bachmann et al.

(10) Patent No.: US 11,324,836 B2
(45) Date of Patent: *May 10, 2022

(54) MODIFIED VIRUS-LIKE PARTICLES OF CMV

(71) Applicant: SAIBA AG, Rämismühle (CH)

(72) Inventors: Martin Bachmann, Rämismühle (CH); Andris Zeltins, Riga (LV); Paul Pumpens, Riga (LV)

(73) Assignee: SAIBA AG, Pfäffikon (CH)

(*) Notice: Subject to any disclaimer, the term of this patent is extended or adjusted under 35 U.S.C. 154(b) by 0 days.

This patent is subject to a terminal disclaimer.

(21) Appl. No.: 16/696,161

(22) Filed: Nov. 26, 2019

(65) Prior Publication Data

US 2020/0155699 A1    May 21, 2020

Related U.S. Application Data

(63) Continuation of application No. 15/520,676, filed as application No. PCT/EP2015/074269 on Oct. 20, 2015, now Pat. No. 10,532,107.

(30) Foreign Application Priority Data

Oct. 22, 2014 (EP) .................................. 14189897
Sep. 8, 2015 (EP) .................................. 15184192

(51) Int. Cl.
*A61K 47/64* (2017.01)
*A61K 39/35* (2006.01)
(Continued)

(52) U.S. Cl.
CPC ........ *A61K 47/646* (2017.08); *A61K 39/0005* (2013.01); *A61K 39/0006* (2013.01);
(Continued)

(58) Field of Classification Search
None
See application file for complete search history.

(56) References Cited

U.S. PATENT DOCUMENTS

| 7,939,318 B2 | 5/2011 | Mccormick et al. |
| 8,574,564 B2 | 11/2013 | Renner et al. |

(Continued)

FOREIGN PATENT DOCUMENTS

| JP | 2005-514347 A | 5/2005 |
| JP | 2006-507800 A | 3/2006 |

(Continued)

OTHER PUBLICATIONS

GenBank accession No. AAQ82699.1, coat protein (Cucumber mosaic virus), GenBank Database, Sep. 22, 2003.
(Continued)

*Primary Examiner* — Michelle S Horning
(74) *Attorney, Agent, or Firm* — Medler Ferro Woodhouse & Mills PLLC

(57) ABSTRACT

The present invention relates to virus-like particles of plant virus Cucumber Mosaic Virus (CMV), and in particular to modified VLPs of CMV comprising Th cell epitopes, in particular universal Th cell epitopes. Furthermore, these modified VLPs serve as, preferably, vaccine platform, for generating immune responses, in particular antibody responses, against antigens linked to said modified VLPs. The presence of the Th cell epitopes, in particular universal Th cell epitopes, led to a further increase in the generated immune response.

20 Claims, 14 Drawing Sheets

Figure 1:
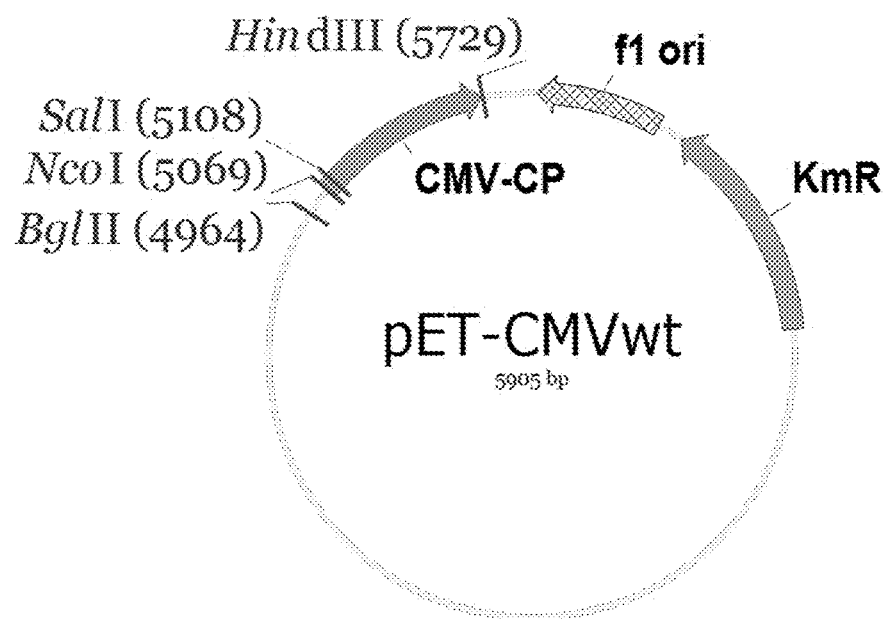
Figure 2:
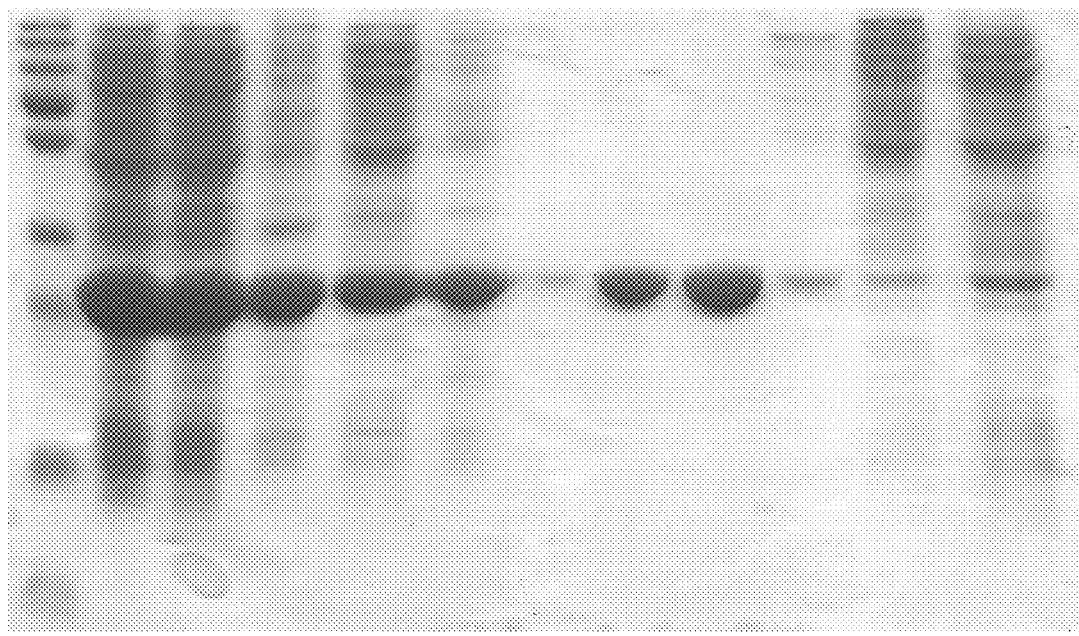
Figure 3A:
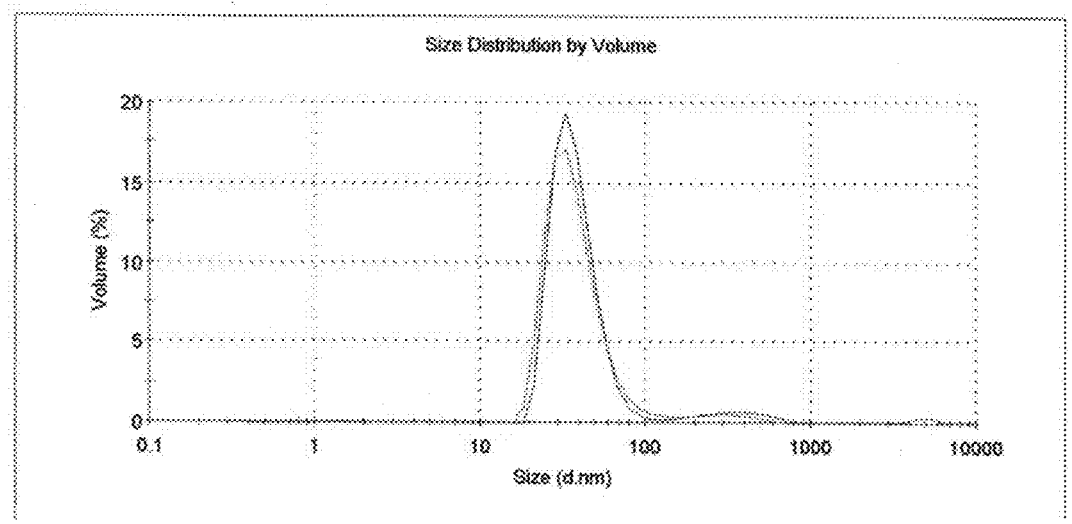
Figure 3B:
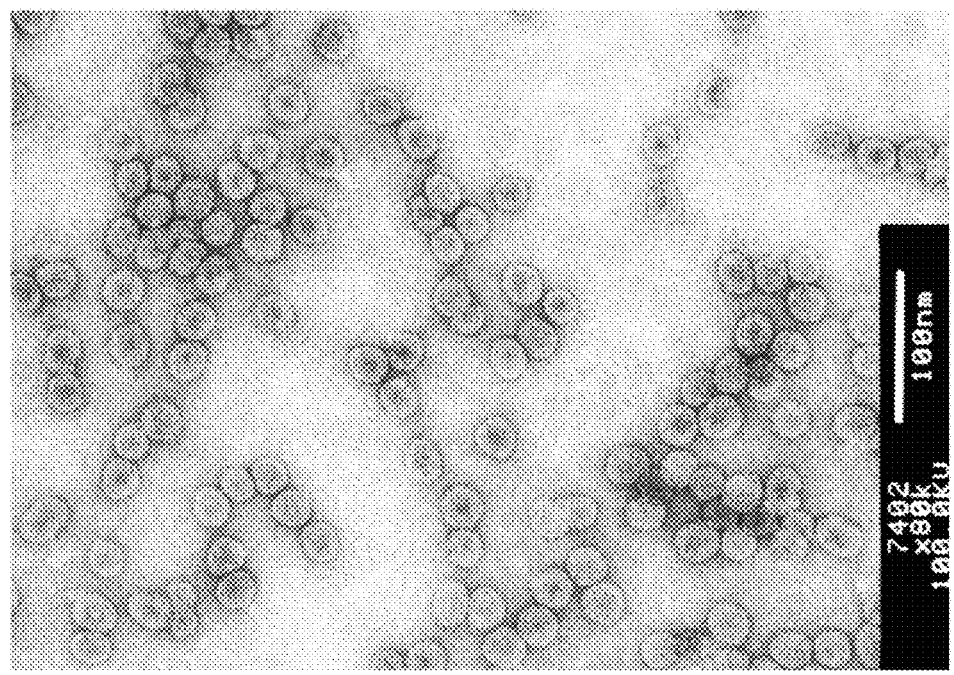
Figure 4A:
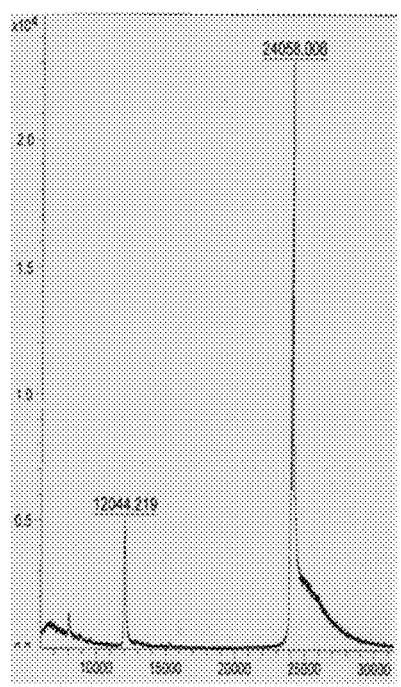
Figure 4B:
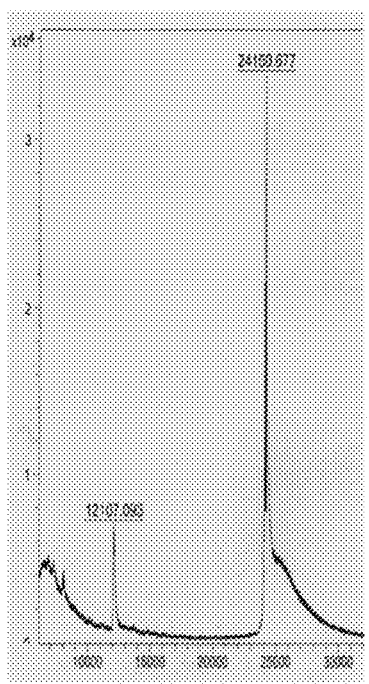
Figure 4C:
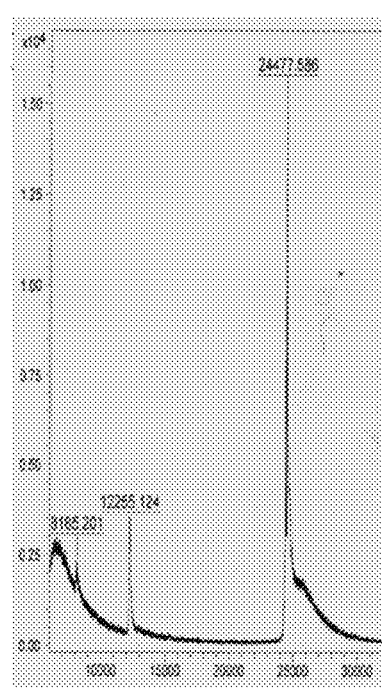
Figure 5A:
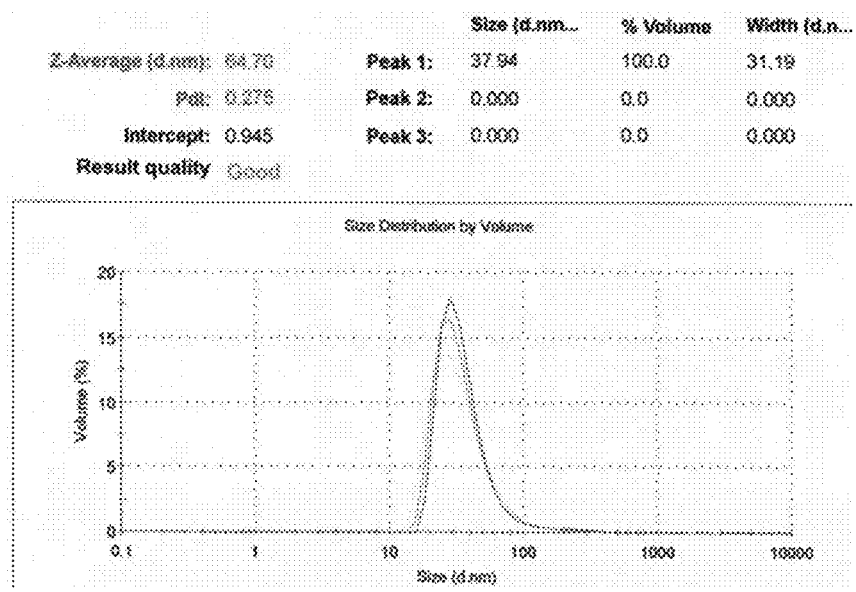
Figure 5B:
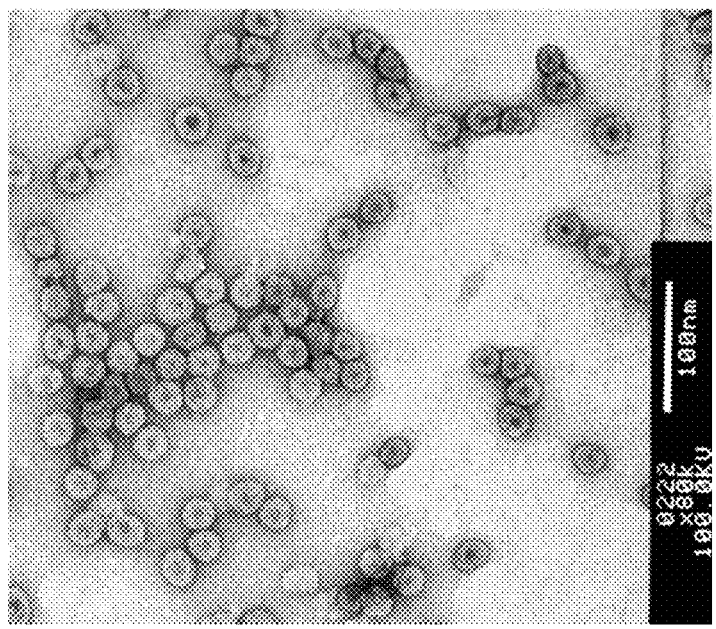
Figure 6A:
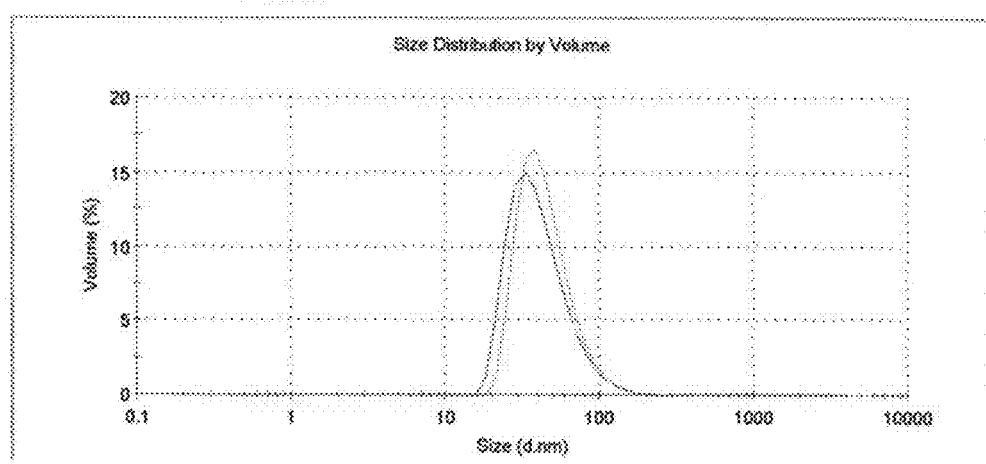
Figure 6B:
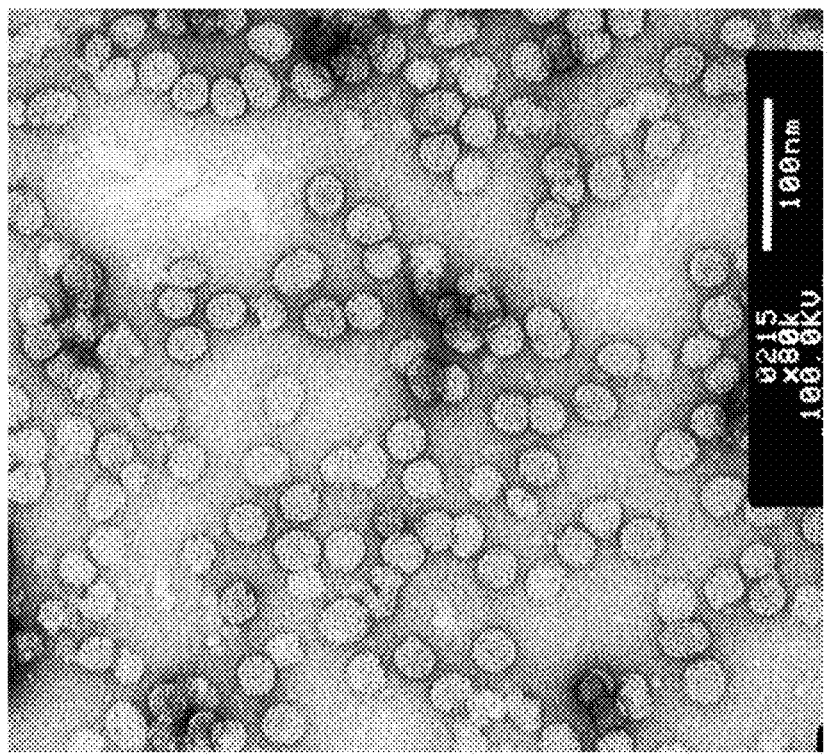

Specification includes a Sequence Listing.

(51) Int. Cl.

| | | |
|---|---|---|
| *C07K 14/005* | (2006.01) | |
| *A61K 39/12* | (2006.01) | |
| *A61K 39/08* | (2006.01) | |
| *A61K 39/00* | (2006.01) | |
| *A61K 39/015* | (2006.01) | |
| *A61K 39/145* | (2006.01) | |
| *A61K 39/155* | (2006.01) | |
| *A61K 39/39* | (2006.01) | |
| *C07K 14/33* | (2006.01) | |
| *C07K 14/725* | (2006.01) | |
| *C12N 7/00* | (2006.01) | |

(52) U.S. Cl.
CPC ...... *A61K 39/0007* (2013.01); *A61K 39/0008* (2013.01); *A61K 39/015* (2013.01); *A61K 39/08* (2013.01); *A61K 39/12* (2013.01); *A61K 39/145* (2013.01); *A61K 39/155* (2013.01); *A61K 39/35* (2013.01); *A61K 39/39* (2013.01); *C07K 14/005* (2013.01); *C07K 14/33* (2013.01); *C07K 14/7051* (2013.01); *C12N 7/00* (2013.01); *A61K 2039/5258* (2013.01); *A61K 2039/55561* (2013.01); *A61K 2039/575* (2013.01); *A61K 2039/6031* (2013.01); *A61K 2039/6037* (2013.01); *A61K 2039/6075* (2013.01); *A61K 2039/6087* (2013.01); *A61K 2039/627* (2013.01); *C07K 2319/00* (2013.01); *C07K 2319/40* (2013.01); *C07K 2319/55* (2013.01); *C07K 2319/74* (2013.01); *C12N 2760/16034* (2013.01); *C12N 2760/16122* (2013.01); *C12N 2760/16134* (2013.01); *C12N 2760/16171* (2013.01); *C12N 2760/18522* (2013.01); *C12N 2760/18534* (2013.01); *C12N 2770/14022* (2013.01); *C12N 2770/14023* (2013.01)

(56) References Cited

U.S. PATENT DOCUMENTS

| 10,050,902 | B2 | 8/2018 | Deguchi |
| 2003/0054010 | A1 | 3/2003 | Sebbel et al. |
| 2018/0250387 | A1 | 9/2018 | Bachmann et al. |
| 2018/0250388 | A1 | 9/2018 | Fettelschoss et al. |

FOREIGN PATENT DOCUMENTS

| WO | 03/040164 A2 | 5/2003 |
| WO | 03/103605 A2 | 12/2003 |
| WO | 2004/052395 A1 | 6/2004 |
| WO | 2005/091753 A2 | 10/2005 |
| WO | 2006/032674 A1 | 9/2006 |
| WO | 2006/097530 A2 | 9/2006 |
| WO | 2013/030608 A1 | 3/2013 |

OTHER PUBLICATIONS

Boitel et al., (Abstract Only), "Strong similarities in Antigen Fine Specificity Among DRB1* 1302-Restricted Tetanus Toxin tt830-843-Specific TCRs in Spite of Highly Heterogeneous CDR3," J. Immunol. 154(7):3245-3255 (1995).

Caldeira et al., "Immunogenic Display of Diverse Peptides, Including a Broadly Cross-type Neutralizing Human Papillomavirus L2 epitope, on Virus-like Articles of the RNA Bacteriophage PP7," Vaccine 28(27):4384-43939 (2010).

Cohen et al., "Is an Effective HIV Vaccine Feasible?" Science 309:99 (2005).

Cong et al., (Abstract Only), "Human Immunome, Bioinformatic Analyses using HLA Supermotifs and the Parasite Genome, Binding Assays, Studies of Human T Cell Responses, and Immunization of HLA-A*1101 Transgenic Mice," Immunome Res.6(12). (2010).

Gellert et al., "A Cucumber Mosaic Virus Based Expression System for the Production of Porcine Circovirus Specific Vaccines," PLoS One 7(12): e52688 (2012).

Halliday et al., (Abstract Only), "Alpha-synuclein Redistributes to Neuromelanin Lipid in the Substantia Nigra Early in Parkinson's Disease," (2005).

Jemon et al., "An Enhanced Heterologous Virus-like Particle for Human Papillomavirus type 16 Tumour Immunotherapy," PLoS One (96): e66866 (2013).

Natilla et al., "Epitope Presentation System Based on Cucumber Mosaic Virus Coat Protein Expressed from a Potato Virus X-based Vector," Arch Virol 151:1373-1386 (2006).

Natilla et al., "Cucumber Mosaic Virus as a Carrier of a Hepatitis C Virus-derived Epitope," Arch Virol. 149(1):137-154 (2004).

Nuzzaci et al., "Structural and Biological Properties of Cucumber Mosaic Virus Particles Carrying Hepatitis C Virus-derived Epitopes," Journal of Virological Methods 155(2):118-121 (2009).

Smith et al., "The Structure of Cucumber Mosaic Virus and Comparison to Cowpea Chlorotic Mottle Virus," J. Virol 74(16):7578-7586 (2000).

Srivastava et al., "Neutralizing Antibody Responses to HIV: Role in Protective Immunity and Challenges for Vaccine Design," Expert Rev. Vaccines 3(4 Suppl):S33-52 (2004).

Tissot et al., "Versatile Virus-like Particle Carrier for Epitope Based Vaccines," PLoS One 5(3):e9809 (2010).

International Search Report for PCT/EP2015/074269, dated Dec. 11, 2015.

Notice of Reasons for Rejection issued in Japanese Application No. 2017-522532 dated Sep. 24, 2019.

UniProtKB/Swiss-Prot: Q8DJX6, CMV coat protein (2006).

MODIFIED VIRUS-LIKE PARTICLES OF CMV

The instant application contains a Sequence Listing which has been submitted electronically in ASCII text format and is hereby incorporated by reference in its entirety. Said ASCII text copy, created on Mar. 29, 2017, is named 0192026US1sequencelisting.txt and is 65,000 bytes in size.

The present invention relates to virus-like particles of plant virus Cucumber Mosaic Virus (CMV), and in particular to modified VLPs of CMV comprising Th cell epitopes, in particular universal Th cell epitopes. Furthermore, these modified VLPs serve as, preferably, vaccine platform, for generating immune responses, in particular antibody responses, against antigens linked to said modified VLPs. The presence of the Th cell epitopes, in particular universal Th cell epitopes, led to a further increase in the generated immune response.

RELATED ART

Over the last three decades, virus-like particles (VLPs) have evolved to become an accepted technology, in particular in the field of vaccine development (Zeltins A, Mol Biotechnol (2013) 53:92-107). The growing interest in these VLPs was particularly inspired by the successful development and introduction of the hepatitis B virus (HBV) surface antigen and the human papilloma virus (HPV) capsid protein L1 as commercial vaccines against hepatitis B and HPV-induced cervical cancer, respectively. Moreover, virus-like particles have been described as immunological carriers which are capable of inducing strong immune responses against conjugated antigens (Jennings G T and Bachmann M F, Annu Rev Pharmacol Toxicol (2009) 49:303-26, Jennings G T and Bachmann M F, Biol Chem (2008) 389:521-536, WO2002/056905, WO2003/024481). The latter led to the development of several VLP-based vaccine candidates that have entered different stages of clinical investigations with the aim to develop VLP-based vaccines for medical and veterinary purposes in the near future (Liu F, et al., Research in Veterinary Science (2012) 93:553-559; Roldao A., et al., Expert Review of Vaccines (2010) 9:1149-1176).

The VLPs developed so far originated from microbial, plant, insect or mammalian viruses. Beside the above referenced VLP systems, VLPs derived from plant viruses have recently attracted attention, mainly due to the role of plants as an economical and speedy alternative platform for producing VLP vaccines in the light of their ability to provide distinctive posttranslational modifications, cost-effectiveness, production speed and scalability (Chen Q and Lai H, Human Vaccines & Immunotherapeutics (2013) 9:26-49; Zeltins A, Mol Biotechnol (2013) 53:92-107).

Cucumber Mosaic Virus (CMV, family, Bromoviridae, genus, Cucumovirus) is a linear positive-sense isodiametric plant virus with an extremely wide host range. The virus genome consists of three single-stranded RNAs (RNA1, RNA2 and RNA3), the coat protein (CP) gene being present both in the genomic RNA3 (about 2200 nt) and in the subgenomic RNA4 (about nt). The capsid comprises 180 copies of a single protein species of about 26 kDa. There are a plurality of different strains known from CMV associated with variable symptoms related to the host plant such as CMV-B strain, CMV-C strains CMV-D strain, CMV-L strains, CMV-S strain, CMV-T strain, CMV-WL-strain, CMV-V strains, CMV-Fny strain, CMV-Ix strain, CMV-Q strain, CMV-R strain or the like (Carrère I, et al., Arch Virol (1999) 144:1846-1857; Edwards M C, et al., Phytopathology 81983) 73:1117-1120; dpvweb.net).

Recently, chimeric forms of CMV have been engineered to function as a presentation system and to express on their outer surface epitopes derived from the hepatitis C virus (HCV). In detail, a CMV pseudo-recombinant form CMV-D/S has been engineered to carry genomic RNA3 from the CMV-S strain and RNA1 and RNA2 from the CMV-D strain. This system developed virus symptoms such as mild mosaic and vein clearing in Xanthi tobacco plants after inoculation. The CP gene was then engineered in different positions, to encode a Hepatitis C virus (HCV) epitope. The selected peptide was the so-called R9 mimotope, a synthetic peptide derived from many hypervariable region 1 (HVR1) sequences of the HCV envelope protein E2. Serum samples from patients with chronic hepatitis C displayed a significant immunoreactivity to crude plant extracts infected with one of the selected engineered pseudo-recombinant chimeric forms of CMV. It has, therefore, been suggested that such systems may be suitable carriers enabling the development of promising oral immunization strategies. The latter would be in line with the concept of plants as possible bioreactors of the so-called nutraceuticals since they actively replicate in plants and, thus, are conceivable to be used as edible vaccines because celery, lettuce, cucumber, tomato, carrot, pepper and banana are hosts of CMV. (Natilla A, et al., Arch Virol (2004) 149:137-154; Piazzolla G, et al., J Clin Immunol (2005) 25:142-152; Nuzzaci M, et al., Arch Virol (2007) 152:915-928; Nuzzaci M, et al., Journal of Virological Methods (2009) 155:118-121; Nuzzaci M, et al., Journal of Virological Methods (2010) 165:211-215; Piazzolla G, et al., J Clin Immunol (2012) 32:866-876).

The insertion of the R9 mimotopes has been effected at different locations within the CP gene of CMV-S RNA3 (AF063610, dpvweb.net). For the insertion of one single R9 mimotope within said CP gene, the R9 mimotope nucleotide sequence was inserted in positions 253, 475, 529 of said CP gene, whereas for the insertion of two R9 mimotopes, the R9 mimotope nucleotide sequence was inserted in position 392 and 529. The final products were CMV chimeric particles carrying on their outer surface 180 or 360 copies of the R9 mimotope for each virus particle. (Natilla A, et al., Arch Virol (2004) 149:137-154; Piazzolla G, et al., J Clin Immunol (2005) 25:142-152; Nuzzaci M, et al., Arch Virol (2007) 152:915-928; Nuzzaci M, et al., Journal of Virological Methods (2009) 155:118-121; Nuzzaci M, et al., Journal of Virological Methods (2010) 165:211-215; Piazzolla G, et al., J Clin Immunol (2012) 32:866-876).

It has been stated that the selection of the insertion points of the R9 mimotope into the CMV-S RNA3 was based on taking several some essential factors into account: i) the need to protect the N-terminal region of the CMV coat protein (containing a high concentration of basic amino acids, known as an internal R-domain, involved in protein-RNA interactions stabilizing CMV (Wikoff W R, et al., Virology (1997) 232: 91-97)) characterized by an unusual N-terminal helix with an additional stabilizing role in the capsid (Smith T J, et al., J Virol (2000) 74: 7578-7686)); ii) the surface location of the foreign epitope to increase the chance of its putative immunogenic capability; iii) the availability of mutagenesis routes able to produce the modified clones. On the basis of these considerations it has been focused to work on the aa range 70-192 and the corresponding nucleotide regions as indicated above. The so prepared chimeric CMVs retained their ability to spread systemically in the host plant, which is an irreplaceable goal in the building of a potential plant virus carrier for foreign gene expression in plants. ELISA and IEM tests demonstrated that the R9 mimotope was exposed as planned in the right position (Natilla A, et al., Arch Virol (2004) 149:137-154).

Furthermore, a cucumber mosaic virus based expression system for the production of porcine circovirus specific vaccines has recently been described (Gellert A, et al., PLoS ONE (2012) 7(12): e52688). In detail, porcine circovirus type 2 (PCV2) capsid protein epitopes were integrated into the plant virus coat protein of cucumber mosaic virus (CMV)-R strain after amino acid position 131. The recombinants were tested for infectivity and stability on different Nicotiana species and stable recombinant virus particles were purified. The particles were tested for their ability to bind to PCV induced porcine antibodies and used for specific antibody induction in mice and pigs. The results showed that PCV epitopes expressed on the CMV surface were recognized by the porcine antibodies and they were also able to induce PCV specific antibody response. Challenge experiment with PCV2 carried out in immunized pigs showed partial protection against the infection.

The PCV2 capsid protein epitopes were integrated in the coat protein of cucumber mosaic virus (CMV) at the three stable epitope insertion points of CMV reported to date (Nuzzaci M, et al., Arch Virol (2007) 152:915-928; Vitti A, et al., J Virol Methods (2010) 169:332-340). The built-in epitopes at these points did not block the propagation of CMV and the long-distance movement in plants. Two of them are displayed on the external surface of the virion while the third protrudes towards the inside of the virion. There is an electrostatic limitation to express epitopes facing the inside of the virion as only the expression of epitopes with positive charge, that do not interfere with the RNA-binding of the inner surface of the CMV capsid can successfully be attempted. In detail, the first insertion point is located at position of aa 83-84 and at the end of the βBβC loop of the CMV CP. The built-in epitopes are expressed on the surface of CMV virions. The second insertion point is located at position of aa 131-132 and in the middle of the βE-αEF loop of the CMV CP. The built-in epitopes are also expressed on the surface of CMV virions. The third insertion point is located at position of aa 176-177 and in the middle of the βG-βH loop. In this latter case the inserted epitopes are expressed on the inner surface of CMV virions.

Furthermore, the generation of chimeric virus-like particles (VLPs) based on CMV has been described and its use as an animal vaccine suggested (Natilla, A, et al., Arch Virol (2006) 151:1373-1386; Natilla, A, et al., Protein Expression and Purification (2008) 59:117-121). However, the expression of the viral capsid proteins (CPs) of CMV by the widely used traditional E. coli expression system led only to insoluble inclusion bodies or a very low quantity of soluble proteins (Xu Y, et al., Chem Commun (2008) 49-51). On the other hand, Potato virus X (PVX)-expressed coat protein (CP) of CMV-Fny formed VLPs, which served as carriers for surface display of different neutralizing epitopes of Newcastle disease virus (NDV), an economically important pathogen of poultry. For this purpose, epitopes from fusion (F), hemagglutinin-neuraminidase (NH) protein and the tandem F-NH peptide were genetically fused into the internal βH-βI (motif 5) loop of the Fny-CMV CP (corresponding to amino acids 194-199 thereof) and expressed via the PVX vectors in Nicotiana benthamiana plants. The resulting chimeric CMV VLPs are morphologically indistinguishable from wild type CMV particles. Moreover, chickens immunized with purified NH-CMV VLPs developed antigen-specific antibody responses, however, the so immunized chickens were not protected against experimental challenge with NDV (Natilla, A, et al., Arch Virol (2006) 151:1373-1386; Natilla, A, et al., Protein Expression and Purification (2008) 59:117-121; Chen Q and Lai H, Human Vaccines & Immunotherapeutics (2013) 9: 26-49).

As indicated, the expression of the viral capsid proteins (CPs) of CMV in E. coli led only to insoluble inclusion bodies or a very low quantity of soluble proteins (Xu Y, et al., Chem Commun (2008) 49-51). On the other hand, Xu et al were able to in vitro assembly genetically recombinant CPs of CMV into biological nanotubes triggered by double-stranded DNAs of different lengths (Xu Y, et al., Chem Commun (2008) 49-51). For this purpose, however, Xu et al had to produce pure soluble CMV CPs. This was achieved by a recombination procedure after the expression of the CPs in E. coli. The procedure comprises the separation and purification of the inclusion bodies formed after the expression of the full-length CP gene of 218 amino acid residues (ID AB008777, dpvweb.net), followed by solubilization of the inclusion bodies via denaturation and, finally by applying a refolding procedure to the denatured protein.

Even though progress has been made in the course of the development of VLP based vaccines, there is still a need for further distinct VLP systems. In particular, vaccines induce variable antibody responses in immunized subjects and individuals and antibody responses often span a range of more than 100-fold variation. In addition, some vaccines, such as the vaccine against Hepatitis B, suffer from a certain number of non-responders. Non-responsiveness is known to be associated with certain MHC class II molecules and it is believed that a failure to induce good T helper (Th) cell responses is responsible for the poor antibody responses seen in these individuals (Goncalves L, et al., Virology (2004) 326:20-28). Furthermore, elderly and old people mount poor antibody responses in general and poor Th cell responses are again thought to be the cause of the inefficient antibody responses. Therefore, vaccines inducing good Th cell responses in essentially all subjects and individuals are an important goal in the field of vaccine development.

SUMMARY OF THE INVENTION

We have surprisingly found that coat proteins of cucumber mosaic virus (CMV) can be modified to incorporate T helper (Th) cell epitopes, and preferably to incorporate universal Th cell epitopes. The latter is in particular surprising since these strong Th cell epitopes are known to cause aggregation and, thus, would be expected to hinder self-assembly upon expression leading to VLPs. Moreover, not only provides the present invention modified CMV VLPs comprising Th cell epitopes, preferably universal Th cell epitopes, but furthermore the inventive modified CMV VLPs as well as the wild-type CMV VLP have been obtained by expression in E. coli, which again is surprising as previous attempts to produce CMV VLPs in E. coli resulted in aggregates rather than VLPs. In addition, the inventive VLPs serve as a carrier platform, in particular a vaccine platform, wherein antigens to which immune responses are desired to be generated are linked to the inventive VLPs. The introduced Th cell epitopes incorporated within the inventive modified VLPs of CMV further increased the immunogenicity of the VLPs and led to an increase of the overall immune responses generated by the inventive compositions, in particular to increased antibody responses.

Thus in a first aspect, the present invention provides for a modified virus-like particle (VLP) of cucumber mosaic virus (CMV), wherein said modified VLP of CMV comprises, essentially consists of, or alternatively consists of, at least one modified CMV polypeptide, wherein said modified CMV polypeptide comprises, or preferably consists of, (a) a CMV polypeptide, and (b) a T helper cell epitope; and wherein said CMV polypeptide comprises, or preferably consists of, (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%.

In another aspect, the present invention provides for a modified virus-like particle (VLP) of cucumber mosaic virus (CMV), wherein said modified VLP of CMV comprises, essentially consists of, or alternatively consists of, at least one modified CMV polypeptide, wherein said modified CMV polypeptide comprises, or preferably consists of, (a) a CMV polypeptide, and (b) a T helper cell epitope; and wherein said CMV polypeptide comprises, or preferably consists of, (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%; wherein said T helper cell epitope (i) is fused to the N-terminus of said CMV polypeptide; (ii) is fused to the C-terminus of said CMV polypeptide; (iii) replaces a region of consecutive amino acids of said CMV polypeptide, wherein the sequence identity between said replaced region of consecutive amino acids of said CMV polypeptide and the T helper cell epitope is at least 15%, preferably at least 20%; or (iv) replaces a N-terminal region of said CMV polypeptide, and wherein said replaced N-terminal region of said CMV polypeptide consists of 5 to 15 consecutive amino acids.

In another aspect, the present invention provides for a virus-like particle (VLP) of cucumber mosaic virus (CMV), wherein said VLP of CMV comprises, essentially consists of, or alternatively consists of, at least one CMV polypeptide comprising or preferably consisting of: (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said a coat protein of CMV show a sequence identity of at least 90%, preferably of at least 95%, further preferably of at least 98% and again more preferably of at least 99%; and wherein said VLP of CMV is obtained by expression of said CMV polypeptide in *E. coli*, and wherein preferably said expression is effected at temperatures of between 10° C. to 25° C., preferably at a temperature of 20° C.

In another aspect, the present invention provides for a composition comprising a modified virus-like particle. Furthermore, these modified VLPs serve as, preferably, vaccine platform, for generating immune responses, in particular antibody responses, against antigens linked to said modified VLPs. The presence of the Th cell epitopes, in particular universal Th cell epitopes, led to a further increase in the generated immune response.

Further aspects and preferred embodiments thereof are described herein in more detail.

BRIEF DESCRIPTION OF FIGURES

FIG. 1 pET-CMVwt plasmid map. The relative positions of all relevant genes and restriction enzyme sites are denoted.

FIG. 2 SDS/PAGE analysis of expression and sucrose gradient purification of CMVwt protein. M—protein size marker; S—soluble proteins after ultrasonication; P—insoluble proteins after ultrasonication; Ps—soluble proteins in ammonium sulfate pellet (sample for sucrose gradient ultracentrifugation); Pp—insoluble proteins in ammonium sulfate pellet; 1, 2, 3, 4, 5, 6—sucrose gradient fractions from the bottom of 35 ml gradient tube.

FIG. 3A Dynamic light scattering of purified CMVwt VLPs. The size of particles was detected by using Zetasizer Nano ZS (Malvern Instruments Ltd., United Kingdom).

FIG. 3B Electron-microscopy analysis of purified CMVwt VLPs. For the morphological analysis of VLPs the JEM-1230 electron microscope (Jeol Ltd., Tokyo, Japan) was used.

FIGS. 4A, 4B, and 4C Mass spectrometric analysis of purified CMV-derived VLPs. Matrix-assisted laser desorption/ionization (MALDI)-TOF MS analysis was carried out on an Autoflex MS (Bruker Daltonik, Germany). The protein molecular mass (MM) calibration standard II (22.3-66.5 kDa; Bruker Daltonik) was used for mass determination.

FIG. 4A CMVwild-type ("wt"); theoretical MM=24069; found MM=24058 FIG. 4B CMV-Npadr; theoretical MM=24161 (without first Met); found MM=24160 FIG. 4C CMV-Ntt830; theoretical MM=24483 (without first Met); found MM=24477 FIG. 5A Dynamic light scattering of purified CMV-Ntt830 VLPs. The size of particles was detected by using Zetasizer Nano ZS (Malvern Instruments Ltd., United Kingdom).

FIG. 5B Electron-microscopy analysis of purified CMV-Ntt830 VLPs. For the morphological analysis of VLPs the JEM-1230 electron microscope (Jeol Ltd., Tokyo, Japan) was used.

FIG. 6A Dynamic light scattering of purified CMV-Npadr VLPs. The size of particles was detected by using Zetasizer Nano ZS (Malvern Instruments Ltd., United Kingdom).

FIG. 6B Electron-microscopy analysis of purified CMV-Npadr VLPs. For the morphological analysis of VLPs the JEM-1230 electron microscope (Jeol Ltd., Tokyo, Japan) was used.

FIG. 7A The antibody response was measured after immunization of CMV wild type VLP. Groups of mice were immunized with either 10 μg, 1 μg or 0.1 μg of CMV-wt VLP on day 0 and 7. The specific total IgG titer was measured on day 0 (pre-immune), 7, 14 and 28. Mice per group=4.

FIG. 7B The antibody response was measured after immunization of CMV-Npadr VLP. Groups of mice were immunized with either 10 μg, 1 μg or 0.1 μg of CMV-Npadr VLP on day 0 and 7. The specific total IgG titer was measured on day 0 (pre-immune), 7, 14 and 28. Mice per group=4.

FIG. 7C The antibody response was measured after immunization of CMV-Ntt830 VLP. Groups of mice were immunized with either 10 μg, 1 μg or 0.1 μg of CMV-Ntt830 VLP on day 0 and 7. The specific total IgG titer was measured on day 0 (pre-immune), 7, 14 and 28. Mice per group=4.

FIG. 8A The humoral response against the allergen Fel D1 was detected in mice. The major cat allergen Fel D1 was coupled to CMV Npadr. Mice were immunized with 5 μg of Fel D1-VLP on day 0 and 7. Fel D1 specific antibodies were measured at indicated time points. Mice per group=5.

Figure 8A:
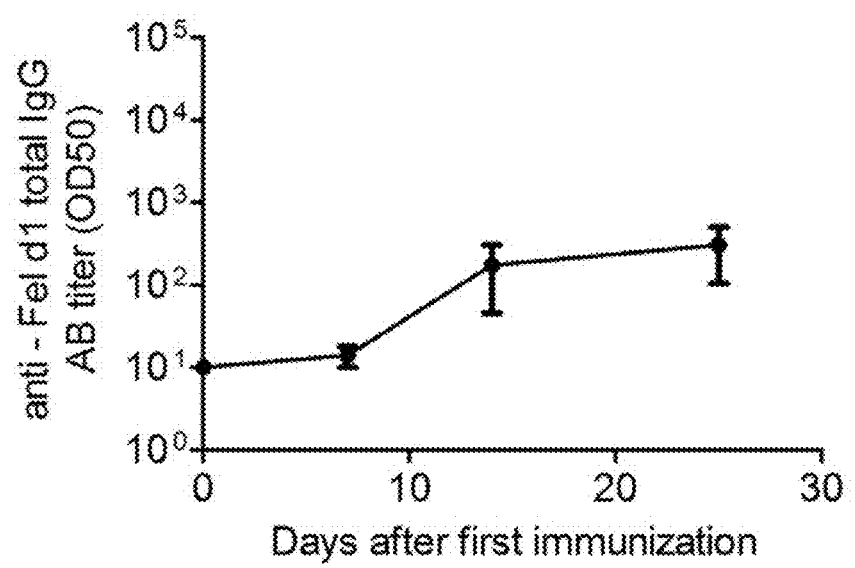
Figure 8B:
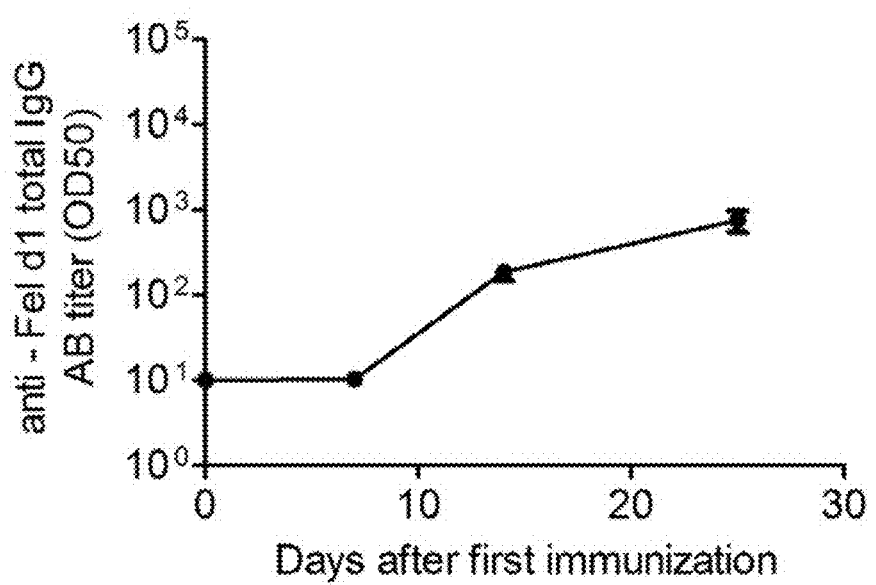

FIG. 8B The humoral response against the allergen Fel D1 was detected in mice. The major cat allergen Fel D1 was coupled to CMV Ntt830. Mice were immunized with 5 μg of Fel D1-VLP on day 0 and 7. Fel D1 specific antibodies were measured at indicated time points. Mice per group=5

Figure 9:
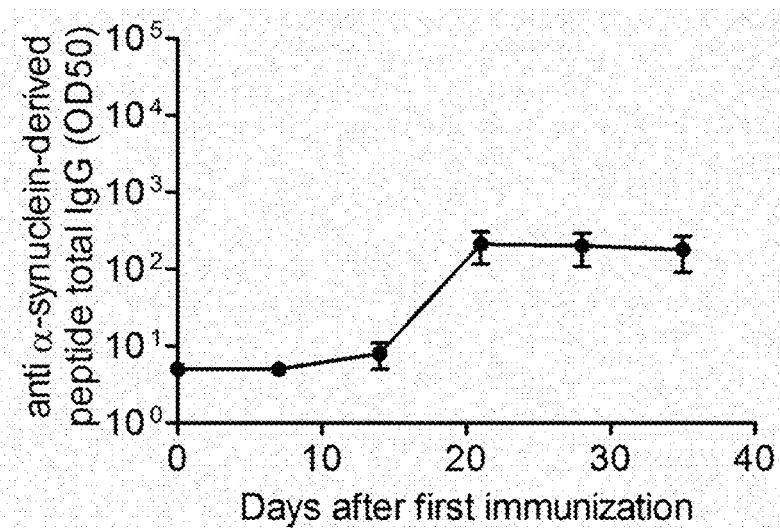

FIG. 9 The humoral response against α-synuclein derived peptide is shown. Mice were immunized on day 0 and 14 with 20 μg α-synuclein derived peptide coupled to CMV Ntt830. The peptide specific antibody titer was measured at indicated time points. Number of mice=4.

Figure 10:
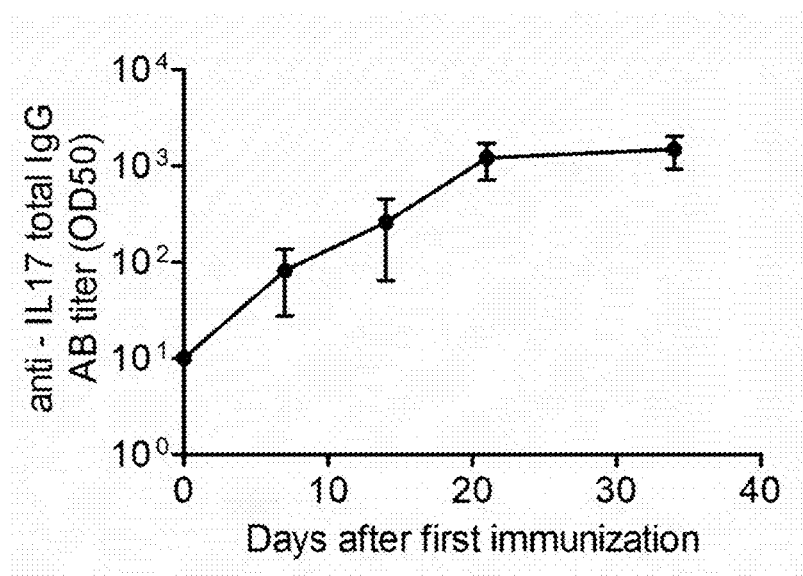

FIG. 10 The antibody response against the self protein IL17 was detected in mice. The cytokine IL17 was coupled to CMV Ntt830. Mice were immunized with 20 μg of IL17-CMV Ntt830 on day 0 and 14. IL17 specific antibodies were measured at indicated time points. Number of mice=3.

Figure 11A:
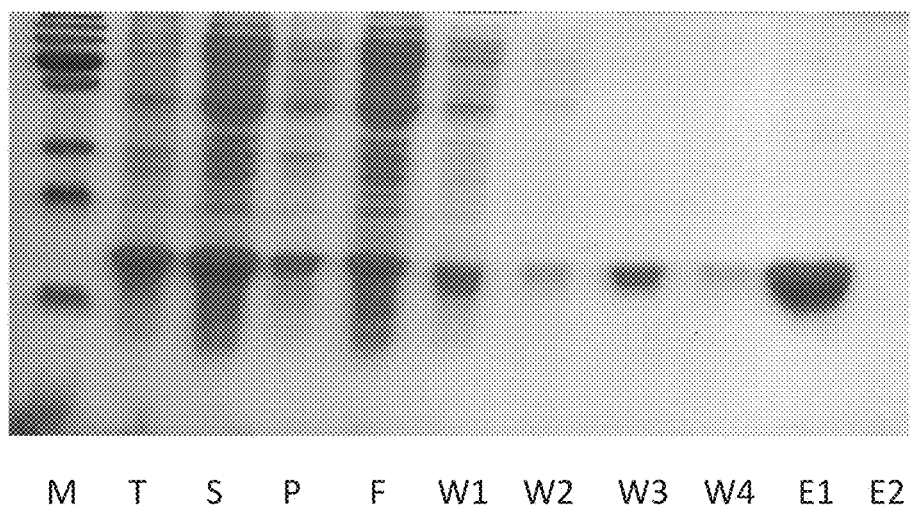

FIG. 11A SDS/PAGE analysis of expression and purification of F12H6GGC protein from $E.\ coli$ C2566 cells, using PrepEase kit (USB). M—protein size marker; S—soluble protein fraction; P—cell debris; F—Flow through from Ni-IDA column (unbound proteins); W1, W2—Wash fractions (2×2 ml 1×LEW buffer) W3, W4 Wash fractions (2×2 ml 1×LEW+10 mM imidazole); E1, E2—Elution fractions (2×1.5 ml E buffer 250 mM imidazole).

Figure 11B:
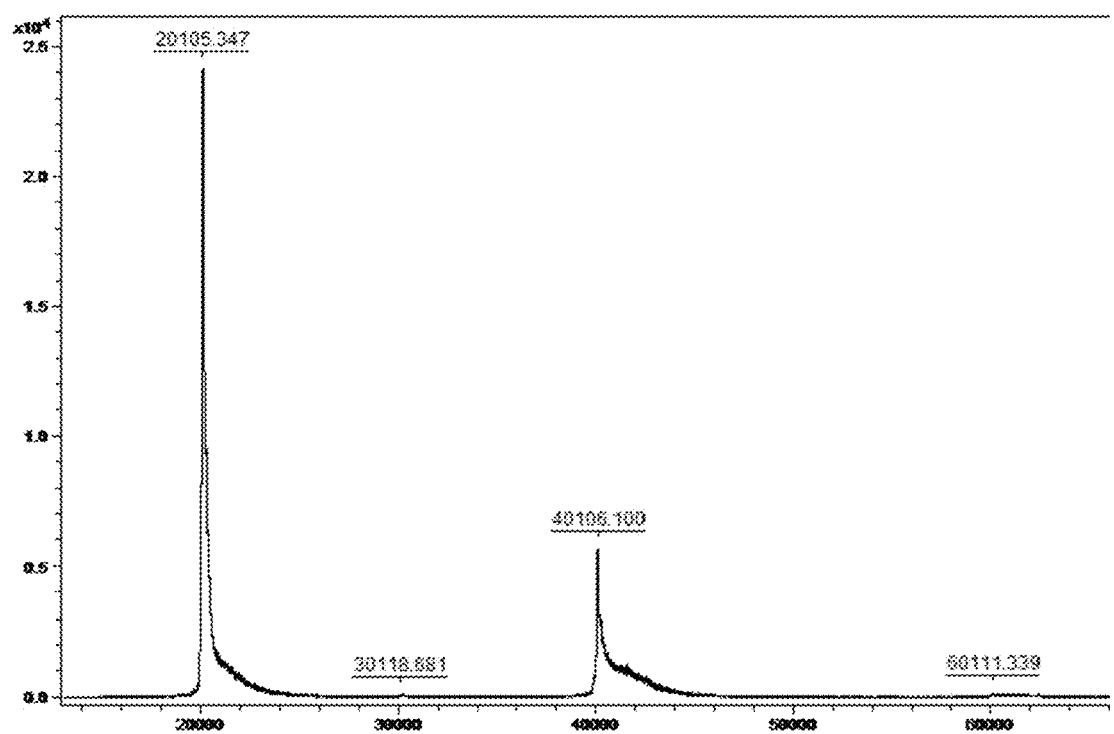

FIG. 11B Mass spectrometric analysis of purified F12H6GGC. The calculated average mass of the F12H6GGC corresponds to 20089.8 Da. The observed mass of 20105.3 corresponds to F12H6GGC where one sulfur of a methionine is oxidized to a sulfoxide group.

Figure 11C:
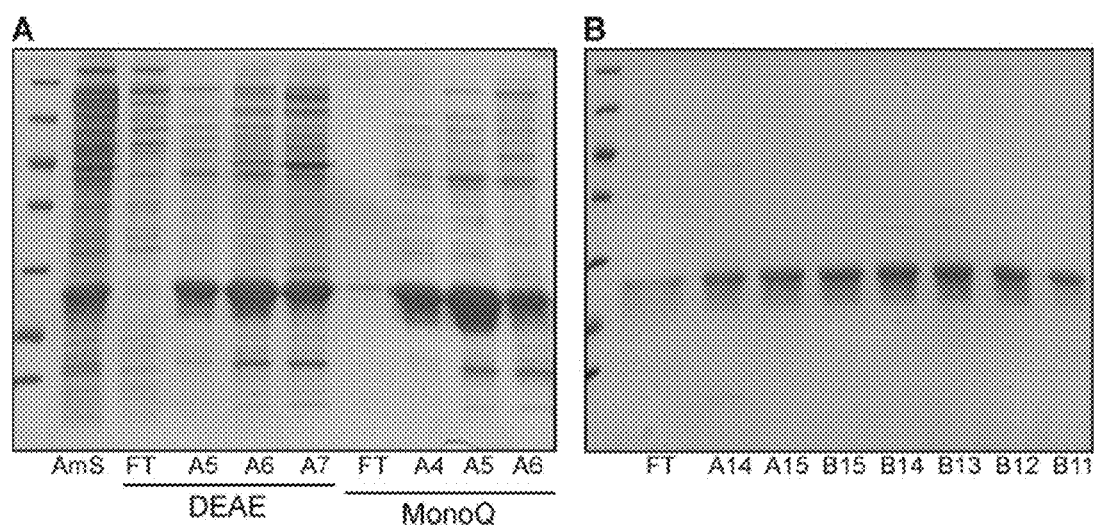

FIG. 11C Coomassie Blue stained SDS-PAGE analysis of purification of F12GGC. (A) AmS—dissolved precipitate after 50% $(NH_4)_2SO_4$. Various fractions from the DEAE column procedure and subsequent purification by MonoQ: FT—flow through, A4-A7—fractions eluted by increasing NaCl gradient (B) Final purification by Butyl HP column (HIC).

Figure 12:
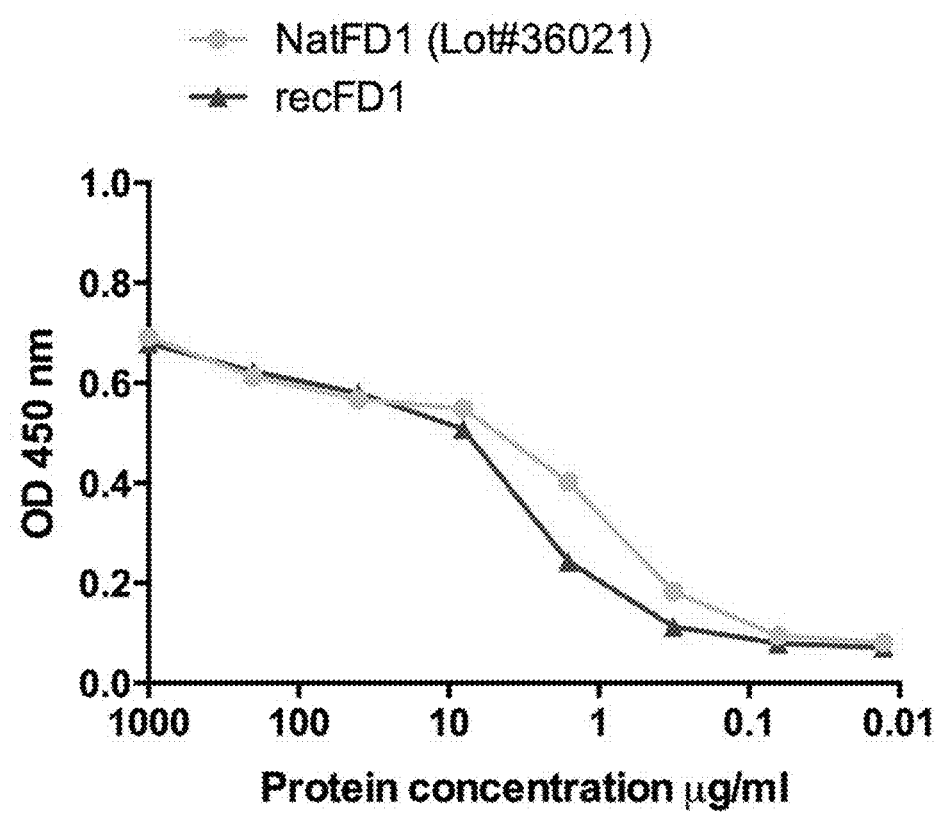

FIG. 12 A sandwich ELISA supplied from Indoor Biotechnologies using mAbs raised against the natural Fel d1 is shown. The mAbs recognize F12H6GGC and natural Fel d1 equally well.

Figure 13A:
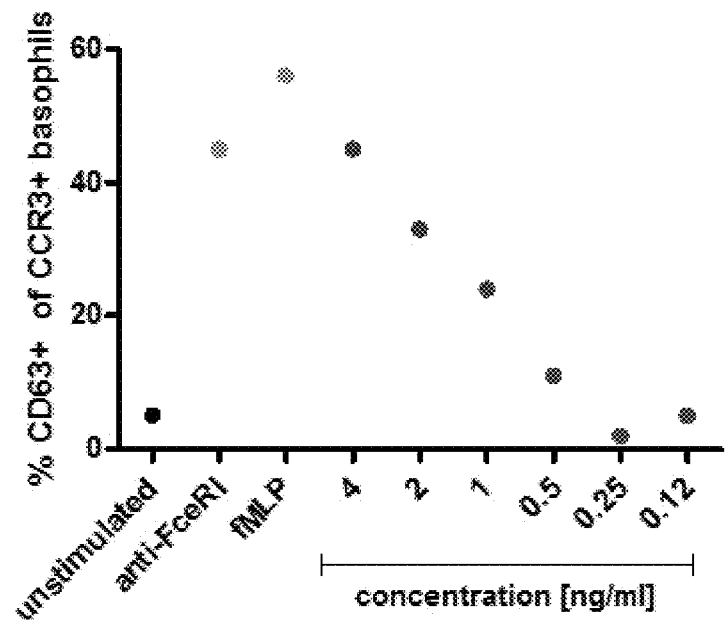

FIG. 13A Basophil activation test (BAT) for natural Fel d1.

Figure 13B:
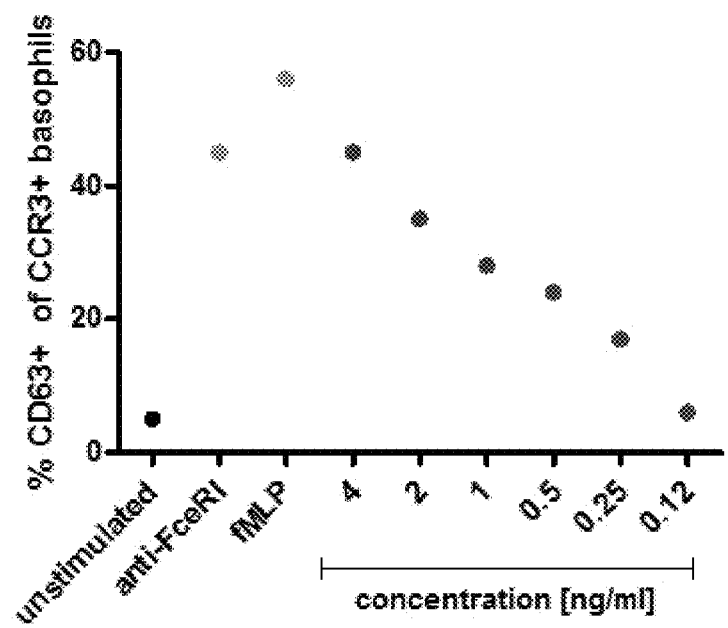

FIG. 13B Basophil activation test (BAT) for F12H6GGC. F12H6GGC and natural Fel d1 induce similar activation levels of basophils in blood from cat allergic patients indicated by the up-regulation of CD63 on CCR3+ basophils.

Figure 14:
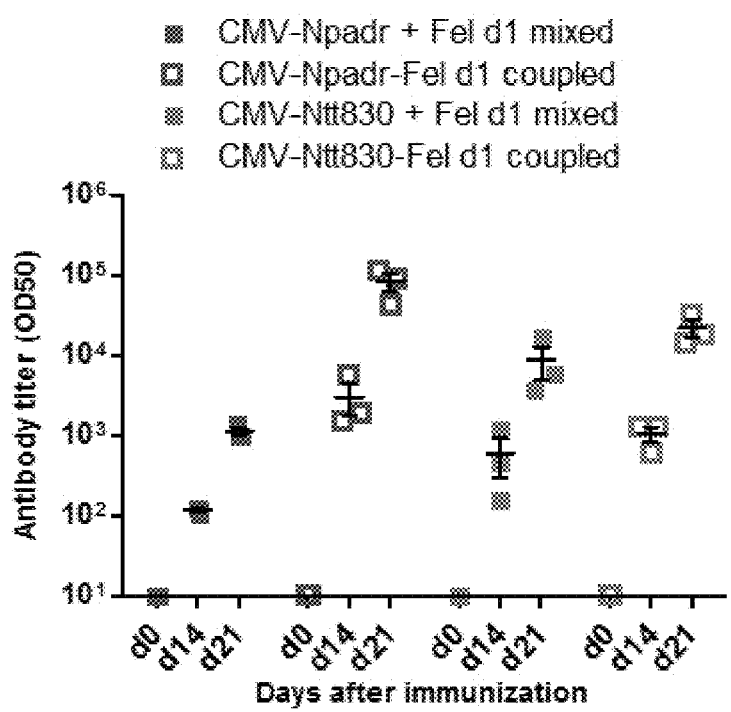

FIG. 14 Antibody response of mice which received 10 μg of either Fel d1-CMV VLPs (Fel d1-CMV-Ntt830-VLP or Fel d1-CMV-Npadr-VLP) or CMV-VLPs (CMV-Ntt830-VLP or CMV-Npadr-VLP) simply mixed with Fel d1 fusion protein F12H6GGC on day 0 and day 14. Serum was collected on day 0, 14 and 21 and analyzed by ELISA for natural Fel d1 specific IgG-antibodies. N=3.

DETAILED DESCRIPTION OF THE INVENTION

Unless defined otherwise, all technical and scientific terms used herein have the same meanings as commonly understood by one of ordinary skill in the art to which this invention belongs.

Virus-like particle (VLP): The term "virus-like particle (VLP)" as used herein, refers to a non-replicative or non-infectious, preferably a non-replicative and non-infectious virus particle, or refers to a non-replicative or non-infectious, preferably a non-replicative and non-infectious structure resembling a virus particle, preferably a capsid of a virus. The term "non-replicative", as used herein, refers to being incapable of replicating the genome comprised by the VLP. The term "non-infectious", as used herein, refers to being incapable of entering the host cell. A virus-like particle in accordance with the invention is non-replicative and non-infectious since it lacks all or part of the viral genome or genome function. A virus-like particle in accordance with the invention may contain nucleic acid distinct from their genome. Recombinantly produced virus-like particles typically contain host cell derived RNA. A typical and preferred embodiment of a virus-like particle in accordance with the present invention is a viral capsid composed of polypeptides of the invention. A virus-like particle is typically a macromolecular assembly composed of viral coat protein which typically comprises 60, 120, 180, 240, 300, 360, or more than 360 protein subunits per virus-like particle. Typically and preferably, the interactions of these subunits lead to the formation of viral capsid or viral-capsid like structure with an inherent repetitive organization. One feature of a virus-like particle is its highly ordered and repetitive arrangement of its subunits.

Virus-like particle of CMV: The terms "virus-like particle of CMV" or CMV VLPs refer to a virus-like particle comprising, or preferably consisting essentially of, or preferably consisting of at least one CMV polypeptide. Preferably, a virus-like particle of CMV comprises said CMV polypeptide as the major, and even more preferably as the sole protein component of the capsid structure. Typically and preferably, virus-like particles of CMV resemble the structure of the capsid of CMV. Virus-like particles of CMV are non-replicative and/or non-infectious, and lack at least the gene or genes encoding for the replication machinery of the CMV, and typically also lack the gene or genes encoding the protein or proteins responsible for viral attachment to or entry into the host. This definition includes also virus-like particles in which the aforementioned gene or genes are still present but inactive. Preferred methods to render a virus-like particle of CMV non replicative and/or non-infectious is by physical or chemical inactivation, such as UV irradiation, formaldehyde treatment. Preferably, VLPs of CMV lack the gene or genes encoding for the replication machinery of the CMV, and also lack the gene or genes encoding the protein or proteins responsible for viral attachment to or entry into the host. Again more preferably, non-replicative and/or non-infectious virus-like particles are obtained by recombinant gene technology. Recombinantly produced virus-like particles of CMV according to the invention typically and preferably do not comprise the viral genome. Virus-like particles comprising more than one species of polypeptides, often referred to as mosaic VLPs are also encompassed by the invention. Thus, in one embodiment, the virus-like particle according to the invention comprises at least two different species of polypeptides, wherein at least one of said species of polypeptides is a CMV polypeptide. Preferably, a VLP of CMV is a macromolecular assembly composed of CMV coat protein which typically comprises 180 coat protein subunits per VLP. Typically and preferably, a VLP of CMV as used herein, comprises, essentially consists of, or alternatively consists of, at least one CMV polypeptide comprising or preferably consisting of (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said amino acid sequence to be mutated show a sequence identity of at least 90%, preferably of at least 95%, further preferably of at least 98% and again more preferably of at least 99%.

Polypeptide: The term "polypeptide" as used herein refers to a polymer composed of amino acid monomers which are linearly linked by peptide bonds (also known as amide bonds). The term polypeptide refers to a consecutive chain of amino acids and does not refer to a specific length of the product. Thus, peptides, and proteins are included within the definition of polypeptide.

Cucumber Mosaic Virus (CMV) polypeptide: The term "cucumber mosaic virus (CMV) polypeptide" as used herein refers to a polypeptide comprising or preferably consisting of: (i) an amino acid sequence of a coat protein of cucumber mosaic virus (CMV), or (ii) a mutated amino acid sequence, wherein the amino acid sequence to be mutated is an amino acid sequence of a coat protein of CMV, and wherein said mutated amino acid sequence and said amino acid sequence to be mutated, i.e. said coat protein of CMV, show a sequence identity of at least 90%, preferably of at least 95%, further preferably of at least 98% and again more preferably of at least 99%. Typically and preferably, the CMV polypeptide is capable of forming a virus-like particle of CMV upon expression by self-assembly.

Coat protein (CP) of cucumber mosaic virus (CMV): The term "coat protein (CP) of cucumber mosaic virus (CMV)", as used herein, refers to a coat protein of the cucumber mosaic virus which occurs in nature. Due to extremely wide host range of the cucumber mosaic virus, a lot of different strains and isolates of CMV are known and the sequences of the coat proteins of said strains and isolates have been determined and are, thus, known to the skilled person in the art as well. The sequences of said coat proteins (CPs) of CMV are described in and retrievable from the known databases such as Genbank, dpvweb.net, or ncbi.nlm.nih.gov/protein. Examples of described CPs of CMV are CAD92034.1, CD033961.2, AHZ89404.1, CD033963.1, ACN60036.1, CAC18660.1, CAC18661.1, CAC18658.1, CAC18657.1, CAC18659.1, AFS64321.1, AFS64320.1, ABG76792.1, CAI68015.1, AAQ22992.1, AEM36051.1, AEM36048.1, ADA77134.1, AIS22690.1, AGT15706.1, AFR44555.1, AHY22574.1, ACM89097.1, AAB07137.1, AAD17927.1, AAM81371.1, AAM81365.1, AAM81374.1, AAM81372.1, AAM81368.1, ABC18318.1, AAX70966.1, AAU14864.1, AHJ11230.1, AHJ11229.1, AHJ11228.1, O40980.1, CAB43510.1, Q66143.1, CAA77065.1, CAB77390.1, CAC18666.1, NP 040777.1, P16489.1, AGV39216.1, AGW51600.1, AGN56074.1, AGN56050.1, AGG16159.1, AGG16145.1, AGG16143.1, AFZ99011.1, 1407131A, CAA71834.1, CAA07411.1, CAC18665.1, Q66135.1, 1F15_A, O40983.1, Q00259.1, AER25350.1, AER25348.1, ADN84922.1, ABU95611.1, BAF93916.1, BAF93914.1, AAY46239.1, AAY46233.1, AAY46235.1, AAY46231.1, AAY46230.1, AAY46237.1, BAF45130.1, ABM46611.1, ABC00925.1, AAY42625.1, CAH25533.1, CAH25541.1, CAH25539.1, AAV63980.1, AAQ89596.1, AAQ89571.1, AAQ89570.1, AAQ83697.1, AAQ83689.1, AAK52423.1, CCN27449.1, CEF39516.1, CAE51926.1, CAC13146.1, BAM15840.1, AEK33396.1, ABY21417.1, ABM89156.1, CAI84629.1, AGA20617.1, AAO17725.1, CAD42338.1, AB018585.1, CDF77337.1, CAG25710.1, CAG25430.1, CAE30336.1, BAF45378.1, AAD17925.1, AGV39211.1, BAA07858.1, Q66141.1, O40981.1, ACB87210.1, CAI77626.1, CAH25521.1, ABG89138.1, AGT15712.1, AGT15703.1, A1I01134.1, AIC76579.1, AIC76576.1, AIC76574.1, AIC76573.1, AIB09173.1, AIB09172.1, ADF81043.1, ACQ99349.1, ACQ99348.1, CBF03403.1, CBF03405.1, CAX45872.1, CAX45871.1, ACH48048.1, AAG01451.1, AAA46409.1, AAD45249.1, AAG25053.1, AAA46410.1, AAA46411.1, AAA46412.1, ABB89052.1, AAY19285.1, AAW21981.1, AAW21983.1, AAA74483.1, AHL30195.1, BAA95601.1, Q00261.1, CAB89799.1, AGZ63887.1, BAN67666.1, AFZ62498.1, AFZ62495.1, AFZ62494.1, AGN56098.1, AGN56028.1, AGG16155.1, AGG16151.1, ACS83814.1, ACS83810.1, ACS83800.1, ACS83791.1, CCM80413.1, CCM80411.1, CCM80409.1, AFX68432.1, AFX68428.1, CAI39235.1, CAJ20021.1, CAE51924.1, AAS57946.1, Q66154.1, Q00260.1, CAA61802.1, P21368.1, BAB11693.1, AFV99523.1, AFV99515.1, AER25351.1, AFM56037.1, AFJ92022.1, AFH88687.1, AFC40207.1, BAL63166.1, AFA53169.1, AFA53167.1, BAL61194.1, AEU12505.1, AER35119.1, AEK86513.1, AEK69525.1, AEK69524.1, AEK33395.1, AEK33393.1, AEG79911.1, ADZ54767.1, ADZ54111.1, ADX86746.1, ADN84923.1, ACR14828.1, ACR14827.1, ABU62578.1, ACA13281.1, ABZ80826.1, ABY47903.1, ABY21424.1, ABY21420.1, ABY21419.1, ABY21418.1, ABY21413.1, ABX38992.1, ABV55389.1, ABV49618.1, AB018588.1, AB018589.1, ABN72590.1, ABN72591.1, ABN12319.1, ABN12316.1, BAF44939.1, ABM46612.1, CAJ15158.1, ABC00922.1, ABC00921.1, ABC00928.1, ABC00923.1, ABI94145.1, ABI94151.1, ABI94129.1, ABI94150.1, BAF33384.1, ABI93181.1, ABE68905.1, ABC00927.1, AAS48545.1, AAR89470.1, AAR23529.1, AAQ82698.1, AAM95241.1, AAM97677.1, AAK52977.1, AAW71967.1, ABJ55780.1, CAH17693.1, CAH17700.1, CAH17692.1, Q66140.1, ABM63376.1, AGT15704.1, CAB41491.1, AAR89478.1, CCJ09634.1, AEK69527.1, ACS83801.1, AIC76582.1, AHJ58884.1, AHJ11231.1, AGJ94707.1, ACS83798.1, ACS83793.1, ABK81652.1, AAS57945.1, AAN04483.1, AD066659.1, AAN17777.1, ADG26754.1, AFV99520.1, ABD73006.1, ACE07024.1, ABD64220.1, ABD72575.1, ABP87978.1, ABN13961.1, AAY85627.1, AGG16139.1, ACS83811.1, CAH17699.1, CAH17694.1, AFV69240.1, ACB56602.1, ADJ10637.1, ABM46614.1, AAY45749.1, AAA74484.1, CAH17697.1, ADA63484.1, ADA63482.1, ADA63480.1, Q83251.1, AIC76584.1, AIC76583.1, AAK27169.1, ABC00924.1, ACD62520.1, AB018591.1, AA062575.1, AAL48223.1, AIA99525.1, CAH17698.1, AAZ38725.1, AAF09246.2, CAH17701.1, ACB58305.1, AGG16158.1, CAH17695.1, AHJ58883.1, AEZ03836.1, BAB63959.1, ACD62519.1, BAF93912.1, AAZ78354.1, ACN38326.1, AFV99522.1, ADZ54109.1, CAA46151.1, AGV39213.1. Further examples of CMV coat proteins are provided in SEQ ID NOs 1-3.

It is noteworthy that these strains and isolates have highly similar coat protein sequences at different protein domains, including the N-terminus of the coat protein. In particular, 98.1% of all completely sequenced CMV isolates share more than 85% sequence identity within the first 28 amino acids of their coat protein sequence, and still 79.5% of all completely sequenced CMV isolates share more than 90% sequence identity within the first 28 amino acids of their coat protein sequence.

Typically and preferably, the coat protein of CMV used for the present invention is capable of forming a virus-like particle of CMV upon expression by self-assembly. Preferably, the coat protein of CMV used for the present invention is capable of forming a virus-like particle of CMV upon expression by self-assembly in *E. coli*.

SEQ ID NO. 1 corresponds to the amino acid sequence of the CP isolated and cloned from CMV-infected lily leaves collected from a private garden in Riga, Latvia. Thus, preferably, the term "coat protein of cucumber mosaic virus (CMV)", as used herein, refers to an amino acid sequence of a coat protein of CMV, wherein said amino acid sequence comprises, or preferably consists of, SEQ ID NO:1 or an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:1.

In a further very preferred embodiment, said coat protein of CMV is an amino acid sequence of a coat protein of CMV, wherein said amino acid sequence comprises SEQ ID NO:21 being the consecutive amino acids 2-27 of SEQ ID NO:1, or an amino acid sequence of a coat protein of CMV comprising an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:21. This is in particular preferred since the Th cell epitope preferably replaces a N-terminal region of the CMV polypeptide of the invention. A high sequence identity at the N-terminus of the CPs of the CMV to the one preferably used in the Examples, now ensures that proper assembly upon expression of the CPs can take place beside replacement of said N-terminal region by the typically aggregation-causing Th cell epitope.

In an again further very preferred embodiment, said coat protein of CMV is (a) an amino acid sequence of a coat protein of CMV, wherein said amino acid sequence comprises, or preferably consists of, SEQ ID NO:1 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:1; and wherein said amino sequence as defined in (a) or (b) comprises SEQ ID NO:21 being the consecutive amino acids 2-27 of SEQ ID NO: 1; or wherein said amino sequence as defined in (a) or (b) comprises an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:21.

Modified virus-like particle (VLP) of cucumber mosaic virus (CMV): The term "modified virus-like particle (VLP) of cucumber mosaic virus (CMV)" as used herein, refers to a VLP of CMV which is a modified one in such as it comprises, or preferably consists essentially of, or preferably consists of at least one modified CMV polypeptide, wherein said modified CMV polypeptide comprises, or preferably consists of, a CMV polypeptide, and a T helper cell epitope. Typically and preferably, said T helper cell epitope (i) is fused to the N-terminus of said CMV polypeptide, (ii) is fused to the C-terminus of said CMV polypeptide, (iii) replaces a region of consecutive amino acids of said CMV polypeptide, wherein the sequence identity between said replaced region of consecutive amino acids of said CMV polypeptide and the T helper cell epitope is at least 15%, preferably at least 20%, or (iv) replaces a N-terminal region of said CMV polypeptide, and wherein said replaced N-terminal region of said CMV polypeptide consists of 5 to 15 consecutive amino acids. Preferably, said T helper cell epitope replaces a N-terminal region of said CMV polypeptide, and wherein said replaced N-terminal region of said CMV polypeptide consists of 5 to 15 consecutive amino acids, preferably of 9 to 14 consecutive amino acids, more preferably of 11 to 13 consecutive amino acids, and most preferably of 11, 12 or 13 consecutive amino acids. Preferably said modified VLP of CMV of the present invention is a recombinant modified VLP of CMV.

Modified CMV polypeptide: The term "modified CMV polypeptide" as used herein refers to a CMV polypeptide modified in such as defined herein, that said modified CMV polypeptide comprises, or preferably consists of, a CMV polypeptide, and a T helper cell epitope. Typically, the modified CMV polypeptide is capable of forming a virus-like particle of CMV upon expression by self-assembly. Preferably, the modified CMV polypeptide is a recombinant modified CMV polypeptide and is capable of forming a virus-like particle of CMV upon expression by self-assembly in *E. coli*.

N-terminal region of the CMV polypeptide: The term "N-terminal region of the CMV polypeptide" as used herein, refers either to the N-terminus of said CMV polypeptide, and in particular to the N-terminus of a coat protein of CMV, or to the region of the N-terminus of said CMV polypeptide or said coat protein of CMV but starting with the second amino acid of the N-terminus of said CMV polypeptide or said coat protein of CMV if said CMV polypeptide or said coat protein comprises a N-terminal methionine residue. Preferably, in case said CMV polypeptide or said coat protein comprises a N-terminal methionine residue, from a practical point of view, the start-codon encoding methionine will usually be deleted and added to the N-terminus of the Th cell epitope. Further preferably, one, two or three additional amino acids, preferably one amino acid, may be optionally inserted between the stating methionine and the Th cell epitope for cloning purposes. The term "N-terminal region of the mutated amino acid sequence of a CMV polypeptide or a CMV coat protein" as used herein, refers either to the N-terminus of said mutated amino acid sequence of said CMV polypeptide or said coat protein of CMV, or to the region of the N-terminus of said mutated amino acid sequence of said CMV polypeptide or said coat protein of CMV but starting with the second amino acid of the N-terminus of said mutated amino acid sequence of said CMV polypeptide or said coat protein of CMV if said mutated amino acid sequence comprises a N-terminal methionine residue. Preferably, in case said CMV polypeptide or said coat protein comprises a N-terminal methionine residue, from a practical point of view, the start-codon encoding methionine will usually be deleted and added to the N-terminus of the Th cell epitope. Further preferably, one, two or three additional amino acids, preferably one amino acid, may be optionally inserted between the stating methionine and the Th cell epitope for cloning purposes.

Recombinant polypeptide: In the context of the invention the term "recombinant polypeptide" refers to a polypeptide which is obtained by a process which comprises at least one step of recombinant DNA technology. Typically and preferably, a recombinant polypeptide is produced in a prokaryotic expression system. It is apparent for the artisan that recombinantly produced polypeptides which are expressed in a prokaryotic expression system such as *E. coli* may comprise an N-terminal methionine residue. The N-terminal methionine residue is typically cleaved off the recombinant polypeptide in the expression host during the maturation of the recombinant polypeptide. However, the cleavage of the N-terminal methionine may be incomplete. Thus, a preparation of a recombinant polypeptide may comprise a mixture of otherwise identical polypeptides with and without an N-terminal methionine residue. Typically and preferably, a preparation of a recombinant polypeptide comprises less than 10%, more preferably less than 5%, and still more preferably less than 1% recombinant polypeptide with an N-terminal methionine residue.

Recombinant CMV polypeptide: The term "recombinant CMV polypeptide" refers to a CMV polypeptide as defined above which is obtained by a process which comprises at least one step of recombinant DNA technology. Typically and preferably a preparation of a recombinant CMV polypeptide comprises less than 10%, more preferably less than 5%, and still more preferably less than 1% recombinant CMV polypeptide with an N-terminal methionine residue. Consequently, a recombinant virus-like particle of the invention may comprise otherwise identical recombinant polypeptides with and without an N-terminal methionine residue.

Recombinant modified CMV polypeptide: The term "recombinant modified CMV polypeptide" refers to a modified CMV polypeptide as defined above which is obtained by a process which comprises at least one step of recombinant DNA technology. Typically and preferably a preparation of a recombinant modified CMV polypeptide comprises less than 10%, more preferably less than 5%, and still more preferably less than 1% recombinant modified CMV polypeptide with an N-terminal methionine residue. Consequently, a recombinant virus-like particle of the invention may comprise otherwise identical recombinant polypeptides with and without an N-terminal methionine residue.

Recombinant virus-like particle: In the context of the invention the term "recombinant virus-like particle" refers to a virus-like particle (VLP) which is obtained by a process which comprises at least one step of recombinant DNA technology. Typically and preferably, a recombinant virus-like particle comprises at least one recombinant polypeptide, preferably a recombinant CMV polypeptide or recombinant modified CMV polypeptide. Most preferably, a recombinant virus-like particle is composed of or consists of recombinant CMV polypeptides or recombinant modified CMV polypeptides. As a consequence, if in the context of the present invention the definition of inventive recombinant VLPs are effected with reference to specific amino acid sequences comprising a N-terminal methionine residue the scope of these inventive recombinant VLPs encompass the VLPs formed by said specific amino acid sequences without said N-terminal methionine residue but as well, even though typically in a minor amount as indicated herein, the VLPs formed by said specific amino acid sequences with said N-terminal methionine. Furthermore, it is within the scope of the present invention that if the definition of inventive recombinant VLPs are effected with reference to specific amino acid sequences comprising a N-terminal methionine residue VLPs are encompassed comprising both amino acid sequences comprising still said N-terminal methionine residue and amino acid sequences lacking the N-terminal methionine residue.

Mutated amino acid sequence: The term "mutated amino acid sequence" refers to an amino acid sequence which is obtained by introducing a defined set of mutations into an amino acid sequence to be mutated. In the context of the invention, said amino acid sequence to be mutated typically and preferably is an amino acid sequence of a coat protein of CMV. Thus, a mutated amino acid sequence differs from an amino acid sequence of a coat protein of CMV in at least one amino acid residue, wherein said mutated amino acid sequence and said amino acid sequence to be mutated show a sequence identity of at least 90%. Typically and preferably said mutated amino acid sequence and said amino acid sequence to be mutated show a sequence identity of at least 91%, 92%, 93% 94%, 95%, 96%, 97%, 98%, or 99%. Preferably, said mutated amino acid sequence and said sequence to be mutated differ in at most 11, 10, 9, 8, 7, 6, 4, 3, 2, or 1 amino acid residues, wherein further preferably said difference is selected from insertion, deletion and amino acid exchange. Preferably, the mutated amino acid sequence differs from an amino acid sequence of a coat protein of CMV in least one amino acid, wherein preferably said difference is an amino acid exchange.

Position corresponding to residues . . . : The position on an amino acid sequence, which is corresponding to given residues of another amino acid sequence can be identified by sequence alignment, typically and preferably by using the BLASTP algorithm, most preferably using the standard settings. Typical and preferred standard settings are: expect threshold: 10; word size: 3; max matches in a query range: 0; matrix: BLOSUM62; gap costs: existence 11, extension 1; compositional adjustments: conditional compositional score matrix adjustment.

Sequence identity: The sequence identity of two given amino acid sequences is determined based on an alignment of both sequences. Algorithms for the determination of sequence identity are available to the artisan. Preferably, the sequence identity of two amino acid sequences is determined using publicly available computer homology programs such as the "BLAST" program (blast.ncbi.nlm.nih-.gov/Blast.cgi) or the "CLUSTALW" (genome.jp/tools/clustalw/), and hereby preferably by the "BLAST" program provided on the NCBI homepage at blast.ncbi.nlm.nih.gov/Blast.cgi, using the default settings provided therein. Typical and preferred standard settings are: expect threshold: 10; word size: 3; max matches in a query range: 0; matrix: BLOSUM62; gap costs: existence 11, extension 1; compositional adjustments: conditional compositional score matrix adjustment.

Amino acid exchange: The term amino acid exchange refers to the exchange of a given amino acid residue in an amino acid sequence by any other amino acid residue having a different chemical structure, preferably by another proteinogenic amino acid residue. Thus, in contrast to insertion or deletion of an amino acid, the amino acid exchange does not change the total number of amino acids of said amino acid sequence. Very preferred in the context of the invention is the exchange of an amino acid residue of said amino acid sequence to be mutated by a lysine residue or by a cysteine residue.

Epitope: The term epitope refers to continuous or discontinuous portions of an antigen, preferably a polypeptide, wherein said portions can be specifically bound by an antibody or by a T-cell receptor within the context of an MHC molecule. With respect to antibodies, specific binding excludes non-specific binding but does not necessarily exclude cross-reactivity. An epitope typically comprise 5-20 amino acids in a spatial conformation which is unique to the antigenic site.

T helper (Th) cell epitope: The term "T helper (Th) cell epitope" as used herein refers to an epitope that is capable of recognition by a helper Th cell.

Universal Th cell epitope: The term "universal Th cell epitope" as used herein refers to a Th cell epitope that is capable of binding to at least one, preferably more than one MHC class II molecules. The simplest way to determine whether a peptide sequence is a universal Th cell epitope is to measure the ability of the peptide to bind to individual MHC class II molecules. This may be measured by the ability of the peptide to compete with the binding of a known Th cell epitope peptide to the MHC class II molecule. A representative selection of HLA-DR molecules are described in e.g. Alexander J, et al., Immunity (1994) 1:751-761. Affinities of Th cell epitopes for MHC class II molecules should be at least $10^{-5}$ M. An alternative, more tedious but also more relevant way to determine the "universality" of a Th cell epitope is the demonstration that a larger fraction of people (>30%) generate a measurable T cell response upon immunization and boosting one months later with a protein containing the Th cell epitope formulated in IFA. A representative collection of MHC class II molecules present in different individuals is given in Panina-Bordignon P, et al., Eur J Immunol (1989) 19:2237-2242. As a consequence, the term "universal Th cell epitope" as used herein preferably refers to a Th cell epitope that generates a measurable T cell response upon immunization and boosting (one months later with a protein containing the Th cell epitope formulated in IFA) in more than 30% of a selected group of individuals as described in Panina-Bordignon P, et al., Eur J Immunol (1989) 19:2237-2242. Moreover, and again further preferred, the term "universal Th cell epitope" as used herein preferably refers to a Th cell epitope that is capable of binding to at least one, preferably to at least two, and even more preferably to at least three DR alleles selected from of DR1, DR2w2b, DR3, DR4w4, DR4w14, DR5, DR7, DR52a, DRw53, DR2w2a; and preferably selected from DR1, DR2w2b, DR4w4, DR4w14, DR5, DR7, DRw53, DR2w2a, with an affinity at least 500 nM (as described in Alexander J, et al., Immunity (1994) 1:751-761 and references cited herein); a preferred binding assay to evaluate said affinities is the one described by Sette A, et al., J Immunol (1989) 142:35-40. In an even again more preferable manner, the term "universal Th cell epitope" as used herein refers to a Th cell epitope that is capable of binding to at least one, preferably to at least two, and even more preferably to at least three DR alleles selected from DR1, DR2w2b, DR4w4, DR4w14, DR5, DR7, DRw53, DR2w2a, with an affinity at least 500 nM (as described in Alexander J, et al., Immunity (1994) 1:751-761 and references cited herein); a preferred binding assay to evaluate said affinities is the one described by Sette A, et al., J Immunol (1989) 142:35-40.

Universal Th cell epitopes are described, and known to the skilled person in the art, such as by Alexander J, et al., Immunity (1994) 1:751-761, Panina-Bordignon P, et al., Eur J Immunol (1989) 19:2237-2242, Calvo-Calle J M, et al., J Immunol (1997) 159:1362-1373, and Valmori D, et al., J Immunol (1992) 149:717-721.

In a preferred embodiment of the present invention, the Th cell epitope is selected from HA 307-319 (SEQ ID NO:26), HBVnc 50-69 (SEQ ID NO:27), TT 830-843 (SEQ ID NO:4), CS 378-398 (SEQ ID NO:28), MT 17-31 (SEQ ID NO:29), TT 947-967 (SEQ ID NO:30) and PADRE (SEQ ID NO:5). In another preferred embodiment of the present invention, the universal Th cell epitope is selected from HA 307-319 (SEQ ID NO:26), HBVnc 50-69 (SEQ ID NO:27), TT 830-843 (SEQ ID NO:4), CS 378-398 (SEQ ID NO:28), MT 17-31 (SEQ ID NO:29), TT 947-967 (SEQ ID NO:30) and PADRE (SEQ ID NO:5). In a very preferred of the present invention, the Th cell epitope is TT 830-843 (SEQ ID NO:4) or PADRE (SEQ ID NO:5). In another very preferred embodiment of the present invention, the universal Th cell epitope is TT 830-843 (SEQ ID NO:4) or PADRE (SEQ ID NO:5). Therefore, in a very preferred embodiment, said Th cell epitope is TT 830-843 (SEQ ID NO:4). In another very preferred embodiment of the present invention, said Th cell epitope is PADRE (SEQ ID NO:5). In another very preferred embodiment, said universal Th cell epitope is TT 830-843 (SEQ ID NO:4). In another very preferred embodiment of the present invention, said universal Th cell epitope is PADRE (SEQ ID NO:5). The epitopes of SEQ ID NO:4 and SEQ ID NO:5 are known and even applications thereof have been described (Alexander J, et al., Immunity (1994) 1:751-761; Panina-Bordignon P, et al., Eur J Immunol (1989) 19:2237-2242; Valmori D, et al., J Immunol (1992) 149:717-721; Lanzavecchia A, et al. Eur J Immunol (1983) 13:733-738; Jemon K, et al., PLoS ONE (2013) 8(6): e66866; Jagu S, et al., PLoS ONE (2012) 8(1): e55538.

Coupling efficiency: The coupling efficiency of a virus-like particle with a specific antigen is determined by SDS-PAGE of the coupling reactions. The intensities of Coomassie Blue-stained bands corresponding to components of the coupling reaction are determined by densitometry and used to calculate coupling efficiency. Coupling efficiency is defined as the ratio of VLP polypeptide coupled to said antigen to the total amount of VLP polypeptide.

Adjuvant: The term "adjuvant" as used herein refers to non-specific stimulators of the immune response or substances that allow generation of a depot in the host which when combined with the vaccine and pharmaceutical composition, respectively, of the present invention may provide for an even more enhanced immune response. Preferred adjuvants are complete and incomplete Freund's adjuvant, aluminum containing adjuvant, preferably aluminum hydroxide, and modified muramyldipeptide. Further preferred adjuvants are mineral gels such as aluminum hydroxide, surface active substances such as lyso lecithin, pluronic polyols, polyanions, peptides, oil emulsions, keyhole limpet hemocyanins, dinitrophenol, and human adjuvants such as BCG (bacille Calmette Guerin) and *Corynebacterium parvum*. Such adjuvants are also well known in the art. Further adjuvants that can be administered with the compositions of the invention include, but are not limited to, Monophosphoryl lipid immunomodulator, AdjuVax 100a, QS-21, QS-18, CRL1005, Aluminum salts (Alum), MF-59, OM-174, OM-197, OM-294, and Virosomal adjuvant technology. The adjuvants may also comprise mixtures of these substances. Virus-like particles have been generally described as an adjuvant. However, the term "adjuvant", as used within the context of this application, refers to an adjuvant not being the inventive virus-like particle. Rather "adjuvant" relates to an additional, distinct component of the inventive compositions, vaccines or pharmaceutical compositions.

Antigen: As used herein, the term "antigen" refers to a molecule capable of being bound by an antibody or a T-cell receptor (TCR) if presented by MHC molecules. The term "antigen", as used herein, also refers to T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens. The polypeptide of the invention which is forming the inventive virus-like particles, may comprise the antigen. In particular, the inventive polypeptide may be a fusion product comprising the antigen. However, the term antigen does not encompass said mutated amino acid sequence which is comprised by said polypeptide. Typically and preferably, the term "antigen" as used herein does not encompass the virus-like particle according to the invention. Typically and preferably the term "antigen" rather refers to an additional component of the compositions, vaccines and pharmaceutical compositions of the invention having antigenic properties, wherein the antigen may be associated, bound, mixed with or linked to the virus-like particle by any means described herein.

Associated: The terms "associated" or "association" as used herein refer to all possible ways, preferably chemical interactions, by which two molecules are joined together. Chemical interactions include covalent and non-covalent interactions. Typical examples for non-covalent interactions are ionic interactions, hydrophobic interactions or hydrogen bonds, whereas covalent interactions are based, by way of example, on covalent bonds such as ester, ether, phosphoester, carbon-phosphorus bonds, carbon-sulfur bonds such as thioether, or imide bonds.

Attachment Site, First: As used herein, the phrase "first attachment site" refers to an element which is naturally occurring with the virus-like particle or which is artificially added to the virus-like particle, and to which the second attachment site may be linked. The first attachment site preferably is a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a chemically reactive group such as an amino group, a carboxyl group, a sulfhydryl group, a hydroxyl group, a guanidinyl group, histidinyl group, or a combination thereof. A preferred embodiment of a chemically reactive group being the first attachment site is the amino group of an amino acid residue, preferably of a lysine residue. The first attachment site is typically located on the surface, and preferably on the outer surface of the VLP. Multiple first attachment sites are present on the surface, preferably on the outer surface of the VLP, typically in a repetitive configuration. In a preferred embodiment the first attachment site is associated with the VLP, through at least one covalent bond, preferably through at least one peptide bond. In a further preferred embodiment the first attachment site is naturally occurring with the VLP. Alternatively, in a preferred embodiment the first attachment site is artificially added to the VLP. In a very preferred embodiment said first attachment site is the amino group of a lysine residue of the amino acid sequence of said VLP polypeptide.

Attachment Site, Second: As used herein, the phrase "second attachment site" refers to an element which is naturally occurring with or which is artificially added to the antigen and to which the first attachment site may be linked. The second attachment site of the antigen preferably is a protein, a polypeptide, a peptide, an amino acid, a sugar, a polynucleotide, a natural or synthetic polymer, a secondary metabolite or compound (biotin, fluorescein, retinol, digoxigenin, metal ions, phenylmethylsulfonylfluoride), or a chemically reactive group such as an amino group, a carboxyl group, a sulfhydryl group, a hydroxyl group, a guanidinyl group, histidinyl group, or a combination thereof. A preferred embodiment of a chemically reactive group being the second attachment site is a sulfhydryl group, preferably the sulfhydryl group of the amino acid cysteine most preferably the sulfhydryl group of a cysteine residue. The term "antigen with at least one second attachment site" refers, therefore, to a construct comprising the antigen and at least one second attachment site. However, in particular for a second attachment site, which is not naturally occurring within the antigen, such a construct typically and preferably further comprises a "linker". In another preferred embodiment the second attachment site is associated with the antigen through at least one covalent bond, preferably through at least one peptide bond. In a further embodiment, the second attachment site is naturally occurring within the antigen. In another further preferred embodiment, the second attachment site is artificially added to the antigen through a linker, wherein said linker comprises or alternatively consists of a cysteine. Preferably, the linker is fused to the antigen by a peptide bond.

Linked: The terms "linked" or "linkage" as used herein, refer to all possible ways, preferably chemical interactions, by which the at least one first attachment site and the at least one second attachment site are joined together. Chemical interactions include covalent and non-covalent interactions. Typical examples for non-covalent interactions are ionic interactions, hydrophobic interactions or hydrogen bonds, whereas covalent interactions are based, by way of example, on covalent bonds such as ester, ether, phosphoester, carbon-phosphorus bonds, carbon-sulfur bonds such as thioether, or imide bonds. In certain preferred embodiments the first attachment site and the second attachment site are linked through at least one covalent bond, preferably through at least one non-peptide bond, and even more preferably through exclusively non-peptide bond(s). The term "linked" as used herein, however, shall not only refer to a direct linkage of the at least one first attachment site and the at least one second attachment site but also, alternatively and preferably, an indirect linkage of the at least one first attachment site and the at least one second attachment site through intermediate molecule(s), and hereby typically and preferably by using at least one, preferably one, heterobifunctional cross-linker. In other preferred embodiments the first attachment site and the second attachment site are linked through at least one covalent bond, preferably through at least one peptide bond, and even more preferably through exclusively peptide bond(s).

Linker: A "linker", as used herein, either associates the second attachment site with the antigen or already comprises, essentially consists of, or consists of the second attachment site. Preferably, a "linker", as used herein, already comprises the second attachment site, typically and preferably—but not necessarily—as one amino acid residue, preferably as a cysteine residue. A preferred linkers are an amino acid linkers, i.e. linkers containing at least one amino acid residue. The term amino acid linker does not imply that such a linker consists exclusively of amino acid residues. However, a linker consisting exclusively of amino acid residues is a preferred embodiment of the invention. The amino acid residues of the linker are, preferably, composed of naturally occurring amino acids or unnatural amino acids known in the art, all-L or all-D or mixtures thereof. Further preferred embodiments of a linker in accordance with this invention are molecules comprising a sulfhydryl group or a cysteine residue and such molecules are, therefore, also encompassed within this invention. Further linkers useful for the present invention are molecules comprising a C1-C6 alkyl-, a cycloalkyl such as a cyclopentyl or cyclohexyl, a cycloalkenyl, aryl or heteroaryl moiety. Moreover, linkers comprising preferably a C1-C6 alkyl-, cycloalkyl-(C5, C6), aryl- or heteroaryl-moiety and additional amino acid(s) can also be used as linkers for the present invention and shall be encompassed within the scope of the invention. Association of the linker with the antigen is preferably by way of at least one covalent bond, more preferably by way of at least one peptide bond.

Ordered and repetitive antigen array: As used herein, the term "ordered and repetitive antigen array" refers to a repeating pattern of antigen which typically and preferably is characterized by a high order of uniformity in spacial arrangement of the antigens with respect to the VLP. In one embodiment of the invention, the repeating pattern may be a geometric pattern. Certain embodiments of the invention, such as antigens coupled to the inventive VLP, are typical and preferred examples of suitable ordered and repetitive antigen arrays which, moreover, possess strictly repetitive paracrystalline orders of antigens, preferably with spacing of 1 to 30 nanometers, preferably 2 to 15 nanometers, even more preferably 2 to 10 nanometers, even again more preferably 2 to 8 nanometers, and further more preferably 1.6 to 7 nanometers.

Fel d1 protein: The term "Fel d1 protein", as used herein, refers to a protein comprising or alternatively consisting of chain 1 of Fel d1 and chain 2 of Fel d1. Preferably chain 1 of Fel d1 and chain 2 of Fel d1 are linked covalently. In one preferred embodiment, the chain 1 of Fel d1 and chain 2 of Fel d1 are linked via at least one disulfide bond. In another preferred embodiment, the chain 1 and chain 2 are fused either directly or via a spacer, in which case said Fel d1 protein further comprises or alternatively consists of a spacer. Preferably the Fel d1 protein, as defined herein, consists of at most 300, even more preferably at most 200 amino acids in total. Typically and preferably, Fel d1 protein, according to the invention, is capable of inducing in vivo the production of antibody specifically binding to either the naturally occurring Fel d1 or the recombinant Fel d1 as produced according to EXAMPLE 8 of the present invention.

Chain 1 of Fel d1: The term "chain 1 of Fel d1", as used herein, refers to a polypeptide comprising or alternatively consisting of an amino acid sequence as of SEQ ID NO:37 or a homologous sequence thereof. The term "homologous sequence of SEQ ID NO:37", as used herein, refers to a polypeptide that has an identity to SEQ ID NO:37 which is greater than 80%, more preferably greater than 90%, and even more preferably greater than 95%. The term "chain 1 of Fel d1", as used herein, should also refer to a polypeptide encompassing at least one posttranslational modification, including but not limited to at least one glycosylation, of chain 1 of Fel d1, as defined herein. Preferably the chain 1 of Fel d1, as defined herein, consists of at most 130, even more preferably at most 100 amino acids in total.

Chain 2 of Fel d1: The term "chain 2 of Fel d1", as used herein, refers to a polypeptide comprising or alternatively consisting of an amino acid sequence as of SEQ ID NO:38, SEQ ID NO:39 or SEQ ID NO:40, or a homologous sequence thereof. The term "homologous sequence of SEQ ID NO:38, SEQ ID NO:39 or SEQ ID NO:40, as used herein, refers to a polypeptide that has an identity to SEQ ID NO:38, SEQ ID NO:39 or SEQ ID NO:40 which is greater than 80%, more preferably greater than 90%, and even more preferably greater than 95%. The term "chain 2 of Fel d1", as used herein, should also refer to a polypeptide encompassing at least one posttranslational modification, including but not limited to at least one glycosylation, of chain 2 of Fel d1, as defined herein Preferably the chain 2 of Fel d1, as defined herein, consists of at most 150, even more preferably at most 130, still more preferably at most 100 amino acids in total.

Immunostimulatory substance: As used herein, the term "immuno stimulatory substance" refers to a substance capable of inducing and/or enhancing an immune response. Immunostimulatory substances, as used herein, include, but are not limited to, toll-like receptor activating substances and substances inducing cytokine secretion. Toll-like receptor activating substances include, but are not limited to, immuno stimulatory nucleic acids, peptideoglycans, lipopolysaccharides, lipoteichonic acids, imidazoquinoline compounds, flagellins, lipoproteins, and immuno stimulatory organic substances such as taxol.

Immunostimulatory nucleic acid: As used herein, the term immuno stimulatory nucleic acid refers to a nucleic acid capable of inducing and/or enhancing an immune response. Immunostimulatory nucleic acids comprise ribonucleic acids and in particular desoxyribonucleic acids, wherein both, ribonucleic acids and desoxyribonucleic acids may be either double stranded or single stranded. Preferred ISS-NA are desoxyribonucleic acids, wherein further preferably said desoxyribonucleic acids are single stranded. Preferably, immunostimulatory nucleic acids contain at least one CpG motif comprising an unmethylated C. Very preferred immunostimulatory nucleic acids comprise at least one CpG motif, wherein said at least one CpG motif comprises or preferably consist of at least one, preferably one, CG dinucleotide, wherein the C is unmethylated. Preferably, but not necessarily, said CG dinucleotide is part of a palindromic sequence. The term immunostimulatory nucleic acid also refers to nucleic acids that contain modified bases, preferably 4-bromo-cytosine. Specifically preferred in the context of the invention are ISS-NA which are capable of stimulating IFN-alpha production in dendritic cells. Immunostimulatory nucleic acids useful for the purpose of the invention are described, for example, in WO2007/068747A1.

Oligonucleotide: As used herein, the term "oligonucleotide" refers to a nucleic acid sequence comprising 2 or more nucleotides, preferably about 6 to about 200 nucleotides, and more preferably 20 to about 100 nucleotides, and most preferably 20 to 40 nucleotides. Very preferably, oligonucleotides comprise about 30 nucleotides, more preferably oligonucleotides comprise exactly 30 nucleotides, and most preferably oligonucleotides consist of exactly 30 nucleotides. Oligonucleotides are polyribonucleotides or polydeoxribonucleotides and are preferably selected from (a) unmodified RNA or DNA, and (b) modified RNA or DNA. The modification may comprise the backbone or nucleotide analogues. Oligonucleotides are preferably selected from the group consisting of (a) single- and double-stranded DNA, (b) DNA that is a mixture of single- and double-stranded regions, (c) single- and double-stranded RNA, (d) RNA that is mixture of single- and double-stranded regions, and (e) hybrid molecules comprising DNA and RNA that are single-stranded or, more preferably, double-stranded or a mixture of single- and double-stranded regions. Preferred nucleotide modifications/analogs are selected from the group consisting of (a) peptide nucleic acid, (b) inosin, (c) tritylated bases, (d) phosphorothioates, (e) alkylphosphorothioates, (f) 5-nitroindole desoxyribofliranosyl, (g) 5-methyldesoxycytosine, and (h) 5,6-dihydro-5,6-dihydroxydesoxythymidine. Phosphothioated nucleotides are protected against degradation in a cell or an organism and are therefore preferred nucleotide modifications. Unmodified oligonucleotides consisting exclusively of phosphodiester bound nucleotides, typically are more active than modified nucleotides and are therefore generally preferred in the context of the invention. Most preferred are oligonucleotides consisting exclusively of phosphodiester bound deoxinucleotides, wherein further preferably said oligonucleotides are single stranded. Further preferred are oligonucleotides capable of stimulating IFN-alpha production in cells, preferably in dendritic cells. Very preferred oligonucleotides capable of stimulating IFN-alpha production in cells are selected from A-type CpGs and C-type CpGs. Further preferred are RNA-molecules without a Cap.

CpG motif: As used herein, the term "CpG motif refers to a pattern of nucleotides that includes an unmethylated central CpG, i.e. the unmethylated CpG dinucleotide, in which the C is unmethylated, surrounded by at least one base, preferably one or two nucleotides, flanking (on the 3' and the 5' side of) the central CpG. Typically and preferably, the CpG motif as used herein, comprises or alternatively consists of the unmethylated CpG dinucleotide and two nucleotides on its 5' and 3' ends. Without being bound by theory, the bases flanking the CpG confer a significant part of the activity to the CpG oligonucleotide.

Unmethylated CpG-containing oligonucleotide: As used herein, the term "unmethylated CpG-containing oligonucleotide" or "CpG" refers to an oligonucleotide, preferably to an oligodesoxynucleotide, containing at least one CpG motif. Thus, a CpG contains at least one unmethylated cytosine, guanine dinucleotide. Preferred CpGs stimulate/activate, e.g. have a mitogenic effect on, or induce or increase cytokine expression by, a vertebrate bone marrow derived cell. For example, CpGs can be useful in activating B cells, NK cells and antigen-presenting cells, such as dendritic cells, monocytes and macrophages. Preferably, CpG relates to an oligodesoxynucleotide, preferably to a single stranded oligodesoxynucleotide, containing an unmethylated cytosine followed 3' by a guanosine, wherein said unmethylated cytosine and said guanosine are linked by a phosphate bond, wherein preferably said phosphate bound is a phosphodiester bound or a phosphothioate bound, and wherein further preferably said phosphate bond is a phosphodiester bound. CpGs can include nucleotide analogs such as analogs containing phosphorothio ester bonds and can be double-stranded or single-stranded. Generally, double-stranded molecules are more stable in vivo, while single-stranded molecules have increased immune activity. Preferably, as used herein, a CpG is an oligonucleotide that is at least about ten nucleotides in length and comprises at least one CpG motif, wherein further preferably said CpG is 10 to 60, more preferably 15 to 50, still more preferably 20 to 40, still more preferably about 30, and most preferably exactly 30 nucleotides in length. A CpG may consist of methylated and/or unmethylated nucleotides, wherein said at least one CpG motif comprises at least one CG dinucleotide wherein the C is unmethylated. The CpG may also comprise methylated and unmethylated sequence stretches, wherein said at least one CpG motif comprises at least one CG dinucleotide wherein the C is unmethylated. Very preferably, CpG relates to a single stranded oligodesoxynucleotide containing an unmethylated cytosine followed 3' by a guanosine, wherein said unmethylated cytosine and said guanosine are linked by a phosphodiester bound. The CpGs can include nucleotide analogs such as analogs containing phosphorothioester bonds and can be double-stranded or single-stranded. Generally, phosphodiester CpGs are A-type CpGs as indicated below, while phosphothioester stabilized CpGs are B-type CpGs. Preferred CpG oligonucleotides in the context of the invention are A-type CpGs.

A-type CpG: As used herein, the term "A-type CpG" or "D-type CpG" refers to an oligodesoxynucleotide (ODN) comprising at least one CpG motif. A-type CpGs preferentially stimulate activation of T cells and the maturation of dendritic cells and are capable of stimulating IFN-alpha production. In A-type CpGs, the nucleotides of the at least one CpG motif are linked by at least one phosphodiester bond. A-type CpGs comprise at least one phosphodiester bond CpG motif which may be flanked at its 5' end and/or, preferably and, at its 3' end by phosphorothioate bound nucleotides. Preferably, the CpG motif, and hereby preferably the CG dinucleotide and its immediate flanking regions comprising at least one, preferably two nucleotides, are composed of phosphodiester nucleotides. Preferred A-type CpGs exclusively consist of phosphodiester (PO) bond nucleotides. Typically and preferably, the poly G motif comprises or alternatively consists of at least one, preferably at least three, at least 4, 5, 6, 7, 8, 9, 10, 11, 12, 13, 14, or 15 Gs (guanosines), most preferably by at least 10 Gs. Preferably, the A-type CpG of the invention comprises or alternatively consists of a palindromic sequence.

Virus-like particle (VLP): The term virus-like particle as used herein, refers to a non-replicative or non-infectious, preferably a non-replicative and non-infectious virus particle, or refers to a non-replicative or non-infectious, preferably a non-replicative and noninfectious structure resembling a virus particle, preferably a capsid of a virus. The term "non-replicative", as used herein, refers to being incapable of replicating the genome comprised by the VLP. The term "non-infectious", as used herein, refers to being incapable of entering the host cell. A virus-like particle in accordance with the invention is non-replicative and noninfectious since it lacks all or part of the viral genome or genome function. A virus-like particle in accordance with the invention may contain nucleic acid distinct from their genome. Recombinantly produced virus-like particles typically contain host cell derived RNA. A typical and preferred embodiment of a virus-like particle in accordance with the present invention is a viral capsid composed of polypeptides of the invention. A virus-like particle is a macro molecular assembly composed of viral coat protein which typically comprises 60, 120, 180, 240, 300, 360, or more than 360 protein subunits per virus-like particle. Typically and preferably, the interactions of these subunits lead to the formation of viral capsid or viral-capsid like structure with an inherent repetitive organization. One feature of a virus-like particle is its highly ordered and repetitive arrangement of its subunits. Virus-like particles comprising more than one species of polypeptides, often referred to as mosaic VLPs are also encompassed by the invention. Thus, in one embodiment, the virus-like particle according to the invention comprises at least two different species of polypeptides, wherein at least one of said species of polypeptides is a VLP-polypeptide containing a pan Th cell epitope.

Packaged: The term "packaged" as used herein refers to the state of a polyanionic macromolecule or immunostimulatory substances in relation to the VLP. The term "packaged" as used herein includes binding that may be covalent, e.g., by chemically coupling, or non-covalent, e.g., ionic interactions, hydrophobic interactions, hydrogen bonds, etc. The term also includes the enclosement, or partial enclosement, of a polyanionic macromolecule. Thus, the polyanionic macromolecule or immunostimulatory substances can be enclosed by the VLP without the existence of an actual binding, in particular of a covalent binding. In preferred embodiments, the at least one polyanionic macromolecule or immunostimulatory substances is packaged inside the VLP, most preferably in a non-covalent manner. In case said immunostimulatory substances is nucleic acid, preferably a DNA, the term packaged implies that said nucleic acid is not accessible to nucleases hydrolysis, preferably not accessible to DNAse hydrolysis (e.g. DNaseI or Benzonase), wherein preferably said accessibility is assayed as described in Examples 11-17 of WO2003/024481A2.

The present invention provides virus-like particles of plant virus Cucumber Mosaic Virus (CMV), and in particular modified VLPs of CMV comprising Th cell epitopes, in particular universal Th cell epitopes.

Thus in a first aspect, the present invention provides for a modified virus-like particle (VLP) of cucumber mosaic virus (CMV), wherein said modified VLP of CMV comprises, essentially consists of, or alternatively consists of, at least one modified CMV polypeptide, wherein said modified CMV polypeptide comprises, or preferably consists of, (a) a CMV polypeptide, and (b) a T helper cell epitope; and wherein said CMV polypeptide comprises, or preferably consists of, (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%.

In a preferred embodiment, said CMV polypeptide comprises, preferably consists of, an amino acid sequence of a coat protein of CMV. In an alternative embodiment, said CMV polypeptide comprises, preferably consists of a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%; wherein preferably said mutated amino acid sequence and said amino acid sequence to be mutated differ in least one and in at most 11, 10, 9, 8, 7, 6, 5, 4, 3, or 2 amino acid residues, and wherein further preferably these differences are selected from (i) insertion, (ii) deletion, (iii) amino acid exchange, and (iv) any combination of (i) to (iii). Mutations may be introduced into an amino acid sequence to be mutated in order to modify certain features of the virus-like particles such as stability and/or coupling efficiency. Introducing cysteine residues may enhance stability of cysteine bridges are formed between subunits and introduction of lysines into the surface of VLPs may enhance coupling efficiencies.

In another preferred embodiment, said CMV polypeptide comprises, or preferably consists of, (i) (a) an amino acid sequence of a coat protein of CMV, wherein said amino acid sequence comprises, or preferably consists of, SEQ ID NO:1 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:1; or (ii) a mutated amino acid sequence, wherein said amino acid sequence to be mutated is said amino acid sequence as defined in (i) of this claim, and wherein said mutated amino acid sequence and said amino acid sequence to be mutated show a sequence identity of at least 95%, preferably of at least 98%, and more preferably of at least 99%.

In a very preferred embodiment, said CMV polypeptide comprises, or preferably consists of, (a) an amino acid sequence of a coat protein of CMV, wherein said amino acid sequence comprises, or preferably consists of, SEQ ID NO:1 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:1.

In another preferred embodiment, said CMV polypeptide comprises, or preferably consists of, (i) (a) an amino acid sequence of a coat protein of CMV, wherein said amino acid sequence comprises SEQ ID NO:21, or (b) an amino acid sequence of a coat protein of CMV comprising an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:21; or (ii) a mutated amino acid sequence, wherein said amino acid sequence to be mutated is said amino acid sequence as defined in (i) of this claim, and wherein said mutated amino acid sequence and said amino acid sequence to be mutated show a sequence identity of at least 95%, preferably of at least 98%, and more preferably of at least 99%.

In another very preferred embodiment, said CMV polypeptide comprises, or preferably consists of, (a) an amino acid sequence of a coat protein of CMV, wherein said amino acid sequence comprises SEQ ID NO:21, or (b) an amino acid sequence of a coat protein of CMV comprising an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:21.

In again another preferred embodiment, said CMV polypeptide comprises, or preferably consists of, (i) (a) an amino acid sequence of a coat protein of CMV, wherein said amino acid sequence comprises, or preferably consists of, SEQ ID NO:1 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:1; and wherein said amino acid sequence as defined in (a) or (b) in this claim comprises SEQ ID NO:21; or wherein said amino acid sequence as defined in (a) or (b) in this claim comprises an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:21; or (ii) a mutated amino acid sequence, wherein said amino acid sequence to be mutated is said amino acid sequence as defined in (i) of this claim, and wherein said mutated amino acid sequence and said amino acid sequence to be mutated show a sequence identity of at least 98% preferably of at least 99%.

In again another very preferred embodiment, said CMV polypeptide comprises, or preferably consists of, (a) an amino acid sequence of a coat protein of CMV, wherein said amino acid sequence comprises, or preferably consists of, SEQ ID NO:1 or (b) an amino acid sequence having a sequence identity of at least 90% of SEQ ID NO:1; and wherein said amino acid sequence as defined in (a) or (b) in this claim comprises SEQ ID NO:21; or wherein said amino sequence as defined in (a) or (b) in this claim comprises an amino acid sequence region, wherein said amino acid sequence region has a sequence identity of at least 90% with SEQ ID NO:21.

Typically and preferably, said T helper cell epitope (i) is fused to the N-terminus of said CMV polypeptide, (ii) is fused to the C-terminus of said CMV polypeptide, (iii) replaces a region of consecutive amino acids of said CMV polypeptide, wherein the sequence identity between said replaced region of consecutive amino acids of said CMV polypeptide and the T helper cell epitope is at least 15%, preferably at least 20%, or (iv) replaces a N-terminal region of said CMV polypeptide, and wherein said replaced N-terminal region of said CMV polypeptide consists of 5 to 15 consecutive amino acids.

In a preferred embodiment, said T helper cell epitope replaces a N-terminal region of said CMV polypeptide, wherein preferably the number of amino acids of said N-terminal region replaced is equal to or lower than the number of amino acids of which said T helper cell epitope consists. In other words, said N-terminal region of said CMV polypeptide consists of a first number of amino acids and the Th cell epitope consists of a second number of amino acids, and in a preferred embodiment, said first number of amino acids is equal to or lower than the second number of amino acids.

In a further preferred embodiment, said replaced N-terminal region of said CMV polypeptide consists of 5 to 15 consecutive amino acids, preferably of 9 to 14 consecutive amino acids, more preferably of 11 to 13 consecutive amino acids. In a very preferred embodiment, said N-terminal region of said CMV polypeptide corresponds to amino acids 2-12 of SEQ ID NO:1.

Thus, in a very preferred embodiment, said CMV polypeptide comprises, or preferably consists of, (i) (a) an amino acid sequence of a coat protein of CMV, wherein said amino acid sequence comprises, or preferably consists of, SEQ ID NO:1 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:1; or (ii) a mutated amino acid sequence, wherein said amino acid sequence to be mutated is said amino acid sequence as defined in (i) of this claim, and wherein said mutated amino acid sequence and said amino acid sequence to be mutated show a sequence identity of at least 95%, preferably of at least 98%, and more preferably of at least 99%, and wherein said T helper cell epitope replaces a N-terminal region of said CMV polypeptide, wherein preferably the number of amino acids of said N-terminal region replaced is equal to or lower than the number of amino acids of which said T helper cell epitope consists.

Thus, in a very preferred embodiment, said CMV polypeptide comprises, or preferably consists of, (i) (a) an amino acid sequence of a coat protein of CMV, wherein said amino acid sequence comprises, or preferably consists of, SEQ ID NO:1 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:1; or (ii) a mutated amino acid sequence, wherein said amino acid sequence to be mutated is said amino acid sequence as defined in (i) of this claim, and wherein said mutated amino acid sequence and said amino acid sequence to be mutated show a sequence identity of at least 95%, preferably of at least 98%, and more preferably of at least 99%, wherein said T helper cell epitope replaces a N-terminal region of said CMV polypeptide, and wherein said replaced N-terminal region of said CMV polypeptide consists of 5 to 15 consecutive amino acids, preferably of 9 to 14 consecutive amino acids, more preferably of 11 to 13 consecutive amino acids.

Thus, in a very preferred embodiment, said CMV polypeptide comprises, or preferably consists of, (i) (a) an amino acid sequence of a coat protein of CMV, wherein said amino acid sequence comprises, or preferably consists of, SEQ ID NO:1 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:1; or (ii) a mutated amino acid sequence, wherein said amino acid sequence to be mutated is said amino acid sequence as defined in (i) of this claim, and wherein said mutated amino acid sequence and said amino acid sequence to be mutated show a sequence identity of at least 95%, preferably of at least 98%, and more preferably of at least 99%, wherein said T helper cell epitope replaces a N-terminal region of said CMV polypeptide, and wherein said N-terminal region of said CMV polypeptide corresponds to amino acids 2-12 of SEQ ID NO:1.

Thus, in a very preferred embodiment, said CMV polypeptide comprises, or preferably consists of, (a) an amino acid sequence of a coat protein of CMV, wherein said amino acid sequence comprises, or preferably consists of, SEQ ID NO:1 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:1, and wherein said T helper cell epitope replaces a N-terminal region of said CMV polypeptide, wherein preferably the number of amino acids of said N-terminal region replaced is equal to or lower than the number of amino acids of which said T helper cell epitope consists. Thus, in a very preferred embodiment, said CMV polypeptide comprises, or preferably consists of, (a) an amino acid sequence of a coat protein of CMV, wherein said amino acid sequence comprises, or preferably consists of, SEQ ID NO:1 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:1, wherein said T helper cell epitope replaces a N-terminal region of said CMV polypeptide, and wherein said replaced N-terminal region of said CMV polypeptide consists of 5 to 15 consecutive amino acids, preferably of 9 to 14 consecutive amino acids, more preferably of 11 to 13 consecutive amino acids.

Thus, in a very preferred embodiment, said CMV polypeptide comprises, or preferably consists of, (a) an amino acid sequence of a coat protein of CMV, wherein said amino acid sequence comprises, or preferably consists of, SEQ ID NO:1 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:1, wherein said T helper cell epitope replaces a N-terminal region of said CMV polypeptide, and wherein said N-terminal region of said CMV polypeptide corresponds to amino acids 2-12 of SEQ ID NO:1.

Thus, in a very preferred embodiment, said CMV polypeptide comprises, or preferably consists of, (a) an amino acid sequence of a coat protein of CMV, wherein said amino acid sequence comprises SEQ ID NO:21, or (b) an amino acid sequence of a coat protein of CMV comprising an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:21, and wherein said T helper cell epitope replaces a N-terminal region of said CMV polypeptide, wherein preferably the number of amino acids of said N-terminal region replaced is equal to or lower than the number of amino acids of which said T helper cell epitope consists.

Thus, in a very preferred embodiment, said CMV polypeptide comprises, or preferably consists of, (a) an amino acid sequence of a coat protein of CMV, wherein said amino acid sequence comprises SEQ ID NO:21, or (b) an amino acid sequence of a coat protein of CMV comprising an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:21, wherein said T helper cell epitope replaces a N-terminal region of said CMV polypeptide, and wherein said replaced N-terminal region of said CMV polypeptide consists of 5 to 15 consecutive amino acids, preferably of 9 to 14 consecutive amino acids, more preferably of 11 to 13 consecutive amino acids.

Thus, in a very preferred embodiment, said CMV polypeptide comprises, or preferably consists of, (a) an amino acid sequence of a coat protein of CMV, wherein said amino acid sequence comprises SEQ ID NO:21, or (b) an amino acid sequence of a coat protein of CMV comprising an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:21, wherein said T helper cell epitope replaces a N-terminal region of said CMV polypeptide, and wherein said N-terminal region of said CMV polypeptide corresponds to amino acids 2-12 of SEQ ID NO:1.

Thus, in a very preferred embodiment, said CMV polypeptide comprises, or preferably consists of, (a) an amino acid sequence of a coat protein of CMV, wherein said amino acid sequence comprises, or preferably consists of, SEQ ID NO:1 or (b) an amino acid sequence having a sequence identity of at least 90% of SEQ ID NO:1; and wherein said amino sequence as defined in (a) or (b) in this claim comprises SEQ ID NO:21; or wherein said amino sequence as defined in (a) or (b) in this claim comprises an amino acid sequence region, wherein said amino acid sequence region has a sequence identity of at least 90% with SEQ ID NO:21, and wherein said T helper cell epitope replaces a N-terminal region of said CMV polypeptide, wherein preferably the number of amino acids of said N-terminal region replaced is equal to or lower than the number of amino acids of which said T helper cell epitope consists.

Thus, in a very preferred embodiment, said CMV polypeptide comprises, or preferably consists of, (a) an amino acid sequence of a coat protein of CMV, wherein said amino acid sequence comprises, or preferably consists of, SEQ ID NO:1 or (b) an amino acid sequence having a sequence identity of at least 90% of SEQ ID NO:1; and wherein said amino sequence as defined in (a) or (b) in this claim comprises SEQ ID NO:21; or wherein said amino sequence as defined in (a) or (b) in this claim comprises an amino acid sequence region, wherein said amino acid sequence region has a sequence identity of at least 90% with SEQ ID NO:21, wherein said T helper cell epitope replaces a N-terminal region of said CMV polypeptide, and wherein said replaced N-terminal region of said CMV polypeptide consists of 5 to 15 consecutive amino acids, preferably of 9 to 14 consecutive amino acids, more preferably of 11 to 13 consecutive amino acids.

Thus, in a very preferred embodiment, said CMV polypeptide comprises, or preferably consists of, (a) an amino acid sequence of a coat protein of CMV, wherein said amino acid sequence comprises, or preferably consists of, SEQ ID NO:1 or (b) an amino acid sequence having a sequence identity of at least 90% of SEQ ID NO:1; and wherein said amino sequence as defined in (a) or (b) in this claim comprises SEQ ID NO:21; or wherein said amino sequence as defined in (a) or (b) in this claim comprises an amino acid sequence region, wherein said amino acid sequence region has a sequence identity of at least 90% with SEQ ID NO:21, wherein said T helper cell epitope replaces a N-terminal region of said CMV polypeptide, and wherein said N-terminal region of said CMV polypeptide corresponds to amino acids 2-12 of SEQ ID NO:1.

Very preferably, said T helper cell epitope is a universal T helper cell epitope, wherein preferably said T helper cell epitope consists of at most 20 amino acids.

In a further preferred embodiment, said Th cell epitope is a PADRE sequence. In again further preferred embodiment, said Th cell epitope, comprises, preferably consists of, the amino acid sequence of SEQ ID NO:5.

In another preferred embodiment, said T helper cell epitope is derived from a human vaccine. Preferably said Th cell epitope is derived from tetanus toxin. Again preferably, said Th cell epitope has, preferably consists of, the amino acid sequence of SEQ ID NO:4.

In a very preferred embodiment of the present invention, said CMV polypeptide comprises, or preferably consists of, an amino acid sequence of a coat protein of CMV, wherein said amino acid sequence comprises, or preferably consists of, SEQ ID NO:1 or an amino acid sequence having a sequence identity of at least 95% of SEQ ID NO:1; and wherein said amino sequence comprises SEQ ID NO:21, and wherein said T helper cell epitope replaces the N-terminal region of said CMV polypeptide, and wherein said replaced N-terminal region of said CMV polypeptide consists of 11 to 13 consecutive amino acids, preferably of 11 consecutive amino acids, and wherein further preferably said N-terminal region of said CMV polypeptide corresponds to amino acids 2-12 of SEQ ID NO:1.

In another very preferred embodiment, said modified CMV polypeptide comprises, preferably consists of, an amino acid sequence of SEQ ID NO:6. In a further very preferred embodiment, said modified CMV polypeptide comprises, preferably consists of, an amino acid sequence of SEQ ID NO:7.

The VLPs of the invention may be expressed in prokaryotic or eukaryotic expression systems. Preferred systems are *E. coli*, yeast, insect cells as well as mammalian cell lines. Very preferred said modified VLP of CMV or said VLP of CMV is obtained by expression of said modified CMV polypeptide or said CMV polypeptide in *E. coli*, and wherein preferably said expression is effected at temperatures of between 10° C. to 25° C., preferably at a temperature of 20° C. As indicated above, recombinantly produced polypeptides may comprise an N-terminal methionine residue. In one embodiment said CMV polypeptide or modified CMV polypeptide therefore comprises an N-terminal methionine residue. However, typically and preferably said N-terminal methionine residue is cleaved off said CMV polypeptide or said modified CMV polypeptide.

Therefore, in another aspect, the present invention provides for a virus-like particle (VLP) of cucumber mosaic virus (CMV), wherein said VLP of CMV comprises, essentially consists of, or alternatively consists of, at least one CMV polypeptide comprising or preferably consisting of: (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said a coat protein of CMV show a sequence identity of at least 90%, preferably of at least 95%, further preferably of at least 98% and again more preferably of at least 99%; and wherein said VLP of CMV is obtained by expression of said CMV polypeptide in *E. coli*, and wherein preferably said expression is effected at temperatures of between 10° C. to 25° C., preferably at a temperature of 20° C.

The invention encompasses compositions wherein said VLPs of the invention, comprise any one of the technical features as described herein, either alone or in any possible combination.

In a further aspect, the present invention provides for a composition comprising a modified virus-like particle. Furthermore, these modified VLPs serve as, preferably, vaccine platform, for generating immune responses, in particular antibody responses, against antigens linked to said modified VLPs. The presence of the Th cell epitopes, in particular universal Th cell epitopes, led to a further increase in the generated immune response.

Thus, in a further preferred embodiment said composition comprises (a) at least one modified virus-like particle of the invention, wherein said modified virus-like particle comprises at least one first attachment site; and (b) at least one antigen, wherein said antigen comprises at least one second attachment site; wherein (a) and (b) are linked through said at least one first and said at least one second attachment site. Methods for linking said modified virus-like particle and said antigen via said first and said second attachment site are described, for example, in WO2002/056905A2 and WO2004/084940A1.

In a further preferred embodiment, said first attachment site is linked to said second attachment site via at least one covalent bond. In a further preferred embodiment, said first attachment site and said second attachment site are linked via at least one covalent peptide-bond In a further preferred embodiment, said covalent bond is a non-peptide bond. Thus, in again another preferred embodiment, said first attachment site and said second attachment site are linked via at least one covalent non-peptide-bond. In a further preferred embodiment said first attachment site is an amino group, preferably an amino group of a lysine.

Attachment between modified virus-like particles and antigens by way of disulfide bonds are labile, in particular, to sulfhydryl-moiety containing molecules, and are, furthermore, less stable in serum than, for example, thioether attachments (Martin F J. and Papahadjopoulos D. (1982) J. Biol. Chem. 257: 286-288). Therefore, in a further very preferred embodiment of the present invention, the association or linkage of the modified VLP and the at least one antigen does not comprise a disulfide bond. Further preferred hereby, the at least one second attachment comprise, or preferably is, a sulfhydryl group. Moreover, the association or linkage of the modified VLP and the at least one antigen does preferably not comprise a sulphur-sulphur bond. Further preferred hereby, the at least one second attachment comprise, or preferably is, a sulfhydryl group. In a further very preferred embodiment, said at least one first attachment site is not or does not comprise a sulfhydryl group. In again a further very preferred embodiment, said at least one first attachment site is not or does not comprise a sulfhydryl group of a cysteine. In a further preferred embodiment said second attachment site is a sulfhydryl group, preferably a sulfhydryl group of a cysteine.

In a very preferred embodiment, the at least one first attachment site is an amino group, preferably an amino group of a lysine residue and the at least one second attachment site is a sulfhydryl group, preferably a sulfhydryl group of a cysteine residue or a sulfhydryl group that has been chemically attached to the antigen. In a further preferred embodiment only one of said second attachment sites associates with said first attachment site through at least one non-peptide covalent bond leading to a single and uniform type of binding of said antigen to said modified virus-like particle, wherein said only one second attachment site that associates with said first attachment site is a sulfhydryl group, and wherein said antigen and said modified virus-like particle interact through said association to form an ordered and repetitive antigen array.

In one preferred embodiment of the invention, the antigen is linked to the modified VLP by way of chemical cross-linking, typically and preferably by using a heterobifunctional cross-linker. In preferred embodiments, the heterobifunctional cross-linker contains a functional group which can react with the preferred first attachment sites, preferably with the amino group, more preferably with the amino groups of lysine residue(s) of the modified VLP, and a further functional group which can react with the preferred second attachment site, i.e. a sulfhydryl group, preferably of cysteine(s) residue inherent of, or artificially added to the antigen, and optionally also made available for reaction by reduction. Several hetero-bifunctional cross-linkers are known to the art. These include the preferred cross-linkers SMPH (Pierce), Sulfo-MBS, Sulfo-EMCS, Sulfo-GMBS, Sulfo-SIAB, Sulfo-SMPB, Sulfo-SMCC, Sulfo-KMUS SVSB, SIA, and other cross-linkers available for example from the Pierce Chemical Company, and having one functional group reactive towards amino groups and one functional group reactive towards sulfhydryl groups. The above mentioned cross-linkers all lead to formation of an amide bond after reaction with the amino group and a thioether linkage with the sulfhydryl groups. Another class of cross-linkers suitable in the practice of the invention is characterized by the introduction of a disulfide linkage between the antigen and the modified VLP upon coupling. Preferred cross-linkers belonging to this class include, for example, SPDP and Sulfo-LC-SPDP (Pierce).

Linking of the antigen to the modified VLP by using a hetero-bifunctional cross-linker according to the preferred methods described above, allows coupling of the antigen to the modified VLP in an oriented fashion. Other methods of linking the antigen to the modified VLP include methods wherein the antigen is cross-linked to the modified VLP, using the carbodiimide EDC, and NHS. The antigen may also be first thiolated through reaction, for example with SATA, SATP or iminothiolane. The antigen, after deprotection if required, may then be coupled to the modified VLP as follows. After separation of the excess thiolation reagent, the antigen is reacted with the modified VLP, previously activated with a hetero-bifunctional cross-linker comprising a cysteine reactive moiety, and therefore displaying at least one or several functional groups reactive towards cysteine residues, to which the thiolated antigen can react, such as described above. Optionally, low amounts of a reducing agent are included in the reaction mixture. In further methods, the antigen is attached to the modified VLP, using a homo-bifunctional cross-linker such as glutaraldehyde, DSG, BM[PEO]4, BS3, (Pierce) or other known homo-bifunctional cross-linkers with functional groups reactive towards amine groups or carboxyl groups of the modified VLP.

In very preferred embodiments of the invention, the antigen is linked via a cysteine residue, having been added to either the N-terminus or the C-terminus of, or a natural cysteine residue within the antigen, to lysine residues of the modified virus-like particle. In a preferred embodiment, the composition of the invention further comprises a linker, wherein said linker associates said antigen with said second attachment site, and wherein preferably said linker comprises or alternatively consists of said second attachment site.

Engineering of a second attachment site onto the antigen is achieved by the association of a linker, preferably containing at least one amino acid suitable as second attachment site according to the disclosures of this invention. Therefore, in a preferred embodiment of the present invention, a linker is associated to the antigen by way of at least one covalent bond, preferably, by at least one, preferably one peptide bond. Preferably, the linker comprises, or alternatively consists of, the second attachment site. In a further preferred embodiment, the linker comprises a sulfhydryl group, preferably of a cysteine residue. In another preferred embodiment, the amino acid linker is a cysteine residue.

The selection of a linker will be dependent on the nature of the antigen, on its biochemical properties, such as pi, charge distribution and glycosylation. In general, flexible amino acid linkers are favored. In a further preferred embodiment of the present invention, the linker consists of amino acids, wherein further preferably the linker consists of at least one and at most 25, preferably at most 20, more preferably at most 15 amino acids. In an again preferred embodiment of the invention, the amino acid linker contains 1 to 10 amino acids. In a further preferred embodiment said linker comprises or alternatively consists of said second attachment site.

In a further preferred embodiment said linker is an amino acid linker, and wherein preferably said amino acid linker is selected from the group consisting of: (a) CGG; (b) N-terminal gamma 1-linker; (c) N-terminal gamma 3-linker; (d) Ig hinge regions; (e) N-terminal glycine linkers; (f) (G)kC(G)n with n=0-12 and k=0-5; (g) N-terminal glycine-serine linkers (h) (G)kC(G)m(S)l(GGGGS)n with n=0-3, k=0-5, m=0-10, l=0-2; (i) GGC; (j) GGC-NH2; (k) C-terminal gamma 1-linker; (l) C-terminal gamma 3-linker; (m) C-terminal glycine linkers; (n) (G)nC(G)k with n=0-12 and k=0-5; (o) C-terminal glycine-serine linkers; and (p) (G)m(S)l(GGGGS)n(G)oC(G)k with n=0-3, k=0-5, m=0-10, l=0-2, and o=0-8. In general, glycine residues will be inserted between bulky amino acids and the cysteine to be used as second attachment site, to avoid potential steric hindrance of the bulkier amino acid in the coupling reaction.

In a further preferred embodiment the linker is added to the N-terminus of the antigen. In another preferred embodiment of the invention, the linker is added to the C-terminus of antigen. In other embodiments of the present invention, the composition comprises or alternatively consists essentially of a virus-like particle linked to the antigen via chemical interactions, wherein at least one of these interactions is not a covalent bond. Linking of the modified VLP to the antigen can be effected by biotinylating the modified VLP and expressing the antigen as a streptavidin-fusion protein. In other embodiments of the present invention, the sulfhydryl groups used for chemical coupling to lysines are attached to the modified VLPs or the antigen by means of chemical modification.

In a further preferred embodiment said composition further comprises at least one immuno-stimulatory substance. In a very preferred embodiment, said immunostimulatory substance is packaged into the modified VLPs of the invention. In another preferred embodiment, the immunostimulatory substance is mixed with the modified VLPs of the invention. Immunostimulatory substances useful for the invention are generally known in the art and are disclosed, inter alia, in WO2003/024481A2.

In another embodiment of the present invention, said immunostimulatory substance consists of DNA or RNA of non-eukaryotic origin. In a further preferred embodiment said immunostimulatory substance is selected from the group consisting of: (a) immunostimulatory nucleic acid; (b) peptidoglycan; (c) lipopolysaccharide; (d) lipoteichonic acid; (e) imidazoquinoline compound; (f) flagelline; (g) lipoprotein; and (h) any mixtures of at least one substance of (a) to (g). In a further preferred embodiment said immunostimulatory substance is an immunostimulatory nucleic acid, wherein said immunostimulatory nucleic acid is selected from the group consisting of: (a) ribonucleic acids; (b) deoxyribonucleic acids; (c) chimeric nucleic acids; and (d) any mixture of (a), (b) and/or (c). In a further preferred embodiment said immunostimulatory nucleic acid is a ribonucleic acid, and wherein said ribonucleic acid is bacteria derived RNA. In a further preferred embodiment said immunostimulatory nucleic is poly-(I:C) or a derivative thereof. In a further preferred embodiment said immunostimulatory nucleic acid is a deoxyribonucleic acid, wherein said deoxyribonucleic acid is an unmethylated CpG-containing oligonucleotide.

In a very preferred embodiment said immunostimulatory substance is an unmethylated CpG-containing oligonucleotide. In a further preferred embodiment said unmethylated CpG-containing oligonucleotide is an A-type CpG. In a further preferred embodiment said A-type CpG comprises the sequence GACGATCGTC (SEQ ID NO: 31). In a further preferred embodiment said palindromic sequence is flanked at its 5'-terminus and at its 3'-terminus by guanosine entities. In a further preferred embodiment said palindromic sequence is flanked at its 5'-terminus by at least 3 and at most 15 guanosine entities, and wherein said palindromic sequence is flanked at its 3'-terminus by at least 3 and at most 15 guanosine entities.

In another preferred embodiment, said immunostimulatory substance is an unmethylated CpG-containing oligonucleotide, and wherein preferably said unmethylated CpG-containing oligonucleotide comprises a palindromic sequence, and wherein further preferably the CpG motif of said unmethylated CpG-containing oligonucleotide is part of a palindromic sequence, and wherein again further preferably said palindromic sequence is GACGATCGTC (SEQ ID NO: 31).

In a further preferred embodiment, said immunostimulatory nucleic acid is an unmethylated CpG containing oligonucleotide consisting of the sequence GGGGGGGGGGGGACGATCGTCGGGGGGGGGG (SEQ ID NO:36), wherein said unmethylated CpG-containing oligonucleotide consists exclusively of phosphodiester bound nucleotides.

Antigens which are useful for the purpose of the invention are disclosed for example in WO2002/056905A2, WO2004/007538A2, WO2006/037787A2, WO2004/084940A1, and WO2006/032674A1. In one embodiment said antigen is derived from a source selected from the group consisting of: (a) viruses; (b) bacteria; (c) parasites; (d) tumors; (e) self-molecules; (f) non-peptidic hapten molecules (g) allergens; (h) hormones; (i) cytokines; (k) chemokines; (l) biologically active peptides. In another preferred embodiment, said antigen is a tumor antigen, a self antigen, a polypeptide of a pathogen, an allergen or a hapten. In a further very preferred embodiment, said antigen is calcitonin gene-related peptide (CGRP).

In a further preferred embodiment said antigen is a tumor antigen, wherein preferably said tumor antigen is selected from the group consisting of: (a) a polypeptide of breast cancer cells; (b) a polypeptide of kidney cancer cells; (c) a polypeptide of prostate cancer cells; (d) a polypeptide of skin cancer cells; (e) a polypeptide of brain cancer cells; and (f) a polypeptide of leukemia cells.

In a further preferred embodiment said antigen is a tumor antigen selected from the group consisting of: (a) Her2; (b) gangliosid GD2; (c) EGF-R; (d) carcino embryonic antigen (CEA); (e) CD52; (f) CD21; (g) human melanoma gplOO; (h) human melanoma melanA/MART-1; (i) Human melanoma melanA/MART-1 analogue; (j) tyrosinase; (k) NA17-A nt; (l) MAGE3; (m) p53 protein; and (n) antigenic fragments of any of the tumor antigens of (a) to (m).

In a further preferred embodiment said antigen is a polypeptide selected from the group consisting of: (a) IgE, (b) IL-6 (c) receptor activator of nuclear factor kB ligand (RANKL); (d) vascular endothelial growth factor (VEGF); (e) vascular endothelial growth factor receptor (VEGF-R); hepatocyte growth factor (HGF) (f) interleukin-1α; (g) interleukin-1β; (h) interleukin-5; (i) interleukin-8; (j) inter leukin-13; (k) interleukin-15; (l) interleukin-17 (IL-17); (m) IL-23; (n) Ghrelin; (o) angiotensin; (p) chemokine (C-C motif) (CCL21); (q) chemokine (C-X motif) (CXCL 12); (r) stromal cell derived factor 1 (SDF-I); (s) macrophage colony stimulating factor (M-CSF); (t) monocyte chemotactic protein 1 (MCP-I); (u) endoglin; (v) resistin; (w) gonadotropin releasing hormone (GnRH); (x) growth hormone releasing (GHRH); (y) lutenizing hormone releasing hormone (LHRH); (z) thyreotropin releasing hormon (TRH); (aa) macrophage migration inhibitory factor (MIF); (bb) glucose-dependent insulinotropic peptide (GIP); (cc) eotaxin; (dd) bradykinin; (ee) Des-Arg bradykinin; (ff) B-lymphocyte chemoattractant (BLC); (gg) macrophage colony stimulating factor M-CSF; (hh) tumor necrosis factor α (TNFα); (ii) amyloid beta peptide (Aβ1-42); (jj) amyloid beta peptide (Aβ1-6); (kk) human IgE; (ii) CCRS extracellular domain; (mm) CXCR4 extracellular domain; (nn) Gastrin; (oo) CETP; (pp) C5a; (qq) epidermal growth factor receptor (EGF-R); (rr) CGRP; (ss) α-synuclein; (tt) calcitonin gene-related peptide (CGRP) (uu) Amylin or (vv) a fragment of any one of the polypeptides (a) to (uu); and (xx) an antigenic mutant or fragment of any one of the polypeptides (a) to (uu).

In a further preferred embodiment said antigen is a self antigen, wherein said self antigen is a polypeptide selected from the group consisting of: (a) IgE, (b) IL-6 (c) receptor activator of nuclear factor kB ligand (RANKL); (d) vascular endothelial growth factor (VEGF); (e) vascular endothelial growth factor receptor (VEGF-R); hepatocyte growth factor (HGF) (f) interleukin-1α; (g) interleukin-1β; (h) interleukin-5; (i) interleukin-8; (j) inter leukin-13; (k) interleukin-15; (l) interleukin-17 (IL-17); (m) IL-23; (n) Ghrelin; (o) angiotensin; (p) chemokine (C-C motif) (CCL21); (q) chemokine (C-X motif) (CXCL 12); (r) stromal cell derived factor 1 (SDF-I); (s) macrophage colony stimulating factor (M-CSF); (t) monocyte chemotactic protein 1 (MCP-I); (u) endoglin; (v) resistin; (w) gonadotropin releasing hormon (GnRH); (x) growt hormon releasing (GHRH); (y) lutenizing hormon releasing hormon (LHRH); (z) thyreotropin releasing hormon (TRH); (aa) macrophage migration inhibitory factor (MIF); (bb) glucose-dependent insulinotropic peptide (GIP); (cc) eotaxin; (dd) bradykinin; (ee) Des-Arg bradykinin; (ff) B-lymphocyte chemoattractant (BLC); (gg) macrophage colony stimulating factor M-CSF; (hh) tumor necrosis factor α (TNFα); (ii) amyloid beta peptide (Aβ1-42); (jj) amyloid beta peptide (Aβ1-6); (kk) human IgE; (ii) CCRS extracellular domain; (mm) CXCR4 extracellular domain; (nn) Gastrin; (oo) CETP; (pp) C5a; (qq) epidermal growth factor receptor (EGF-R); (rr) CGRP; (ss) α-synuclein; (tt) calcitonin gene-related peptide (CGRP) (uu) Amylin or (vv) a fragment of any one of the polypeptides (a) to (uu); and (xx) an antigenic mutant or fragment of any one of the polypeptides (a) to (uu).

In a very preferred embodiment, said antigen is interleukin 17 (IL-17). Interleukin 17 is a T cell-derived cytokine that induces the release of pro-inflammatory mediators in a wide range of cell types. Aberrant Th17 responses and overexpression of IL-17 have been implicated in a number of autoimmune disorders including rheumatoid arthritis and multiple sclerosis. Molecules blocking IL-17 such as IL-17-specific monoclonal antibodies have proved to be effective in ameliorating disease in animal models. Moreover, active immunization targeting IL-17 has recently been suggested using virus-like particles conjugated with recombinant IL-17 (Rohn T A, et al., Eur J Immunol (2006) 36: 1-11). Immunization with IL-17-VLP induced high levels of anti-IL-17 antibodies thereby overcoming natural tolerance, even in the absence of added adjuvant. Mice immunized with IL-17-VLP had lower incidence of disease, slower progression to disease and reduced scores of disease severity in both collagen-induced arthritis and experimental autoimmune encephalomyelitis.

Thus, in a further very preferred embodiment, said antigen comprises, or preferably consists of SEQ ID NO:42. Furthermore, the inventive compositions comprising the modified VLPs are used in a method of treating an inflammatory disease, preferably a chronic inflammatory disease in an animal or human. Preferably, said inflammatory disease is selected from RA, MS, Psoriasis, asthma, Crohns, Colitis, COPD, diabetes, neurodermatitis (allergic dermatitis), again preferably wherein said inflammatory disease MS. Further preferably said antigen of said inventive compositions comprises, or preferably consists of SEQ ID NO:42.

In another very preferred embodiment, said antigen is IL-5. In again a further very preferred embodiment, said antigen comprises, or preferably consists of SEQ ID NO:41. Furthermore, the inventive compositions comprising the modified VLPs are used in a method of treating an inflammatory disease, preferably a chronic inflammatory disease in an animal or human. Preferably, said inflammatory disease is selected from RA, MS, Psoriasis, asthma, Crohns, Colitis, COPD, diabetes, neurodermatitis (allergic dermatitis). Further preferably said antigen of said inventive compositions comprises, or preferably consists of SEQ ID NO:41.

In another very preferred embodiment, said antigen is canine IL-5. In again a further very preferred embodiment, said antigen comprises, or preferably consists of SEQ ID NO:61 or an amino acid sequence having a sequence identity of at least 90%, preferably of at least 95%, with SEQ ID NO:61. Preferably, said antigen comprises, or preferably consists of SEQ ID NO:61. In another preferred embodiment, said antigen of said inventive composition comprises, or preferably consists of SEQ ID NO:61. Further preferably, the inventive composition comprises (i) a modified virus-like particle (VLP) of cucumber mosaic virus (CMV) with at least one first attachment site, wherein said modified VLP of CMV comprises, essentially consists of, or alternatively consists of, at least one modified CMV polypeptide, wherein said modified CMV polypeptide comprises, or preferably consists of, (a) a CMV polypeptide, and (b) a T helper cell epitope; and wherein said modified CMV polypeptide comprises, preferably consists of, an amino acid sequence of SEQ ID NO:6 or SEQ ID NO:7; (ii) at least one antigen with at least one second attachment site, and wherein said antigen is canine IL-5; and wherein said VLP of CMV and said canine IL-5 are linked through said at least one first and said at least one second attachment site, and wherein said canine IL-5 comprises, or preferably consists of SEQ ID NO:61 or an amino acid sequence having a sequence identity of at least 90%, preferably of at least 95% with SEQ ID NO:61, and again preferably wherein said canine IL-5 comprises, or preferably consists of SEQ ID NO:61.

In another very preferred embodiment, said antigen is IL-4. In again a further very preferred embodiment, said antigen comprises, or preferably consists of SEQ ID NO:45.

In another very preferred embodiment, said antigen is canine IL-4. In again a further very preferred embodiment, said antigen comprises, or preferably consists of SEQ ID NO:62 or an amino acid sequence having a sequence identity of at least 90%, preferably of at least 95%, with SEQ ID NO:62. Preferably, said antigen comprises, or preferably consists of SEQ ID NO:62. In another preferred embodiment, said antigen of said inventive composition comprises, or preferably consists of SEQ ID NO:62. Further preferably, the inventive composition comprises (i) a modified virus-like particle (VLP) of cucumber mosaic virus (CMV) with at least one first attachment site, wherein said modified VLP of CMV comprises, essentially consists of, or alternatively consists of, at least one modified CMV polypeptide, wherein said modified CMV polypeptide comprises, or preferably consists of, (a) a CMV polypeptide, and (b) a T helper cell epitope; and wherein said modified CMV polypeptide comprises, preferably consists of, an amino acid sequence of SEQ ID NO:6 or SEQ ID NO:7; (ii) at least one antigen with at least one second attachment site, and wherein said antigen is canine IL-4; and wherein said VLP of CMV and said canine IL-4 are linked through said at least one first and said at least one second attachment site, and wherein said canine IL-4 comprises, or preferably consists of SEQ ID NO:62 or an amino acid sequence having a sequence identity of at least 90%, preferably of at least 95% with SEQ ID NO:62, and again preferably wherein said canine IL-4 comprises, or preferably consists of SEQ ID NO:62.

In another very preferred embodiment, said antigen is IL-13. In again a further very preferred embodiment, said antigen comprises, or preferably consists of SEQ ID NO:46.

In another very preferred embodiment, said antigen is canine IL-13. In again a further very preferred embodiment, said antigen comprises, or preferably consists of SEQ ID NO:63 or an amino acid sequence having a sequence identity of at least 90%, preferably of at least 95%, with SEQ ID NO:63. Preferably, said antigen comprises, or preferably consists of SEQ ID NO:63. In another preferred embodiment, said antigen of said inventive composition comprises, or preferably consists of SEQ ID NO:63. Further preferably, the inventive composition comprises (i) a modified virus-like particle (VLP) of cucumber mosaic virus (CMV) with at least one first attachment site, wherein said modified VLP of CMV comprises, essentially consists of, or alternatively consists of, at least one modified CMV polypeptide, wherein said modified CMV polypeptide comprises, or preferably consists of, (a) a CMV polypeptide, and (b) a T helper cell epitope; and wherein said modified CMV polypeptide comprises, preferably consists of, an amino acid sequence of SEQ ID NO:6 or SEQ ID NO:7; (ii) at least one antigen with at least one second attachment site, and wherein said antigen is canine IL-13; and wherein said VLP of CMV and said canine IL-13 are linked through said at least one first and said at least one second attachment site, and wherein said canine IL-13 comprises, or preferably consists of SEQ ID NO:63 or an amino acid sequence having a sequence identity of at least 90%, preferably of at least 95% with SEQ ID NO:63, and again preferably wherein said canine IL-13 comprises, or preferably consists of SEQ ID NO:63.

In a further very preferred embodiment, said antigen is TNFα. In a further very preferred embodiment, said antigen is IL-1α.

In a further very preferred embodiment, said antigen is IL-1β. In again a further very preferred embodiment, said antigen comprises, or preferably consists of SEQ ID NO:60.

In again a further very preferred embodiment, said antigen is a peptide derived from Aβ-1-42. In again a further very preferred embodiment, said antigen is IgE or a peptide or domain comprised in IgE.

In yet another very preferred embodiment, said antigen is human, feline or canine IL-31. In another very preferred embodiment, said antigen comprises, or preferably consists of SEQ ID NO:43 or SEQ ID NO:44. In another very preferred embodiment, said antigen is canine IL-31. In again a further very preferred embodiment, said antigen comprises, or preferably consists of SEQ ID NO:43 or an amino acid sequence having a sequence identity of at least 90%, preferably of at least 95%, with SEQ ID NO:43. Preferably, said antigen comprises, or preferably consists of SEQ ID NO:43. In another preferred embodiment, said antigen of said inventive compositions comprises, or preferably consists of SEQ ID NO:43. Further preferably, the inventive composition comprises (i) a modified virus-like particle (VLP) of cucumber mosaic virus (CMV) with at least one first attachment site, wherein said modified VLP of CMV comprises, essentially consists of, or alternatively consists of, at least one modified CMV polypeptide, wherein said modified CMV polypeptide comprises, or preferably consists of, (a) a CMV polypeptide, and (b) a T helper cell epitope; and wherein said modified CMV polypeptide comprises, preferably consists of, an amino acid sequence of SEQ ID NO:6 or SEQ ID NO:7; (ii) at least one antigen with at least one second attachment site, and wherein said antigen is canine IL-31; and wherein said VLP of CMV and said canine IL-31 are linked through said at least one first and said at least one second attachment site, and wherein said canine IL-31 comprises, or preferably consists of SEQ ID NO:43 or an amino acid sequence having a sequence identity of at least 90%, preferably of at least 95% with SEQ ID NO:43, and again preferably wherein said canine IL-31 comprises, or preferably consists of SEQ ID NO:43.

In another very preferred embodiment, said antigen is α-synuclein or a peptide derived from α-synuclein, and wherein preferably said peptide consists of 6 to 14 amino acids, and wherein further preferably said antigen is a peptide derived from α-synuclein selected from any one of SEQ D NO:32, SEQ ID NO:33 and SEQ ID NO:34. Further preferred peptides derived from α-synuclein are disclosed in WO 2011/020133, which is incorporated herein by way of reference.

Alpha-synuclein (α-Syn), a small protein with multiple physiological and pathological functions, is one of the dominant proteins found in Lewy Bodies, a pathological hallmark of Lewy body disorders, including Parkinson's disease (PD). More recently, α-Syn has been found in body fluids, including blood and cerebrospinal fluid, and is likely produced by both peripheral tissues and the central nervous system. Exchange of α-Syn between the brain and peripheral tissues could have important pathophysiologic and therapeutic implications (Gardai S J et al., PLoS ONE (2013) 8(8): e71634). The evidence implicating alpha-synuclein (a-syn) in the pathogenesis of Parkinson's Disease (PD) is overwhelming. However, there is not a clear consensus on the manner in which a-syn leads to pathology in PD and other synucleinopathies.

Alpha-synuclein is a major component of Lewy bodies (LBs), and descriptions of a-syn overexpression leading to aggregation are abundant. Human genetic data have demonstrated that missense mutations and multiplications in the a-syn gene cause familial PD. In the case of gene multiplication, increased levels of a-syn protein are presumed to result in a dominant gain-of-function that leads to pathology. While increased levels of a-syn may lead to aggregation and toxicity, research over the past few years has also revealed that elevated a-syn can interfere with the creation, localization, and/or maintenance of vesicle pools (Gardai S J et al., PLoS ONE (2013) 8(8): e71634; and references cited therein.

In again a further very preferred embodiment, said antigen is Amylin. In a very preferred embodiment, said antigen is angiotensin I or a peptide derived from angiotensin I. In another very preferred embodiment, said antigen is angiotensin II or a peptide derived from angiotensin II. In a further very preferred embodiment, said antigen is GnRH. In a further very preferred embodiment, said antigen is eotaxin.

In a further preferred embodiment said antigen is a polypeptide of a parasite, wherein preferably said pathogen is selected from the group consisting of: (a) *Toxoplasma* spp.; (b) *Plasmodium falciparum*; (c) *Plasmodium vivax*; (d) *Plasmodium ovale*; (e) *Plasmodium malariae*; (f) *Leishmania*; (g) *Schistosoma* and (h) Nematodes. Preferably, said antigen antigen is derived from *Plasmodium falciparum* or *Plasmodium Vivax*.

In a further preferred embodiment, said antigen is a polypeptide of a bacterium, wherein preferably said bacterium is selected from the group consisting of: (a) *Chlamydia* (b) *Streptocoocccus*; (c) *Pneumococcus*; (d) *Staphylococcus*; (e) *Salmonella*; (f) Mycobacteria; (g) Clostridia (h) *Vibrio* (i) *Yersinia* (k) *Meningococcus* (l) Borelia.

In a further preferred embodiment said antigen is a viral antigen, wherein preferably said viral antigen is a polypeptide selected from the group consisting of: (a) HIV and other retrovirsues; (b) influenza virus, preferably influenza A M2 extracellular domain or HA or HA globular domain; (c) a polypeptide of Hepatitis B virus, preferably preSl; (d) Hepatitis C virus; (e) HPV, preferably HPV16E7 (f) RSV, (g) SARS and other Coronaviruses, (h) Dengue and other Flaviviruses, such as West Nile Virus and Hand Foot and Mouth Disease Virus, (i) Chikungunya and other Alphaviruses. (k) CMV and other Herpesviruses, (l) Rotavirus. In a further very preferred embodiment, said antigen is the derived from RSV.

In a preferred embodiment, said antigen is the extracellular domain of Influenza A virus M2 protein, or an antigenic fragment thereof. In a very preferred embodiment said antigen comprises or preferably consists of the extracellular domain of the Influenza A virus M2 protein, wherein preferably said extracellular domain of the Influenza A virus M2 protein is SEQ ID NO:24. In another preferred embodiment, said antigen is the globular domain of Influenza virus.

In a further preferred embodiment said antigen is an allergen, wherein preferably said allergen is derived from the group consisting of: (a) pollen extract; (b) dust extract; (c) dust mite extract; (d) fungal extract; (e) mammalian epidermal extract; (f) feather extract; (g) insect extract; (h) food extract; (i) hair extract; (j) saliva extract; and (k) serum extract. In a further preferred embodiment said antigen is an allergen, wherein said allergen is selected from the group consisting of: (a) trees; (b) grasses; (c) house dust; (d) house dust mite; (e) *aspergillus*; (f) animal hair; (g) animal feather; (h) bee venom; (i) animal products; (j) plant products; (k) animal dander; (l) peanut allergens.

In a further preferred embodiment said antigen is a recombinant allergen, wherein said allergen is selected from the group consisting of: (a) bee venom phospholipase A2; (b) ragweed pollen Amb a 1; (c) birch pollen Bet v I; (d) white faced hornet venom 5 DoI m V; (e) house dust mite Der p 1; (f) house dust mite Der f 2; (g) house dust mite Der p 2; (h) dust mite Lep d; (i) fungus allergen Alt a 1; (j) fungus allergen Asp f 1; (k) fungus allergen Asp f 16; (l) peanut allergens (m) cat allergen Fel d1; (n) Canine allergens Can f1, Can f2 (o) peanut-derived allergens; or (p) Japanese cedar allergen Cry J2. In another very preferred embodiment of the present invention, said antigen dog allergen Can f1 or Can f2.

In a further very preferred embodiment, said antigen is a peanut allergen. Preferably, said antigen is a peanut allergen comprising an amino acid sequence selected from SEQ ID NO:57, SEQ ID NO:64 or SEQ ID NO:65.

In a further very preferred embodiment, said antigen is an allergen derived from Japanese Cedar Cry J 2. Preferably, said antigen is derived from Japanese Cedar Cry J 2 and comprises the amino acid sequence of SEQ ID NO:55.

In a further very preferred embodiment, said antigen is an allergen derived from ragweed pollen Amb a 1. Preferably, said antigen is derived from ragweed pollen Amb a 1 and comprises the amino acid sequence of SEQ ID NO:54.

In a very preferred embodiment of the present invention, said antigen cat allergen Fel d1. The domestic cat (*Felis domesticus*) is an important source of indoor allergens (Lau, S., et al. (2000) Lancet 356, 1392-1397). Indeed, cats are found in about 25% of households in Western countries and allergy to cats is found in a large part of the population. The severity of symptoms range from relatively mild rhinitis and conjunctivitis to potentially life-threatening asthmatic exacerbation. Although patients are occasionally sensitized to several different molecules in cat dander and pelts, the major allergen is Fel d1. The importance of this allergen has been emphasised in numerous studies. In fact more than 80% of cat allergic patients exhibit IgE antibodies to this potent allergen (van Ree, R., et al. (1999) J. Allergy Clin Immunol 104, 1223-1230).

Fel d1 is a 35-39 kDa acidic glycoprotein containing 10-20% N-linked carbohydrates and is found in the pelt, saliva and lachrymal glands of cats. It is formed by two non-covalently linked heterodimers. Each heterodimer consists of one 70 residue peptide (known as "chain 1") and one 78, 85, 90 or 92 residue peptide (known as "chain 2") which are encoded by separate genes (see Duffort, O. A., et al. (1991) Mol Immunol 28, 301-309; Morgenstern, J. P., et al; (1991) Proc Natl Acad Sci USA 88, 9690-9694 and Griffith, I. J., et al. (1992) Gene 113, 263-268).

Several recombinant constructs of Fel d1 have been described (Vailes L D, et al., J Allergy Clin Immunol (2002) 110:757-762; Grönlund H, et al., J Biol Chem (2003) 278:40144-40151; 2003 Schmitz N, et al., J Exp Med (2009) 206:1941-1955; WO2006/097530).

Thus, in a further very preferred embodiment, said antigen is a rFel d1. In a further very preferred embodiment, said antigen is a Fel d1 protein, wherein said Fel d1 protein is a fusion protein comprising chain 1 of Fel d1 and chain 2 of Fel d1, wherein said chain 2 of Fel d1 is fused via its C-terminus to the N-terminus of said chain 1 of Fel d1 either directly via one peptide bond or via a spacer, wherein said spacer consists of an amino acid sequence having 1-20 amino acid residues, wherein preferably said spacer consists of an amino acid sequence having 10-20 amino acid residues. Very preferably, said spacer consists of an amino acid sequence of 15 amino acid residues, and further preferably said spacer has the amino acid sequence of SEQ ID NO:47. In a further very preferred embodiment, said antigen is a Fel d1 protein, wherein said Fel d1 protein is a fusion protein comprising chain 1 of Fel d1 and chain 2 of Fel d1, wherein said chain 1 of Fel d1 is fused via its C-terminus to the N-terminus of said chain 2 of Fel d1 either directly via one peptide bond or via a spacer, wherein said spacer consists of an amino acid sequence having 1-20 amino acid residues, wherein preferably said spacer consists of an amino acid sequence having 10-20 amino acid residues. Preferably, said chain 1 of Fel d 1 comprises a sequence of SEQ ID NO:37 or a homologue sequence thereof, wherein said homologue sequence has an identity to SEQ ID NO:37 of greater than 90%, or even more preferably greater than 95%. Further preferably, said chain 2 of Fel d 1 comprises a sequence of SEQ ID NO:38, SEQ ID NO:39 or SEQ ID NO:40, or a homologue sequence thereof, wherein said homologue sequence has an identity to SEQ ID NO:38, SEQ ID NO:39 or SEQ ID NO:40 of greater than 90%, and even more preferably greater than 95%.

In a very preferred embodiment, said antigen comprises, preferably consists of, SEQ ID NO:17. In another very preferred embodiment, said antigen comprises, preferably consists of, SEQ ID NO:18. In another very preferred embodiment, said antigen comprises, preferably consists of, SEQ ID NO:52. In a very preferred embodiment said antigen is a Fel d1 protein comprising an amino acid sequence selected from: (a) SEQ ID NO:17; (b) SEQ ID NO:18; (c) SEQ ID NO:50; (d) SEQ ID NO:56; (e) SEQ ID NO:59; or SEQ ID NO:52.

In a further very preferred embodiment, said Fel d1 protein comprises an amino acid sequence selected from: (a) SEQ ID NO:50; (b) SEQ ID NO:56 (c) SEQ ID NO:59; or (d) SEQ ID NO:52. In a further very preferred embodiment, said Fel d1 protein comprises an amino acid sequence selected from: (a) SEQ ID NO:50; (b) SEQ ID NO:56 or (c) SEQ ID NO:59.

In another very preferred embodiment, said Fel d1 protein comprises, preferably consists of, an amino acid sequence of SEQ ID NO:52. In another very preferred embodiment, said Fel d1 protein comprises, preferably consists of, an amino acid sequence of SEQ ID NO:59. In another very preferred embodiment, said Fel d1 protein comprises, preferably consists of, an amino acid sequence of SEQ ID NO:50. In another very preferred embodiment, said Fel d1 protein comprises, preferably consists of, an amino acid sequence of SEQ ID NO:56.

In a very preferred embodiment, the inventive composition comprises (i) a modified virus-like particle (VLP) of cucumber mosaic virus (CMV) with at least one first attachment site, wherein said modified VLP of CMV comprises, essentially consists of, or alternatively consists of, at least one modified CMV polypeptide, wherein said modified CMV polypeptide comprises, or preferably consists of, (a) a CMV polypeptide, and (b) a T helper cell epitope; and wherein said modified CMV polypeptide comprises, preferably consists of, an amino acid sequence of SEQ ID NO:6 or SEQ ID NO:7; (ii) at least one antigen with at least one second attachment site, and wherein said antigen is a Fel d1 protein; and wherein said VLP of CMV and said Fel d1 protein are linked through said at least one first and said at least one second attachment site, and wherein said Fel d1 protein comprises an amino acid sequence selected from (a) SEQ ID NO:50; (b) SEQ ID NO:56 (c) SEQ ID NO:59; or (d) SEQ ID NO:52, and wherein preferably said Fel d1 protein comprises an amino acid sequence selected from: (a) SEQ ID NO:50; (b) SEQ ID NO:56 or (c) SEQ ID NO:59.

In a further preferred embodiment said antigen is an animal venom. In a preferred embodiment, the antigen is inactivated snake venom. In a further preferred embodiment said antigen is a hapten. In a further preferred embodiment said hapten is a drug, wherein preferably said drug is selected from the group consisting of: (a) codeine; (b) fentanyl; (c) heroin; (d) morphine; (e) amphetamine; (f) cocaine; (g) methylenedioxymethamphetamine; (h) methamphetamine; (i) methylphenidate; (j) nicotine; (k) LSD; (l) mescaline; (m) psilocybin; (n) tetrahydrocannabinol; and (o) nicotine In a further preferred embodiment said hapten is a hormone, wherein preferably said hormone is selected from the group consisting of: (a) progesterone; (b) estrogen; (c) testosterone; (d) follicle stimulating hormone; (e) melanin stimulating hormone; (f) adrenalin; and (g) noradrenalin. In a further preferred embodiment said hapten is a toxin, wherein preferably said toxin is selected from the group consisting of: (a) aflatoxin; (b) ciguetera toxin; (c) tetrodotoxin; and (d) antibiotics. In a further preferred embodiment said hapten is a pathogen-derived carbohydrate.

In a further aspect the invention provides a vaccine comprising or alternatively consisting of the modified virus-like particle of the invention or of the composition of the invention. Encompassed are vaccines wherein said modified VLPs, and/or said composition comprise any one of the technical features disclosed herein, either alone or in any possible combination. In one embodiment the vaccine further comprises an adjuvant. In a further embodiment the vaccine is devoid of an adjuvant. In a preferred embodiment said vaccine comprises an effective amount of the composition of the invention. An "effective amount" refers to an amount which needs to be administered to a subject in order to achieve a detectable physiological effect.

In a further aspect, the invention relates to a pharmaceutical composition comprising: (a) a modified VLP of the invention, a composition of the invention, or a vaccine of the invention; and (b) a pharmaceutically acceptable carrier, diluent and/or excipient. Said diluent includes sterile aqueous (e.g., physiological saline) or non-aqueous solutions and suspensions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Pharmaceutical compositions of the invention may be in a form which contain salts, buffers, adjuvants, or other substances which are desirable for improving the efficacy of the conjugate. Examples of materials suitable for use in preparation of pharmaceutical compositions are provided in numerous sources including Remington's Pharmaceutical Sciences (Osol, A, ed., Mack Publishing Co., (1990)). In one embodiment said pharmaceutical composition comprises an effective amount of the vaccine of the invention. An "effective amount" refers to an amount which needs to be administered to a subject in order to achieve an detectable physiological effect.

A further aspect of the invention is a method of immunization comprising administering a modified VLP of the invention, a composition of the invention, a vaccine of the invention, or a pharmaceutical composition of the invention to an animal or a human. In a preferred embodiment said method comprises administering a composition of the invention, a vaccine of the invention, or a pharmaceutical composition of the invention to an animal or a human.

A further aspect of the invention is a method of treating or preventing a disease, disorder or physiological condition in an animal said method comprising administering a modified VLP of the invention, a composition of the invention, a vaccine of the invention, or a pharmaceutical composition of the invention to said animal, wherein preferably said animal can be a human. In a further preferred embodiment said modified VLP, said composition, said vaccine, or said pharmaceutical composition is administered to said animal subcutaneously, intravenously, intradermally, intranasally, orally, intranodal or transdermally.

EXAMPLES

Example 1

Isolation and Cloning of a Coat Protein (CP) of Cucumber Mosaic Virus (CMV)

The total RNA from CMV-infected lily leaves collected from a private garden in Riga, Latvia, was isolated using TRI reagent (Sigma, Saint Louis, USA) in accordance with manufacturer's recommendations. For cDNA synthesis, OneStep RT-PCR kit (Qiagen, Venlo, Netherlands) was used. For amplification of the CMV CP gene, the primer sequences were chosen following analysis of CMV sequences from GenBank: CMcpF (CA CCATGGACAAATCTGAA TCAACCAGTGCTGGT) (SEQ ID NO: 8) and CMcpR (CA AAGCTTATCAAACTGGGAGCA CCCCA-GATGTGGGA) (SEQ ID NO:9); NcoI and HindIII sites underlined. The corresponding PCR products were cloned into the pTZ57R/T vector (Fermentas, Vilnius, Lithuania). *E. coli* XL1-Blue cells were used as a host for cloning and plasmid amplification. To avoid RT-PCR errors, several CP gene-containing pTZ57 plasmid clones were sequenced using a BigDye cycle sequencing kit and an ABI PRISM 3100 Genetic analyzer (Applied Biosystems, Carlsbad, USA). After sequencing, the cDNA of CMV CP gene without sequence errors (SEQ ID NO: 10) coding for CMV coat protein of SEQ ID NO:1 was then subcloned into the NcoI/HindIII sites of the pET28a(+) expression vector (Novagen, San Diego, USA), resulting in the expression plasmid pET-CMVwt (FIG. 1).

Example 2

Expression of CP of SEQ ID NO:1 in *E. coli* Leading to VLPs of CMV

To obtain CMV VLPs, *E. coli* C2566 cells (New England Biolabs, Ipswich, USA) were transformed with the CMV CP gene-containing plasmid pET-CMVwt. After selection of clones with the highest expression levels of target protein, *E. coli* cultures were grown in 2×TY medium containing kanamycin (25 mg/1) on a rotary shaker (200 rev/min; Infors, Bottmingen, Switzerland) at 30° C. to an OD600 of 0.8-1.0. Then, the cells were induced with 0.2 mM IPTG, and the medium was supplemented with 5 mM MgCl2. Incubation was continued on the rotary shaker at 20° C. for 18 h. The resulting biomass was collected by low-speed centrifugation and was frozen at −20° C. After thawing on ice, the cells were suspended in the buffer containing 50 mM sodium citrate, 5 mM sodium borate, 5 mM EDTA, 5 mM mercaptoethanol (pH 9.0, buffer A) and were disrupted by ultrasonic treatment. Insoluble proteins and cell debris were removed by centrifugation (13,000 rpm, 30 min at 5° C.). The soluble CMV CP protein in clarified lysate was pelleted using saturated ammonium sulfate (1:1, vol/vol) overnight at +4° C. Precipitated proteins were solubilized in the same buffer A (without mercaptoethanol) for 4 h at +4° C. Insoluble proteins were removed by low speed centrifugation (13,000 rpm, 15 min at 4° C.). Soluble CMV CP-containing protein solution was separated from the cellular proteins by ultracentrifugation (SW28 rotor, Beckman, Palo Alto, USA; at 25,000 rpm, 6 h, 5° C.) in a sucrose gradient (20-60% sucrose in buffer A, without mercaptoethanol, supplemented with 0.5% TRITON X-100). The gradient was divided into six fractions, starting at the bottom of the gradient, and the fractions were analyzed by SDS-PAGE (FIG. 2). Fractions No. 2 and No. 3 containing recombinant CMV CP were combined and were dialyzed against 200 volumes of the buffer (5 mM sodium borate, 2 mM EDTA, pH 9.0) to remove the sucrose and TRITON X-100. After dialysis, CMV CP solution was sterilized by filtration through the 0.2μ filter. Next, CMV CP was concentrated using Type70 rotor (Beckman, Palo Alto, USA) ultracentrifugation through the 20% sucrose "cushion" under sterile conditions (50 000 rpm, 4 h, +5° C.). The concentration of purified CMVwt was estimated using the QUBIT fluorometer in accordance with manufacturer's recommendations (Invitrogen, Eugene, USA). Concentrated VLP solutions (approx. 3 mg/ml) were stored at +4° C. in 5 mM sodium borate, 2 mM EDTA, buffer (pH 9.0). All steps involved in the expression and purification of VLP were monitored by SDS-PAGE using 12.5% gels.

As shown in FIG. 2, CMV coat protein can be successfully expressed in *E. coli* cells and significant part obtained can be in soluble fraction. Moreover, these proteins are found directly in *E. coli* cell extracts in the form of isometric VLPs, as demonstrated by sucrose gradient analysis (FIG. 3A), dynamic light scattering and electron-microscopy analysis (FIG. 3B).

Example 3

Cloning of a Modified Coat Protein of CMV Containing an Tetanus Toxoid Epitope (CMV-Ntt830)

Figure 7A:
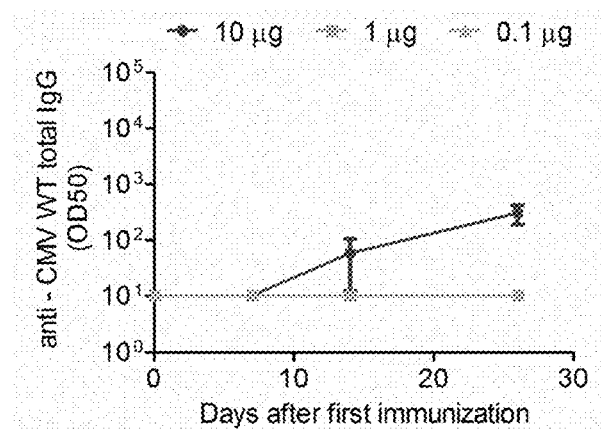
Figure 7B:
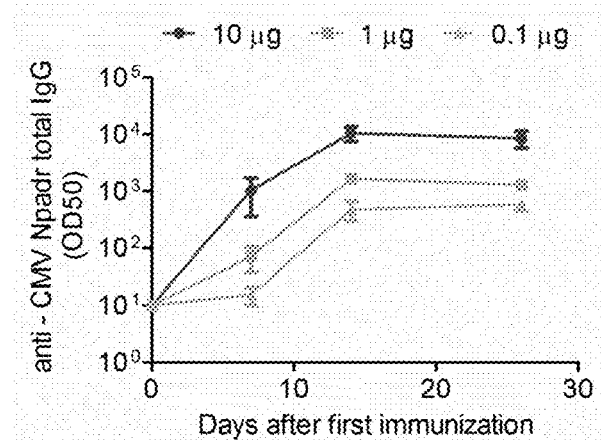
Figure 7C:
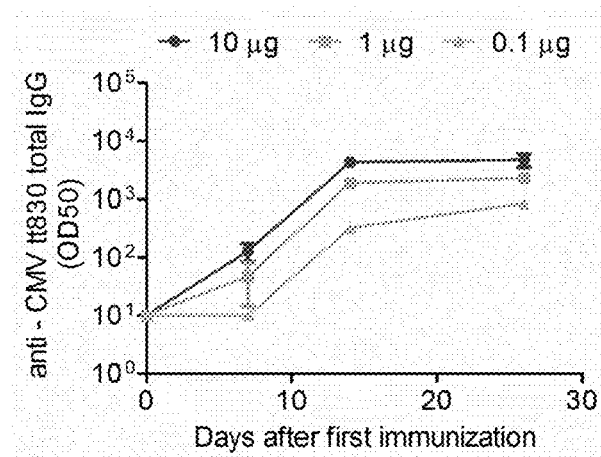

To replace the original amino acids at the N-terminus of CMV CP of SEQ ID NO:1 against foreign epitope sequences, as a template for PCR amplification and mutagenesis the pET-CMVwt plasmid was used. Internally in CMVwt gene located SalI site (FIG. 1) was used for cloning corresponding PCR products.

To introduce the tetanus toxoid epitope coding sequence in CMVwt gene, two step PCR mutagenesis was necessary. For the first step amplification following primers were used for PCR: pET-220 (AGCACCGCCGCCGCAAGGAA (SEQ ID NO: 11)—upstream from polylinker, the amplified region includes BglII site) and CMV-tt83-1R (ATTTG-GAGTTGGCCTTAATATACT GGCC-CATGGTATATCTCCTTCTTAAAGT) (SEQ ID NO:12). For the second round the PCR product from the first round was diluted 1:50 and re-amplified with primers pET-220 (SEQ ID NO: 11) and CMV-tt83Sal-R2 (GACGTCGACGCTCGGTAATCCCGATAAATTTG-GAGTTG GCCTTAATATACTG) (SEQ ID NO:13). Resulting PCR product (cDNA of SEQ ID NO:14 coding for CMV-Ntt830 of SEQ ID NO: 6) was subcloned in BglII/SaLI sites of pET-CMVwt. The correct clone was identified by sequencing and designated as pET-CMV-Ntt830.

Example 4

Expression of CMV-Ntt830 in *E. coli* Leading to Modified VLPs of CMV

The procedures for expression and purification of CMV-Ntt830 were essentially the same as for CMVwt and are described in Example 2. To demonstrate the presence of tetanus epitope in CMV VLPs, the mass spectrometric analysis of the purified CMV-Ntt830 VLPs was used. As shown in FIG. 4C, the major peak obtained corresponds to the theoretical molecular mass of the protein if the first methionine is removed during the protein synthesis in *E. coli* cells. Dynamic light scattering and electron microscopy analysis confirm the isometric particle morphology similar to CMVwt VLPs (FIG. 5).

Example 5

Cloning of a Modified Coat Protein of CMV Containing a PADRE Epitope (CMV-Npadr)

To introduce the PADRE epitope coding sequence in CMVwt gene, PCR mutagenesis was carried out using as the template for amplification and subcloning the pET-CMVwt plasmid (see also Example 3). For the amplification following primers were used: pET-220 (SEQ ID NO: 11) and CMV-padrSal-R (GACGTCGACGCGCGGCCGCCTT-GAGGGTCCACGCGGCCACAAATTT CGCCATGGT) (SEQ ID NO:15). The resulting PCR product (cDNA of SEQ ID NO:16 coding for CMV-Npadr of SEQ ID NO: 7) was again subcloned in BglII/SalI sites of pET-CMVwt. The correct clone was identified by sequencing and designated as pET-CMV-Npadr.

Example 6

Expression of CMV-Npadr in *E. coli* Leading to Modified VLPs of CMV

The procedures for expression and purification of CMV-Npadr were essentially the same as for CMVwt and are described in Example 2. To demonstrate the presence of the PADRE epitope in CMV VLPs, the mass spectrometric analysis of the purified CMV-Npadr VLPs was used. As shown in FIG. 4B, the major peak obtained corresponds to the theoretical molecular mass of the protein if the first methionine is removed during the protein synthesis in *E. coli* cells. Dynamic light scattering and electron microscopy analysis confirm the isometric particle morphology, which is slightly different from CMVwt and CMV-Nt830 VLPs (FIG. 6).

Example 7

Immunization of Mice with CMVwt, CMV-Ntt830 and CMV-Npadr

Groups of four female Balb/c mice were either immunized with CMVwt, CMV-Npadr VLP and CMV-Ntt830 VLP. VLPs were formulated in 150 mM PBS, pH 7.4 and 150 μl were injected i.v. on day 0 and day 7. CMVwt, CMV-Npadr VLP and CMV-Ntt830 VLP were injected in three amounts: 10, 1 or 0.1 μg. Mice were bled on days 0 (pre-immune), day 7, day 14, and day 25, and sera were analyzed using CMVwt VLPs, CMV-Npadr VLP and CMV-Ntt830 VLP-specific ELISA. All immune sera were tested against the respective VLPs used for immunization.

ELISA

The antibody response in mouse sera were analyzed at the indicated time. For determination of CMVwt, CMV-Npadr VLP and CMV-Ntt830 VLP specific antibody titers, ELISA plates (NUNC IMMUNO MAXISORP, Rochester, N.Y.) were coated overnight at 4° C. with 100 μl of the corresponding VLP (1 μg/ml) in coating buffer (0.1 M Sodium hydrogen carbonate buffer, pH 9.6). In order to avoid unspecific binding the ELISA plates were blocked with 200 μl of 2% BSA in PBST and incubated for 2 hours at RT. The serum samples were diluted in 2% BSA/PBST. Pre-diluted sera were transferred onto the coated plates and further serial diluted to obtain antibody titers based on OD50 calculation. After 2 hours of incubation at RT, the ELISA plates were washed 5× with 200 μl of PBST. Binding of serum antibodies was detected by horse-radish peroxidase-conjugated goat anti-mouse IgG (Jackson ImmunoResearch). The detection antibody was diluted 1:1000 in 2% BSA/PBST and a volume of 100 μl per sample was transferred. The plates were incubated for 1 hour at RT. ELISA plates were washed as described before. Prior washing the substrate solution was prepared. To this end, 1 tablet (10 mg) of OPD (1,2-Phenylenediamine dihydrochloride) and 9 μl of 30% H2O2 was dissolved in 25 ml citric acid buffer (0.066 M Na2HPO4, 0.035 M citric acid, pH 5.0). A volume of 100 μl of the substrate solution was pipetted onto the plates and exactly incubated for 7 minutes at RT. To stop the reaction 50 μl of stop solution (5% H2SO4 in H2O) was directly pipetted onto the plates. Absorbance readings at 450 nm of the 1, 2-Phenylenediamine dihydrochloride color reaction were analyzed. FIG. 7 shows antibodies specific for CMVwt (FIG. 7A), -CMV-Npadr (FIG. 7B) and CMV-Ntt880 (FIG. 7C) in a dose dependent manner.

Example 8

Coupling of Recombinant Fel d1 Constructs to VLP CMV-Npadr and VLP CMV-Ntt830 and Induction of Immune Responses A covalent fusion of rFel d1 (SEQ ID NO:17 was generated as previously described (Schmitz N, et al., J Exp Med (2009) 206:1941-1955). In brief, a complementary DNA encoding a covalent dimer of chain 2 and chain 1, wherein the chain 2 of Fel d1 is fused via its C-terminus to the N-terminus of chain 1 of Fel d1 spaced by a 15aa-linker (GGGGS)$_3$ was obtained by PCR amplification using sets of overlapping DNA-primers (the construct is named "rFel-2-G3-1-construct"). This complementary DNA was cloned in frame into a modified version of pET-42a(+) (EMD), leading to the addition of the coding sequence for LEHHHHHHGGC (SEQ ID NO:35) at the C terminus of the rFel-2-G3-1-construct. The added sequence contains a His tag for purification, followed by a GGC linker used for the coupling of this Fel d1 fusion protein to CMV-Npadr and CMV-Ntt830.

Analogously, another covalent fusion of rFel d1 (SEQ ID NO:18) is generated as previously described (WO2006/097530) corresponding to a rFel d1 fusion protein comprising chain 1 of Fel d1 and chain 2 of Fel d1, wherein the chain 1 of Fel d1 is fused via its C-terminus to the N-terminus of chain 2 of Fel d1 by a 15aa-linker (GGGGS)$_3$ ("rFel-1-G3-2-construct").

The virus like particles VLP CMV-Npadr and VLP CMV-Ntt830 in a volume of 2.5 ml with a concentration of 2 mg/ml (71 µM) reacted with 27 µl of 50 mM of the heterobifunctional chemical cross-linker succinimidyl-6-(b-maleimidopropionamide) hexanoate (SMPH) for 1 hour at room temperature (RT). The linker contains a NHS ester which reacts with the lysine on the surface of the VLP. The amount of SMPH refers to 7.5× molar excess regarding one VLP monomer, i.e. one CMV polypeptide. Non-reacted cross-linker was removed by dialysis against 150 mM PBS, pH 7.4. To produce the rFel d1-CMV-Npadr and rFel d1-CMV-Ntt830 compositions, a protein solution of rFel d1 with a concentration of 2.7 mg/ml referring to 150 µM in a volume of 200 µl was mixed with 5× molar excess of the reducing agent Tris-2-carboxyethyl-phosphine (TCEP) and incubated for 5 min at RT. The molar excess was related to the protein Fel d1 amount. TCEP reduces disulfide bridges between two cysteine residues of two protein molecules in order to assure their available for the coupling reaction to derivatized VLPs. The pre-treated protein Fel d1 were reacted in a molar ratio of 1:1 with 7.5×SMPH derivatized VLP CMV-Npadr and VLP CMV-Ntt830 for 3 hours at RT while shaking. The reduced cysteine of the protein reacted with the maleimide of the crosslinker SMPH bound to the VLP. After covalent coupling, non-coupled rFel d1 was removed by gel filtration in 150 mM PBS, pH 7.4. The compositions were analyzed by SDS-PAGE and immunoblotting to observe and to confirm coupling bands. For this purpose, samples of SMPH-derivatized VLP CMV-Npadr and CMV-Ntt830, the compositions rFel d1-CMV-Npadr and rFel d1-CMV-Ntt830 and Fel d1 protein were loaded in parallel on a gel. Coupling was observed by immunoblotting using an anti-penta His antibodies binding to the His tag of the protein Fel d1. Visible bands indicated Fel d1 protein as well as the SMPH-derivatized VLP CMV-Npadr, VLP CMV-Ntt830, and the compositions rFel d1-CMV-Npadr and rFel d1-CMV-Ntt830 all of which were easily distinguished by their size. In addition, a SDS-PAGE gel was stained with Coomassie blue and coupling was observed and confirmed.

Immunization of Mice with rFel d1 Coupled to CMV-Npadr and CMV-Ntt830

Groups of five female Balb/c mice were either immunized with CMV-Npadr VLP and CMV-Ntt830 VLP coupled via SMPH to rFel d1. An amount of 5 µg rFel d1-CMV-Npadr and rFel d1-CMV-Ntt830, respectively, were diluted in 150 mM PBS, pH 7.4 to 150 µl and injected intraveneously on day 0 and day 7. Mice were bled on days 0 (pre-immune), day 7, day 14, and day 25, and sera were analyzed using Fel d1 specific ELISA.

ELISA

The antibody response in mouse sera were analyzed at the indicated time. Antibodies specific for Fel d1 were analyzed by coating ELISA plates with a concentration of 1 µg/ml in a volume of 100 µl in PBS (pH 7.2) at 4° C. overnight. ELISA plates were washed 5× with 200 µl PBS containing 0.05% TWEEN20 (pH 7.2, PBST). In order to avoid unspecific binding the ELISA plates were blocked with 200 µl of 2% BSA in PBST and incubated for 2 hours at RT. The serum samples were diluted in 2% BSA/PBST. Pre-diluted sera were transferred onto the coated plates and further serial diluted to obtain antibody titers based on OD50 calculation. After 2 hours of incubation at RT, the ELISA plates were washed 5× with 200 µl of PBST. Binding of serum antibodies was detected by horse-radish peroxidase-conjugated goat anti-mouse IgG (Jackson ImmunoResearch). The detection antibody was diluted 1:1000 in 2% BSA/PBST and a volume of 100 µl per sample was transferred. The plates were incubated for 1 hour at RT. ELISA plates were washed as described before. Prior washing the substrate solution was prepared. To this end, 1 tablet (10 mg) of OPD (1,2-Phenylenediamine dihydrochloride) and 9 µl of 30% H2O2 was dissolved in 25 ml citric acid buffer (0.066 M Na2HPO4, 0.035 M citric acid, pH 5.0). A volume of 100 µl of the substrate solution was pipetted onto the plates and exactly incubated for 7 minutes at RT. To stop the reaction 50 µl of stop solution (5% H2SO4 in H2O) was directly pipetted onto the plates. Absorbance readings at 450 nm of the 1, 2-Phenylenediamine dihydrochloride color reaction were analyzed. FIG. 8 shows that antibodies specific for Fel d1 were induced in mice with the inventive compositions rFel d1-CMV-Npadr (FIG. 8A) and rFel d1-CMV-Ntt830 (FIG. 8B).

Example 9

Coupling of α-Synuclein Peptide to CMV-Ntt830 and Induction of Immune Response

Coupling of the α-synuclein peptide of SEQ ID 22 to the VLPs formed from CMV-Ntt830 (SEQ ID NO: 6) was performed as follows. A solution of 1 ml of 1 mg/ml CMV-Ntt830 in 20 mM HEPES, 50 mM NaCl, pH 7.3 was reacted for 60 min at room temperature with 79.3 µl of a SMPH solution (10 mM in DMSO). Also, a solution of 1 ml of 1 mg/ml CMV-Ntt830 in 20 mM HEPES, 50 mM NaCl, pH 7.3 was reacted for 60 min at room temperature with 79.3 µl of a Sulfo-KMUS solution (10 mM in 20 mM HEPES, pH 7.4). The reactions were dialysed at 4° C. against three times of 2 L of 20 mM HEPES, 50 mM NaCl, pH 7.3 for 2 h, 14 h and 2 h in a SLIDE-A-LYZER dialysis cassette with a MWCO of 10 kDa. 800 µl of the derivatized and dialyzed CMV-Ntt830 solutions were mixed with 21.5 µl of α-synuclein peptide (22.32 mg/ml) and incubated for 3 h at RT for chemical cross-linking at 500 rpm on a shaking Eppendorf Thermomixer. The coupling reactions were cleared by centrifugation at 20000×g for 10 min at 4° C. Derivatized CMV-Ntt830 coat protein and coupled products were analyzed by SDS-PAGE analysis under reducing conditions on a NUPAGE 4-12% Bis-Tris gel. Subsequently, a densitometric analysis of the Coomassie-stained gel was performed. Several bands showing increased molecular weight with respect to the CMV-Ntt830 coat monomer were visible, clearly demonstrating the successful cross-linking of the α-synuclein peptide to the CMV-Ntt830 (Coomassie-stained NUPAGE, not shown). Coupling density was above 1.0 and coupling efficiency was around 60%. To proof the integrity of the CMV-Ntt830 VLP after derivatization and coupling, derivatized CMV-Ntt830 and coupled products were analyzed by 1% agarose gel electrophoresis in 1×TAE followed by Coomassie- and ethidium bromide-stain. Protein- and nucleic acid bands of derivatized and coupled CMV-Ntt830 VLP, respectively, co-migrate and display a similar migration behavior as non-derivatized and non-coupled CMV-Ntt830. The co-migration between coat protein and nucleic acids clearly demonstrated that the CMV-Ntt830 VLPs were still intact and that no nucleic acid was released from the CMV-Ntt830 VLPs.

Immunization of Mice with α-Synuclein Derived-Peptide Coupled to CMV-Ntt830 Coat Protein Groups of four female C57B/6 mice were immunized with CMV-Ntt830 VLPs coupled via SMPH to α-synuclein peptide (SEQ ID NO: 22). An amount of 250 µg of total protein were diluted in 150 mM PBS, pH 7.4 to 150 µl and injected i.v. on day 0 and day 14. Mice were bled on days 0 (pre-immune), day 7, day 14, day 21, day 28 and day 34, and sera were analyzed using α-synuclein specific ELISA.

ELISA

The α-synuclein peptides were coupled to bovine RNAse A using the chemical cross-linker sulfo-SPDP. ELISA plates were coated with α-synuclein peptide-coupled RNAse preparations at a concentration of 5 µg/ml. The plates were blocked and then incubated with serially diluted mouse sera. Bound antibodies were detected with enzymatically labeled anti-mouse IgG. As a control, pre-immune sera of the same mice were also tested. All mice made a clear and strong IgG response against the α-synuclein derived peptide seen in FIG. 9.

Example 10

Coupling of IL-17A Peptide to CMV-Ntt830 and Induction of Immune Response

Coupling of murine IL17A protein (SEQ ID NO: 20) to CMV-Ntt830 coat protein (SEQ ID NO:6) was performed. The mIL-17 protein was covalently conjugated to CMV-Ntt830 by a two-step procedure. First, CMV-Ntt830 VLPs (2 mg/ml in 50 mM NaH2PO4, 10% glycerol, pH 7.4) were reacted at RT for 60 min with an equimolar amount of the heterobifunctional chemical cross-linker, succinimidyl-6-(β-maleimidopropionamido)hexanoate (SMPH). Unreacted cross-linker was removed by gel filtration with a PD-10 desalting column using the same buffer (50 mM NaH2PO4, 10% glycerol, pH 7.4). Prior to the conjugation step, purified mIL-17 protein was incubated for 5 min at RT with a 10-fold excess of tri(2-carboxyethyl)phosphine hydrochloride (TCEP-HCl) to reduce any cysteine residues in the linker. Then mIL-17 protein was covalently linked to the derivatized VLPs by reacting equimolar amounts of mIL-17 protein and VLP for 3 h at RT. The vaccine was analyzed by SDS-PAGE followed by Coomassie-staining and immunoblotting with anti-His antibodies. The intensities of Coomassie blue-stained bands corresponding to the various components of the coupling reaction are determined by densitometry and are used to calculate coupling efficiency. Monomeric, derivatized CMV-Ntt830 migrated as a discrete 28 kDa band while the CMV-Ntt830-mIL-17 conjugate migrated at 45 kDa (28 kDa CMV-Ntt830 monomer+17 kDa mIL-17 protein). The analysis by SDS-PAGE and Coomassie-staining visualized several bands of increased molecular weight with respect to the CMV-Ntt830 coat protein indicating the successful cross-linking of the IL-17 protein to the CMV-Ntt830 VLP. Coupling efficiency was defined as the molar ratio of CMV-Ntt830 monomers coupled to mIL-17 (45 kDa band) to total CMV-Ntt830 monomers (sum of 28 and 45 kDa bands). Coupling efficiency was determined to be at least 15.3% equaling one molecule mIL-17 per 6.5 molecules CMV-Ntt830. The coupling efficiency calculated in this way is a minimum estimate of the degree of coupling, because it does not take into account CMV-Ntt830 monomers coupled to more than one mIL-17 molecule. Thus, proteins of interest such as IL-17A can be efficiently coupled to CMV-Ntt830 VLPs.

Immunization of Mice with Mouse IL17A Protein Coupled to CMV-Ntt830 VLP

A group of 3 female BALB/c mice were immunized with CMV-Ntt830 coat protein coupled to mouse IL17A protein. Twenty µg of total protein were diluted in PBS, pH 7.4 to 150 µl and injected intravenously on day 0, day 14. Mice were bled on days 0 (pre-immune), day 7, day 14, day 21, and day 34 and sera were analyzed using mouse IL17A-specific ELISA.

ELISA

ELISA plates were coated with mouse IL17A, at a concentration of 1 µg/ml. The plates were blocked and then incubated with serially diluted mouse sera from day 0, 4, 14, 21 and 34. Bound antibodies were detected with enzymatically labeled anti-mouse IgG antibody. Antibody titers of mouse sera were calculated as the average of those dilutions which led to half maximal optical density at 450 nm. Mice immunized with CMV-Ntt830 VLP coupled to IL17A mounted a strong immune response against IL17 protein (FIG. 10).

Detection of Neutralizing Antibodies

Sera of mice immunized with mouse IL17 coupled to CMV-Ntt830 as described above is then tested for their ability to inhibit the binding of mouse IL17A protein to IL-17 receptor. ELISA plates are therefore coated with mouse IL-17 receptor A protein at a concentration of 1 µg/ml. Serial dilutions of mouse sera from day 35 mouse were pre-incubated with 10 µg/ml biotinylated mouse IL-17A for one hour and then added to the IL-17 receptor A coated plates. Binding of IL 17 to the coated receptor is detected with horse radish peroxidase conjugated to streptavidin. Neutralizing antibody titers are calculated as the average of those serum dilutions which led to half maximal optical density at 450 nm.

Efficacy of CMV-Ntt830-mIL17A by Amelioration of Experimental Autoimmune Encephalitis in a Mouse Model for Multiple Sclerosis Female SJL mice are immunized as described above and are injected subcutaneously with 100 µg PLP peptide mixed with complete Freund's adjuvant one week after the last immunization. On the same day all mice are injected intraperitoneally with 400 µg of pertussis toxin. Mice are scored on a daily basis for development of neurological symptoms according to the following scheme: 0, no clinical disease; 0.5, end of tail limp; 1, tail completely limp; 1.5, limp tail and hind limb weakness (unsteady gait and poor grip of hind legs); 2, unilateral partial hind limb paralysis; 2.5, bilateral partial hind limb paralysis; 3, complete bilateral hind limb paralysis; 3.5, complete bilateral hind limb paralysis and unilateral front limb paralysis; 4, total paralysis of hind and front limbs. The average clinical scores are assessed for mice which are immunized with CMV-Ntt830-mIL17A or CMV-Ntt830 as described above. CMV-Ntt830-mIL 17 A-immunized mice show significantly reduced clinical symptoms between days 53 and 61 compared to CMV-Ntt830-immunized mice. This demonstrates that the anti-IL-17 antibodies generated by immunization with CMV-Ntt830-mIL17A are able to improve the clinical symptoms in a mouse model of multiple sclerosis.

Example 11

Coupling of Murine IL-5 to CMV-Ntt830 and Induction of Immune Response

IL-5 was expressed and purified as described (Zou Y, et al., Vaccine 28 (2010) 3192-3200). Coupling of mIL-5 (SEQ ID NO:23) to the VLP CMV-Ntt830 with the modified CP of SEQ ID NO:6 was performed as follows. In order to be coupled to IL-5 CMV-Ntt830 VLPs were first derivatized with 30-fold excess of a heterobifunctional chemical crossliker, succinimidyl-6-($\beta$3-maleimidopropionamido)hexanoate (SMPH). The unbound SMPH was removed by dialysis against PBS. rIL-5 was reduced for 1 h with an equimolar amount of tri(2-carboxyethyl)phosphine hydrochloride (TCEP) in PBS (pH 8.0). Reduced rIL-5 (80 µM) was incubated for 4 h at 22° C. with 40 µM of SMPH derivatized CMV-Ntt830. The reaction was dialysed 12 h against PBS pH 8.0.

Immunization of Mice with IL-5 Derived-Peptides Coupled to VLPs of CMV-Ntt830 Modified Coat Protein Groups of four female Balb/c mice were either immunized with CMV-Ntt830 VLPs coupled via SMPH to IL-5 (SEQ ID NO:23). 50 µg of total protein were diluted in 20 mM HEPES, 50 mM NaCl, pH 7.3 to 200 µl and injected subcutaneously (100 µl on two ventral sides) on day 0 and day 14. Mice were bled on days 0 (pre-immune), day 14, and day 21, and sera were analyzed using IL-5 and CMV-Ntt830-specific ELISA.

ELISA

ELISA plates were coated either with IL-5 at a concentration of 10 µg/ml or CMV-Ntt830 VLPs at a concentration of 2 µg/ml. The plates were blocked and then incubated with serially diluted mouse sera. Bound antibodies were detected with enzymatically labeled anti-mouse IgG. As a control, pre-immune sera of the same mice were also tested (data not shown). All mice made a clear and strong IgG response against the peptides as well as CMV-Ntt830

OVA Based Model of Allergic Airway Inflammation

To induce allergic airway inflammation, female BALB/c mice (5 per group) were injected (i.p.) with 10 µg of OVA (Grade V, Sigma-Aldrich) mixed with 2 mg of alum (Aluminium Hydroxide Gel Adjuvant, Brenntag Biosector, Denmark). 10 days later, mice were challenged daily with 100 µg of OVA by intranasal administration for 4 days. 24 hours after the last challenge, BAL and lungs were subjected to histology. Mice injected i.p. with OVA and alum but not challenged intranasally with OVA served as a negative control for disease induction in these experiments.

Using this model, mice were immunized twice (d-0, d-14) with 100 µg CMV-Ntt830 VLPs or CMV-Ntt830 VLPs coupled to IL-5. On day 21, mice were sensitized with OVA and on day 31 challenged intranasally with OVA. IL-5 immunized mice had dramatically reduced eosinophil counts bronchoalveolar fluid.

Example 12

Coupling of M2 Peptide to CMV-Ntt830 Virus-Like Particles

A solution of 2 ml of 1 mg/ml CMV-Ntt830 VLPs with the modified CP of SEQ ID NO:6 in PBS/10% glycerol pH 7.2 was reacted for 60 min at room temperature with 42.6 µl of a SMPH solution (150 mM in DMSO). The reaction solution was dialysed at 4° C. against two 2 l changes of 20 mM HEPES/10% glycerol pH 7.2 over 12 and 4 hours. 0.6 ml of the derivatized and dialyzed CMV-Ntt830 solution was mixed with 21.45 µl of a 10 mM DMSO solution of the influenza peptide M2 (SEQ ID NO:24) and incubated 4 h at room temperature for chemical crosslinking resulting in CMV-Ntt830-M2 conjugate vaccine. Uncoupled peptide was removed by dialysis against 20 mM HEPES/10% glycerol pH 7.2 for 12 h and 4 h. The coupled product was analyzed on a 12% Bis-Tris-polyacrylamide gel under reducing conditions. Several bands of increased molecular weight with respect to the CMV-Ntt830 capsid monomer were visible, clearly demonstrating the successful crosslinking of the influenza M2 peptide to the CMV-Ntt830 capsid.

Immunization of Mice with M2 Peptide Coupled to CMV-Ntt830 Capsids (CMV-Ntt830-M2)

Four female Balb/c mice per group were immunized with 40 µg of CMV-Ntt830-M2 vaccine formulated in 200 µl PBS and injected subcutaneously on day 0 and day 20. Mice were bled on day 34 and sera were analyzed using M2-specific and CMV-Ntt830-specific ELISA.

Detection of Anti-M2 Antibodies by ELISA

ELISA plates were coated with M2 peptide (SEQ ID NO:24) at a concentration of 10 µg/ml or with CMV-Ntt830 virus-like particles at a concentration of 10 µg/ml. The plates were blocked and then incubated with serially diluted mouse sera. Bound antibodies were detected with enzymatically labeled anti-mouse IgG antibodies. Antibody titers of mouse sera are defined as the reciprocals of the dilutions leading to 50% of the OD measured at saturation (OD50). The average anti-M2 antibody titers and anti-CMV-Ntt830 titers at day 34 of mice which were >1:10000. The data demonstrate that coupling of M2 peptide to CMV-Ntt830 capsids is strongly enhancing the immunogenicity of the M2 peptide as the M2 peptide alone is not immunogenic.

The efficacy of CMV-Ntt830-M2 immunization was tested in a murine model of influenza infection. Mice were challenged with a lethal dose of 4×LD50 of mouse adapted influenza A/PR/8/34 virus. The virus was diluted in PBS and administered (2×50 µl) via the nose under light anaesthesia with isofuran. Mice, which lost more than 30% body weight or which showed a body temperature equal to or lower than 30° C., were euthanized. The survival of the mice in both groups were as follows: All mice immunized with CMV-Ntt830-M2 survived while all mice immunized with CMV-Ntt830 alone died. The result demonstrates that immunization of mice with M2 peptide coupled to CMV-Ntt830 induces M2 specific antibodies which protect mice against a lethal infection with influenza A/PR/8/34 virus.

Example 13

Coupling of Aβ1-6 Peptide to CMV-Ntt830 Virus-Like Particles

A solution of 2 ml of 1 mg/ml CMV-Ntt830 VLPs with the modified CP of SEQ ID NO:6 in PBS/10% glycerol pH 7.2 was reacted for 60 min at room temperature with 42.6 µl of a SMPH solution (150 mM in DMSO). The reaction solution was dialysed at 4° C. against two 2 l changes of 20 mM HEPES/10% glycerol pH 7.2 over 12 and 4 hours. 0.6 ml of the derivatized and dialyzed CMV-Ntt830 solution was mixed with 21.45 µl of a 10 mM DMSO solution of Aβ1-6 (SEQ ID NO:25) and incubated 4 h at room temperature for chemical crosslinking resulting in CMV-Ntt830—Aβ1-6 conjugate vaccine. Uncoupled peptide was removed by dialysis against 20 mM HEPES/10% glycerol pH 7.2 for 12 h and 4 h. The coupled product was analyzed on a 12% Bis-Tris-polyacrylamide gel under reducing conditions. Several bands of increased molecular weight with respect to the CMV-Ntt830 capsid monomer were visible, clearly demonstrating the successful cross-linking Aβ1-6 peptide CMV-Ntt830.

Immunization of Mice with Aβ1-6 Peptide Coupled to CMV-Ntt830 Capsids (CMV-Ntt830-Aβ1-6)

Four female Balb/c mice per group were immunized with 40 µg of CMV-tt830—Aβ1-6 vaccine formulated in 200 µl PBS and injected subcutaneously on day 0 and day 20. Mice were bled on day 34 and sera were analyzed using Aβ1-6-specific and CMV-Ntt830-specific ELISA.

Detection of Anti-Aβ1-6 Antibodies by ELISA

ELISA plates were coated with Aβ1-6 coupled to RNAse at a concentration of 10 µg/ml or with CMV-Ntt830 virus-like particles at a concentration of 2 µg/ml. The plates were blocked and then incubated with serially diluted mouse sera. Bound antibodies were detected with enzymatically labeled anti-mouse IgG antibodies. Antibody titers of mouse sera are defined as the reciprocals of the dilutions leading to 50% of the OD measured at saturation (OD50). The average anti-Aβ1-6 antibody titers and anti-CMV-Ntt830 titers at day 34 of mice which were >1:10000. The data demonstrate that coupling of Aβ1-6 peptide to CMV-Ntt830 capsids is strongly enhancing the immunogenicity of the Aβ1-6 peptide as the Aβ1-6 peptide alone is not immunogenic. Brain section of human Alzheimer patients were stained with murine sera and plaques became clearly visible.

Example 14

Cloning of Fel d 1 Fusion Proteins

A Fel d1 fusion protein (named F12H6GGC) consisting of chain 1 of Fel d1 fused to the N-terminus of chain 2 of Fel d1 via a 15 amino acid sequence (GGGGS)$_3$ (SEQ ID NO:47) and incorporating a HHHHHHGGC sequence (SEQ ID NO:48) fused to the C-terminus of chain 2 of Fel d1 was produced by oligonucleotide directed gene synthesis. The corresponding oligonucleotide sequence has the sequence of SEQ ID NO:49, wherein the protein sequence of F12H6GGC has the sequence of SEQ ID NO:50:

MEICPAVKRDVDLFLTGTPDEYVEQVAQYKALPVVLENARILKNCVDAKMT

EEDKENALSVLDKIYTSPLCGGGGSGGGGSGGGGSVKMAETCPIFYDVFFA

VANGNELLLDLSLTKVNATEPERTAMKKIQDCYVENGLISRVLDGLVMTTI

SSSKDCMGEAVQNTVEDLKLNTLGRHHHHHHGGC

After synthesis of the gene, it was excised from its helper plasmid and subcloned in frame into NdeI/XhoI sites of the plasmid pET42a(+) (Novagen, USA) resulting in the expression vector pET42-F12H6GGC.

Fel d1 fusion proteins without a hexa-histidine sequence (named F12GGC) were produced by PCR mutagenesis using the plasmid pET42-F12H6GGC as a template. The oligonucleotide primers used in the PCRs to produce these fusion proteins were:

For F12GGC, the forward primer was Fel_BglF (SEQ ID NO:51) and the reverse primer was Feld-dHR (SEQ ID NO:53).

All PCR products were cut with restriction enzymes BglII/XhoI and subcloned back into vector pET42-F126HGGC at the same excision sites. After isolation of plasmid DNA, the introduced changes were confirmed using a BigDye cycle sequencing kit and an ABI PRISM 3100 Genetic analyzer (Applied Biosystems, Carlsbad, USA). The resulting expression vectors was named as pET42-F12GGC. It correspondingly encodes the Fel d1 fusion protein F12GGC (SEQ ID NO: 56).

(SEQ ID NO: 56)
MEICPAVKRDVDLFLTGTPDEYVEQVAQYKALPVVLENARILKNCVDAKMT

EEDKENALSVLDKIYTSPLCGGGGSGGGGSGGGGSVKMAETCPIFYDVFFA

VANGNELLLDLSLTKVNATEPERTAMKKIQDCYVENGLISRVLDGLVMTTI

SSSKDCMGEAVQNTVEDLKLNTLGRGGC

The hexa-histidine sequence enables purification by metal chelate affinity chromatography and the C-terminal sequence comprising GGC or GGCG (SEQ ID NO:58) enables coupling of the Fel d1 fusion proteins to CMV-Ntt830 and CMV-Npadr.

Example 15

Expression and Purification of Fel d 1 Fusion Proteins

Expression of Fel d1 Fusion Proteins in *E. coli*.

The Fel d1-expression vectors pET42-F12H6GGC and pET42-F12GGC were transformed into *E. coli* C2566 cells (New England Biolabs, Ipswich, USA). Clones expressing the highest levels of target protein were selected and used in further experiments. Expression of the various recombinant Fel d1 fusion proteins was performed in the following way. Cultures of *E. coli* harboring expression plasmids were grown in 2×TY medium containing kanamycin (25 mg/l) on a rotary shaker (200 rev/min; Infors, Bottmingen, Switzerland) at 30° C. to an OD600 of 0.8-1.0. Expression of the Fel d1 fusion protein genes was then induced by adding 0.2 mM IPTG. The medium was supplemented with 5 mM $MgCl_2$. Incubation was continued on a rotary shaker at 20° C. for 18 h. The resulting biomass was collected by low-speed centrifugation and frozen at −20° C. until purification.

Purification of Hexa-Histidine-Tagged Fel d1 Fusion Proteins.

For purification of F12H6GGC fusion proteins, the USB PREPEASE Kit (Affymetrix, High Wycombe, UK) was used according to manufacturer's instructions. After thawing on ice, *E. coli* cells from 100 ml culture (approx. 0.75 g) were suspended in 1×LEW buffer containing 5 mM DTT and then disrupted by sonication. Insoluble proteins and cell debris were removed by centrifugation (13,000 rpm, 30 min at 5° C.). The clarified lysate was applied to a Ni-IDA column, washed twice with the same buffer (without DTT) and eluted with 2×1.5 ml of imidazole containing 1×E buffer. The fractions containing Fel d1 were identified by SDS/PAGE (FIG. 11A) and twice dialyzed against 200 volumes of the buffer (20 mM sodium phosphate, 2 mM EDTA, pH 7.0). After dialysis, the protein concentration was estimated using a QUBIT fluorometer in accordance with manufacturer's instructions (Invitrogen, Eugene, USA) or by UV spectrophotometric measurement at 280 nm. The identity of the purified proteins was confirmed by mass spectrometric analysis (FIG. 11B) and by Western blot using anti-His-tag antibodies (Novagen, Cat. No. 71840-3; data not shown).

Purification of Fel d1 Fusion Proteins without Hexa-Histidine Tags.

For purification of F12GGC fusion proteins, anion exchange and hydrophobic interaction chromatography were used. Three grams of IPTG induced *E. coli* were disrupted by sonication in 20 ml of lysis buffer LB (20 mM Tris/HCl pH 8.0, 50 mM NaCl, 5 mM DTT). After sonication the solution was centrifuged for 15 min at 15 000 g and the supernatant collected. Ammonium sulfate was added with constant stirring until 30% saturation was achieved then incubated for 5 min at RT. After centrifugation, solid ammonium sulfate was added to the recovered supernatant until 50% saturation. After centrifugation, protein pellets were collected and dissolved in 2 ml of LB and excess salt removed with a 5 ml HITRAP Desalting Column (GE Healthcare Life Sciences) equilibrated with LB. The desalted protein eluate was loaded onto a 1 ml HITRAP CAPTO DEAE column equilibrated with LB. Bound F12GGC was eluted with an increasing gradient of NaCl. Fractions containing Fel d1 fusion proteins were collected and pooled. The resulting solution was diluted with 4 volumes of 20 mM Tris/HCl pH 8.0, 5 mM DTT and loaded onto a MONOQ 5/50 GL column in LB and eluted with an increasing NaCl gradient. Fractions containing Fel d1 fusion proteins were collected and pooled. 5 M NaCl was added until a concentration of 2.5 M was reached and DTT added to the solution, to maintain a concentration of 5 mM. The Fel d1 containing solution was then loaded onto a 1 ml HITRAP Butyl HP column in 2.5 M NaCl, 5 mM DTT and eluted with a continuously decreasing NaCl concentration. Fractions containing the Fel d1 fusion proteins were collected and pooled. All purification steps were monitored by Coomassie-stained SDS/PAGE gels (FIG. 11C). The identity of purified proteins was confirmed by Western blot using polyclonal antibodies raised against recombinant Fel d1 (data not shown).

Example 16

Authenticity of Recombinant Fel d1 Fusion Protein(s)

Fel d1 Fusion Proteins are Similarly Recognized by Fel d1-Specific Monoclonal Antibodies.

The binding of the Fel d1 fusion protein F12H6GGC and natural Fel d1 (nFel d1) to Fel d1-specific monoclonal antibodies (mAb) was compared using a sandwich ELISA Fel d1 ELISA kit (6F9/3E4) from Indoor biotechnologies (Cardiff, UK). To this end, Nunc ELISA plates were coated with the anti-Fel d1 mAb 6F9 (at 1 microg/ml) at 4° C. overnight. Plates were washed with PBS containing 0.05% TWEEN 20 (PBST) and blocked with Superblock (Invitrogen) for 2 h at room temperature (RT). Natural Fel d1 as well as F12H6GGC (1 µg/ml) were serially diluted 1:3 and incubated for 2 h at RT. Plates were washed with PBST and biotinylated anti-Fel d1 mAb 3E4 (at 1 µg/ml) was added and incubated for 1 h at RT. Detection utilized Streptavidin conjugated to horse radish peroxidase (HRPO). To this end, plates were washed with PBST then Streptavidin-Peroxidase (Sigma, 1:1000 dilution) was added to the plates for 30 min at RT. Detection was performed with OPD substrate solution and 5% $H_2SO_4$ as stop solution. The absorbance was measured using an ELISA reader (BioRad) at 450 nm.

Natural Fel d1 and F12H6GGC gave similar titers in the ELISA which demonstrates they were similarly recognized by Fel d1-specific mAbs thus confirming the authenticity of the recombinant Fel d1 F12H6GGC (FIG. 12).

Recombinant Fel d1 Fusion Proteins Activate Basophils in Whole Blood of Cat Allergic Patients.

Blood of cat allergic patients contain basophils which carry Fel d1-specific IgE antibodies on their surface, which upon allergen exposure crosslink the FcεRI and cause degranulation. To check the ability of recombinant Fel d1 to cause degranulation, whole blood from an Fel d1-allergic patients was collected and used in combination with recombinant Fel d1 fusion protein F12H6GGC in a Basophil Activation Test kit of Bühlmann Laboratories (FLOW CAST, FK CCR). This assay measures up-regulation of an exclusive degranulation marker CD63 on CCR3+ basophils. Briefly, 100 µl of stimulation buffer was mixed with 50 µl of EDTA-treated whole blood. In addition, 50 µl of various dilutions of natural Fel d1 or recombinant Fel d1 fusion protein F12H6GGC were added. Positive control solutions including a mAb against FcεRI as well as an unspecific cell activator (fMLP) were also tested in the assay. Staining dye (20 µl per sample), containing anti-CCR3 Ab labeled to PE and anti-CD63 Ab labeled to FITC, was added and incubated at 37° C. for 25 min. Erythrocytes were subsequently lysed adding lysis buffer. After 10 min incubation, the samples were centrifuged at 500×g for 5 min and washed with wash buffer (PBS containing 2% FCS). After a second centrifugation step, the cell pellets were suspended in 200 μl wash buffer and acquired using a flow cytometer (FACSCALIBUR). The samples were analyzed with CELLQUEST Pro software. The percentage of the CD63 expression on CCR3+ basophils was analyzed.

Recombinant Fel d1 fusion proteins was found to readily trigger degranulation of basophils from cat allergic patients. Moreover, when compared to natural Fel d1, similar levels of degranulation were achieved thus demonstrating authenticity of the recombinantly produced Fel d1 fusion proteins. (FIG. 13A/FIG. 13B).

Example 17

Coupling of Fel d1 Fusion Proteins to CMV-Ntt830 and CMV-VLPs

The Fel d1 fusion protein F12H6GGC was covalently linked to CMV-Ntt830 and CMV-Npadr VLPs using the heterobifunctional chemical cross-linker succinimidyl-6-[(β-maleimidopropionamido) hexanoate] (SMPH) in the following way.

CMV-Ntt830 and CMV-Npadr virus-like particles stored in 5 mM Na-borate, 2 mM EDTA buffer, pH 9.0, were subject to buffer exchange with 20 mM Na-phosphate containing 30% sucrose and 2 mM EDTA using PD10 columns (GE Healthcare). A solution of CMV-Npadr or CMV-Ntt830 VLPs reacted for 60 min at RT with 7.5× molar excess of heterobifunctional crosslinker SMPH. Unreacted SMPH was removed with PD10 columns in 20 mM Na-phosphate containing 30% sucrose and 2 mM EDTA.

Fel d1 fusion protein F12H6GGC was treated with 10× molar excess TCEP (Thermo Fisher). Derivatized CMV-Ntt830 and CMV-Npadr-VLPs were reacted with 1× or 2× molar excess of recombinant Fel d1 fusion protein F12H6GGC for 3 h at 23° C. The coupling reaction was analyzed by reducing SDS-PAGE (NUPAGE 4-12% Bis-Tris gel) stained with Coomassie Blue. Protein bands with masses of approximately 44.5 kDa and 69 kDa were evident after the chemical conjugation reaction (data not shown). These bands correspond to the CMV coat protein (24.5 kDa) covalently linked with the Fel d1 fusion protein F12H6GGC (20 kDa) and two CMV coat protein molecules covalently linked with (49 kDa) one Fel d1 fusion protein F12H6GGC respectively indicating the formation of Fel d1-CMV VLPs.

Example 18

Immune Response to Fel d1-CMV VLP in Mice

Groups of three female Balb/c mice were immunized with either Fel d1-CMV-Ntt830-VLP, prepared as described in Example 10, or CMV-Ntt830-VLP simply mixed with Fel d1 fusion protein F12H6GGC. Both compositions contain the same amount of the Fel d1 fusion protein. 10 µg of each composition was prepared in 150 mM PBS, pH 7.4 and injected in a volume of 150 µl intravenously on day 0 and day 14. Mice were bled on days 0 (pre-immune), day 14 and 21, and sera were analyzed by ELISA for natural Fel d1 specific IgG-antibodies.

NUNC ELISA plates were coated with natural Fel d1 (Indoor Biotechnologies) in PBS with a concentration of 1 µg/ml overnight at 4° C. The plates were blocked with Superblock (Invitrogen). A serial dilution of the sera was performed in order to detect OD50. OD50 describes the reciprocal of the dilution, which reaches half of the maximal OD value. IgG-antibodies specific for Fel d1 were detected with an anti-mouse IgG antibody directly labeled to horseradish dish peroxidase (HRPO) (Jackson). The conversion of o-phenylenediamine dihydrochloride (OPD) by the HRPO was measured as color reaction at 450 nm, which was stopped by adding 5% sulfuric acid ($H_2SO_4$) after 7 minutes incubation.

Only after a single immunization, Fel d1-specific IgG antibodies were detected in mice (on day 14). The response was boosted by a second injection. Fel d1-CMV VLPs significantly increased the induction of Fel d1 specific IgG antibodies compared to the mixed compositions demonstrating the immune-enhancing effect of chemical conjugation of the Fel d1 fusion proteins to the VLP (FIG. 14).

Example 19

Coupling of Human IL-1β to CMV-Ntt830 and CMV-VLPs

The human IL-1β mature protein (SEQ ID NO:60) was covalently linked to CMV-Ntt830 and CMV-Npadr VLPs using the heterobifunctional chemical cross-linker succinimidyl-6-[(β-maleimidopropionamido) hexanoate] (SMPH) in the following way.

CMV-Ntt830 and CMV-Npadr virus-like particles stored in 5 mM Na-borate, 2 mM EDTA buffer, pH 9.0, were subject to buffer exchange with 20 mM Na-phosphate containing 30% sucrose and 2 mM EDTA using PD10 columns (GE Healthcare) A solution of CMV-Npadr or CMV-Ntt830 VLPs reacted for 60 min at RT with 7.5× molar excess of heterobifunctional crosslinker SMPH. Unreacted SMPH was removed with PD10 columns in 20 mM Na-phosphate containing 30% sucrose and 2 mM EDTA.

The IL-1β protein was treated with 5× molar excess TCEP (Thermo Fisher). Derivatized CMV-Ntt830 and CMV-Npadr-VLPs were reacted with 1× or 2× molar excess of human IL1β for 3 h at 23° C. The coupling reaction was analyzed by reducing SDS-PAGE (NUPAGE 4-12% Bis-Tris gel) stained with Coomassie Blue. Protein bands with masses of approximately 41.5 kDa and 66 kDa were evident after the chemical conjugation reaction (data not shown). These bands correspond to the CMV coat protein (24.5 kDa) covalently linked with the IL1β protein (17 kDa) and two CMV coat protein molecules (49 kDa) covalently linked with one IL1β protein respectively indicating the formation of IL1β-CMV VLPs.

Example 20

Coupling of Canine IL-5 to CMV-Ntt830 and Induction of Immune Response

Canine IL-5 (cIL-5) (SEQ ID NO:61) is modified to contain a free Cys expressed analogously as described for murine IL-5 in Zou Y, et al., Vaccine 28 (2010) 3192-3200. Coupling of the so modified cIL-5 to the VLP CMV-Ntt830 is performed as follows. In order to be coupled to cIL-5 CMV-Ntt830 VLPs are first derivatized with 30-fold excess of a heterobifunctional chemical cross-liker, succinimidyl-6-(β-maleimidopropionamido)hexanoate (SMPH). The unbound SMPH is removed by dialysis against PBS. cIL-5 was reduced for 1 h with an equimolar amount of tri(2-carboxyethyl)phosphine hydrochloride (TCEP) in PBS (pH 8.0). Reduced cIL-5 (80 µM) was incubated for 4 h at 22° C.

with 40 µM of SMPH derivatized CMV-Ntt830. The reaction was dialysed 12 h against PBS pH 8.0.

Immunization of Dogs with cIL-5 Coupled to VLPs of CMV-Ntt830

Groups of four female outbread dogs are immunized with CMV-Ntt830 VLPs coupled via SMPH to cIL-5 as described above. 50 µg of the composition are diluted in 20 mM HEPES, 50 mM NaCl, pH 7.3 to 500 µl and injected subcutaneously on day 0 and day 14. Dogs are bled on days 0 (pre-immune), day 14, and day 21, and sera are analyzed using cIL-5 and CMV-Ntt830-specific ELISA.

ELISA

ELISA plates are coated either with cIL-5 at a concentration of 10 µg/ml or CMV-Ntt830 VLPs at a concentration of 2 µg/ml. The plates are blocked and then incubated with serially diluted mouse sera. Bound antibodies are detected with enzymatically labeled anti-canine IgG. As a control, pre-immune sera of the same dogs are also tested (data not shown). All dogs make a clear and strong IgG response against cIL-5 as well as CMV-Ntt830.

Example 21

Coupling of Canine IL-4 to CMV-Ntt830 and Induction of Immune Response

Canine IL-4 (cIL-4) (SEQ ID NO:62) is modified to contain a free Cys expressed analogously to as described for murine IL-5 in Zou Y, et al., Vaccine 28 (2010) 3192-3200. Coupling of the so modified cIL-4 to the VLP CMV-Ntt830 is performed as follows. In order to be coupled to cIL-4 CMV-Ntt830 VLPs are first derivatized with 30-fold excess of a heterobifunctional chemical cross-liker, succinimidyl-6-(β-maleimidopropionamido)hexanoate (SMPH). The unbound SMPH is removed by dialysis against PBS. cIL-4 was reduced for 1 h with an equimolar amount of tri(2-carboxyethyl)phosphine hydrochloride (TCEP) in PBS (pH 8.0). Reduced cIL-4 (80 µM) was incubated for 4 h at 22° C. with 40 µM of SMPH derivatized CMV-Ntt830. The reaction was dialysed 12 h against PBS pH 8.0.

Immunization of Dogs with cIL-4 Coupled to VLPs of CMV-Ntt830

Groups of four female outbread dogs are immunized with CMV-Ntt830 VLPs coupled via SMPH to cIL-4 as described above. 50 µg of the composition are diluted in 20 mM HEPES, 50 mM NaCl, pH 7.3 to 500 µl and injected subcutaneously on day 0 and day 14. Dogs are bled on days 0 (pre-immune), day 14, and day 21, and sera are analyzed using cIL-4 and CMV-Ntt830-specific ELISA.

ELISA

ELISA plates are coated either with cIL-4 at a concentration of 10 µg/ml or CMV-Ntt830 VLPs at a concentration of 2 µg/ml. The plates are blocked and then incubated with serially diluted dog sera. Bound antibodies are detected with enzymatically labeled anti-canine IgG. As a control, pre-immune sera of the same dogs are also tested (data not shown). All dogs make a clear and strong IgG response against cIL-4 as well as CMV-Ntt830.

Example 22

Coupling of Canine IL-13 to CMV-Ntt830 and Induction of Immune Response

Canine IL-13 (cIL-13) (SEQ ID NO:63) is modified to contain a free Cys and expressed analogously to as described for murine IL-5 in Zou Y, et al., Vaccine 28 (2010) 3192-3200. Coupling of the so modified cIL-13 to the VLP CMV-Ntt830 is performed as follows. In order to be coupled to cIL-13 CMV-Ntt830 VLPs are first derivatized with 30-fold excess of a heterobifunctional chemical cross-liker, succinimidyl-6-(β-maleimidopropionamido)hexanoate (SMPH). The unbound SMPH is removed by dialysis against PBS. cIL-13 was reduced for 1 h with an equimolar amount of tri(2-carboxyethyl)phosphine hydrochloride (TCEP) in PBS (pH 8.0). Reduced cIL-13 (80 µM) was incubated for 4 h at 22° C. with 40 µM of SMPH derivatized CMV-Ntt830. The reaction was dialysed 12 h against PBS pH 8.0.

Immunization of Dogs with cIL-13 Coupled to VLPs of CMV-Ntt830

Groups of four female outbread dogs are immunized with CMV-Ntt830 VLPs coupled via SMPH to cIL-13 as described above. 50 µg of the composition are diluted in 20 mM HEPES, 50 mM NaCl, pH 7.3 to 500 µl and injected subcutaneously on day 0 and day 113. Dogs are bled on days 0 (pre-immune), day 14, and day 21, and sera are analyzed using cIL-13 and CMV-Ntt830-specific ELISA.

ELISA

ELISA plates were coated either with cIL-13 at a concentration of 10 µg/ml or CMV-Ntt830 VLPs at a concentration of 2 µg/ml. The plates are blocked and then incubated with serially diluted canine sera. Bound antibodies are detected with enzymatically labeled anti-canine IgG. As a control, pre-immune sera of the same dogs are also tested (data not shown). All dogs make a clear and strong IgG response against cIL-13 as well as CMV-Ntt830.

Example 23

Coupling of Human IL-31 to CMV-Ntt830 and Induction of Immune Response

Human IL-31 (hIL-31) (SEQ ID NO:43) is modified to contain a free Cys and expressed analogously to as described for murine IL-5 in Zou Y, et al., Vaccine 28 (2010) 3192-3200. Coupling of the so modified hIL-31 to the VLP CMV-Ntt830 is performed as follows. In order to be coupled to hIL-31 CMV-Ntt830 VLPs are first derivatized with 30-fold excess of a heterobifunctional chemical cross-liker, succinimidyl-6-(β-maleimidopropionamido)hexanoate (SMPH). The unbound SMPH is removed by dialysis against PBS. hIL-31 was reduced for 1 h with an equimolar amount of tri(2-carboxyethyl)phosphine hydrochloride (TCEP) in PBS (pH 8.0). Reduced hIL-31 (80 µM) is incubated for 4 h at 22° C. with 40 µM of SMPH derivatized CMV-Ntt830. The reaction was dialysed 12 h against PBS pH 8.0.

Immunization of Mice with hIL-31 Coupled to VLPs of CMV-Ntt830

Groups of four female BALB/c mice are immunized with CMV-Ntt830 VLPs coupled via SMPH to IL-31 as described above. 50 µg of the composition are diluted in 20 mM HEPES, 50 mM NaCl, pH 7.3 to 500 µl and injected subcutaneously on day 0 and day 113. Dogs are bled on days 0 (pre-immune), day 14, and day 21, and sera are analyzed using hIL-31 and CMV-Ntt830-specific ELISA.

ELISA

ELISA plates were coated either with hIL-31 at a concentration of 10 μg/ml or CMV-Ntt830 VLPs at a concentration of 2 μg/ml. The plates are blocked and then incubated with serially diluted mouse sera. Bound antibodies are detected with enzymatically labeled anti-mouse IgG. As a control, pre-immune sera of the same mice are also tested (data not shown). All mice make a clear and strong IgG response against hIL-31 as well as CMV-Ntt830.

---

The invention claimed is:

1. A composition comprising:
   (a) a modified virus-like particle (VLP) of cucumber mosaic virus (CMV), wherein said modified VLP of CMV comprises at least one modified CMV polypeptide, wherein said modified CMV polypeptide comprises
      i. a CMV polypeptide, wherein said CMV polypeptide comprises
         (x) an amino acid sequence of a coat protein of CMV; or
         (y) mutated amino acid sequence, wherein the amino acid sequence to be mutated is an amino acid sequence of a coat protein of CMV, and wherein said mutated amino acid sequence and said coat protein of CMV show a sequence identity of at least 90%; and
      ii. a T helper cell epitope; wherein said T helper cell epitope replaces a N-terminal region of said CMV polypeptide, wherein said N-terminal region of said CMV polypeptide corresponds to amino acids 2-12 of SEQ ID NO:1;
   and wherein said modified virus-like particle comprises at least one first attachment site; and
   (b) at least one antigen, wherein said antigen comprises at least one second attachment site; and
   wherein said antigen is selected from
   a) IL-17;
   b) IL-17, wherein said antigen comprises SEQ ID NO:42;
   c) human IL-5 and canine IL-5;
   d) IL-5, wherein said antigen comprises SEQ ID NO:41;
   e) TNFα;
   f) IL-1α;
   g) IL-13
   h) IL-13, wherein said antigen comprises SEQ ID NO:46;
   i) a peptide derived from Aβ1-42;
   j) IgE or a peptide or domain comprised in IgE;
   k) α-synuclein or a peptide derived from α-synuclein
   l) α-synuclein or a peptide derived from α-synuclein, wherein said peptide consists of 6 to 14 amino acids, and wherein said antigen is a peptide derived from α-synuclein selected from any one of SEQ D NO:32, SEQ ID NO:33 and SEQ ID NO:34;
   m) IL-4
   n) IL-4, wherein said antigen comprises SEQ ID NO:45;
   o) GnRH;
   p) the extracellular domain of Influenza A virus M2 protein, or an antigenic fragment thereof;
   q) human IL-31, canine IL-31 and feline IL-31;
   r) human IL-31, wherein said antigen comprises SEQ ID NO:43;
   s) canine IL-31, wherein said antigen comprises SEQ ID NO:44
   t) an antigen derived from *Plasmodium falciparum* or *Plasmodium Vivax*, or wherein said antigen is the derived from RSV;
   u) IL-1β;
   v) IL-1β, wherein said antigen comprises SEQ ID NO:60;
   w) the dog allergen Can f1 or Can f2;
   x) calcitonin gene-related peptide (CGRP); and
   y) Amylin;
   wherein (a) and (b) are linked through said at least one first and said at least one second attachment site.

2. The composition of claim 1, wherein said first attachment site and said second attachment site are linked via at least one covalent peptide-bond or via at least one covalent non-peptide-bond.

3. The composition of claim 1 further comprising at least one immunostimulatory substance, wherein said immunostimulatory substance is packaged into said modified virus-like particle, and wherein said immunostimulatory substance is an unmethylated CpG-containing oligonucleotide.

4. A pharmaceutical composition comprising:
(a) the composition of claim 1; and
(b) a pharmaceutically acceptable carrier, diluent and/or excipient.

5. A method for inducing an immune response in an animal or human comprising administering the composition of claim 1 to said animal or said human.

6. The method of claim 5, wherein said antigen is selected from
(a) IL-17, human or canine IL-5, TNFα, IL-1α, IL-1 or 11-4;
(b) a peptide derived from Aβ-1-42;
(c) IgE or a peptide or domain comprised in IgE;
(d) α-synuclein or a peptide derived from α-synuclein;
(e) GnRH;
(f) the extracellular domain of Influenza A virus M2 protein, or an antigenic fragment thereof;
(g) an antigen derived from Plasmodium falciparum or *Plasmodium Vivax*;
(h) an antigen derived from RSV;
(i) the dog allergen Can f1 or Can f2;
(j) calcitonin gene-related peptide (CGRP); and
(k) Amylin.

7. The composition of claim 1, wherein said CMV polypeptide comprises
(a) an amino acid sequence of a coat protein of CMV, wherein said amino acid sequence comprises SEQ ID NO:1 or
(b) an amino acid sequence having a sequence identity of at least 90% of SEQ ID NO:1; and
wherein said amino sequence as defined in (a) or (b) in this claim comprises SEQ ID NO:21; or
wherein said amino sequence as defined in (a) or (b) in this claim comprises an amino acid sequence region, wherein said amino acid sequence region has a sequence identity of at least 90% with SEQ ID NO:21.

8. The composition of claim 1, wherein the number of amino acids of said N-terminal region replaced is equal to or lower than the number of amino acids of which said T helper cell epitope consists.

9. The composition of claim 1, wherein said T helper cell epitope is a universal T helper cell epitope.

10. The composition of claim 1, wherein said T helper cell epitope consists of at most 20 amino acids.

11. The composition of claim 1, wherein said Th cell epitope is a PADRE sequence.

12. The composition of claim 1, wherein said Th cell epitope comprises the amino acid sequence of SEQ ID NO:5.

13. The composition of claim 1, wherein said Th cell epitope is derived from tetanus toxin.

14. The composition of claim 1, wherein said Th cell epitope comprises the amino acid sequence of SEQ ID NO:4.

15. The composition of claim 1, wherein said CMV polypeptide comprises an amino acid sequence of a coat protein of CMV, wherein said amino acid sequence comprises (a) SEQ ID NO:1 or (b) an amino acid sequence having a sequence identity of at least 95% of SEQ ID NO:1; and wherein said amino sequence (a) or (b) comprises SEQ ID NO:21.

16. The composition of claim 1, wherein said modified CMV polypeptide comprises an amino acid sequence of SEQ ID NO:6.

17. The composition of claim 1, wherein said modified CMV polypeptide comprises an amino acid sequence of SEQ ID NO:7.

18. The composition of claim 1, wherein said T helper cell epitope is selected from any one of sequences SEQ ID NO:4, SEQ ID NO:5 and SEQ ID NOs:26-30.

19. The composition of claim 1, wherein said T helper cell epitope is SEQ ID NO:4.

20. The composition of claim 1, wherein said T helper cell epitope is SEQ ID NO:5.

* * * * *

UNITED STATES PATENT AND TRADEMARK OFFICE
CERTIFICATE OF CORRECTION

PATENT NO. : 11,324,836 B2
APPLICATION NO. : 16/696161
DATED : May 10, 2022
INVENTOR(S) : Martin Bachmann, Andris Zeltins and Paul Pumpens Page 1 of 1

It is certified that error appears in the above-identified patent and that said Letters Patent is hereby corrected as shown below:

On the Title Page

After Item (71) Applicant, replace "SAIBA AG, Rämishmühle, CH" with --SAIBA AG, Pfaffikon, CH--

In the Claims

Claim 1:
Column 110, Lines 35, 40, 46 and 56: Items 9), k), m) and s) include --;-- at the end of each item
Column 110, Line 38: Item i) replace "Aβ1-42" with --Aβ-1-42--

Claim 6:
Column 111, Line 20: Item a) replace "11-4" with --IL-4--

Signed and Sealed this
Eleventh Day of October, 2022

Katherine Kelly Vidal
*Director of the United States Patent and Trademark Office*

```
                        SEQUENCE LISTING

<160> NUMBER OF SEQ ID NOS: 65

<210> SEQ ID NO 1
<211> LENGTH: 218
<212> TYPE: PRT
<213> ORGANISM: cucumber mosaic virus

<400> SEQUENCE: 1

Met Asp Lys Ser Glu Ser Thr Ser Ala Gly Arg Ser Arg Arg Arg Arg
1               5                   10                  15

Pro Arg Arg Gly Ser Arg Ser Ala Pro Ser Ser Ala Asp Ala Asn Phe
                20                  25                  30

Arg Val Leu Ser Gln Gln Leu Ser Arg Leu Asn Lys Thr Leu Ala Ala
            35                  40                  45

Gly Arg Pro Thr Ile Asn His Pro Thr Phe Val Gly Ser Glu Arg Cys
    50                  55                  60

Lys Pro Gly Tyr Thr Phe Thr Ser Ile Thr Leu Lys Pro Pro Lys Ile
65                  70                  75                  80

Asp Arg Gly Ser Tyr Tyr Gly Lys Arg Leu Leu Leu Pro Asp Ser Val
                85                  90                  95

Thr Glu Tyr Asp Lys Lys Leu Val Ser Arg Ile Gln Ile Arg Val Asn
                100                 105                 110

Pro Leu Pro Lys Phe Asp Ser Thr Val Trp Val Thr Val Arg Lys Val
            115                 120                 125

Pro Ala Ser Ser Asp Leu Ser Val Ala Ala Ile Ser Ala Met Phe Ala
    130                 135                 140

Asp Gly Ala Ser Pro Val Leu Val Tyr Gln Tyr Ala Ala Ser Gly Val
145                 150                 155                 160

Gln Ala Asn Asn Lys Leu Leu Tyr Asp Leu Ser Ala Met Arg Ala Asp
                165                 170                 175

Ile Gly Asp Met Arg Lys Tyr Ala Val Leu Val Tyr Ser Lys Asp Asp
            180                 185                 190

Ala Leu Glu Thr Asp Glu Leu Val Leu His Val Asp Val Glu His Gln
    195                 200                 205

Arg Ile Pro Thr Ser Gly Val Leu Pro Val
    210                 215

<210> SEQ ID NO 2
<211> LENGTH: 217
<212> TYPE: PRT
<213> ORGANISM: cucumber mosaic virus

<400> SEQUENCE: 2

Asp Lys Ser Glu Ser Thr Ser Ala Gly Arg Asn Arg Arg Arg Arg Pro
1               5                   10                  15

Arg Arg Gly Ser Arg Ser Ala Ser Ser Ala Asp Ala Asn Phe Arg
                20                  25                  30

Val Leu Ser Gln Gln Leu Ser Arg Leu Asn Lys Thr Leu Ala Ala Gly
            35                  40                  45

Arg Pro Thr Ile Asn His Pro Thr Phe Val Gly Ser Glu Arg Cys Lys
    50                  55                  60
```

```
Pro Gly Tyr Thr Phe Ser Ser Ile Thr Leu Lys Pro Pro Lys Ile Asp
 65                  70                  75                  80

Arg Gly Ser Tyr Tyr Gly Lys Arg Leu Leu Pro Asp Ser Val Thr
                 85                  90                  95

Glu Phe Asp Lys Lys Leu Val Ser Arg Ile Gln Ile Arg Val Asn Pro
            100                 105                 110

Leu Pro Lys Phe Asp Ser Thr Val Trp Val Thr Val Arg Lys Val Pro
        115                 120                 125

Ala Ser Ser Asp Leu Ser Val Ala Ala Ile Ser Ala Met Phe Ala Asp
    130                 135                 140

Gly Ala Ser Pro Val Leu Val Tyr Gln Tyr Ala Ala Ser Gly Val Gln
145                 150                 155                 160

Ala Asn Asn Lys Leu Leu Tyr Asp Leu Ser Ala Met Arg Ala Asp Ile
                165                 170                 175

Gly Asp Met Arg Lys Tyr Ala Val Leu Val Tyr Ser Lys Asp Asp Ala
            180                 185                 190

Leu Glu Thr Asp Glu Leu Val Leu His Val Asp Ile Glu His Gln Arg
        195                 200                 205

Ile Pro Thr Ser Gly Val Leu Pro Val
    210                 215
```

<210> SEQ ID NO 3
<211> LENGTH: 218
<212> TYPE: PRT
<213> ORGANISM: cucumber mosaic virus

<400> SEQUENCE: 3

```
Met Asp Lys Ser Glu Ser Pro Asn Ala Ser Arg Thr Ser Arg Arg Arg
 1               5                  10                  15

Arg Pro Arg Arg Gly Ser Arg Ser Ala Ser Gly Ala Asp Ala Gly Leu
                 20                  25                  30

Arg Ala Leu Thr Gln Gln Met Leu Lys Leu Asn Lys Thr Leu Ala Ile
             35                  40                  45

Gly Arg Pro Thr Leu Asn His Pro Thr Phe Val Gly Ser Ala Ser Cys
 50                  55                  60

Lys Pro Gly Tyr Thr Phe Thr Ser Ile Thr Leu Lys Pro Pro Glu Ile
 65                  70                  75                  80

Glu Lys Gly Ser Tyr Phe Gly Arg Arg Leu Ser Leu Pro Asp Ser Val
                 85                  90                  95

Thr Asp Tyr Asp Lys Lys Leu Val Ser Arg Ile Gln Ile Arg Ile Asn
            100                 105                 110

Pro Leu Pro Lys Phe Asp Ser Thr Val Trp Val Thr Val Arg Lys Val
        115                 120                 125

Pro Ser Ser Ser Asp Leu Ser Val Ala Thr Ile Ser Ala Met Phe Gly
    130                 135                 140

Asp Gly Asn Ser Pro Val Leu Val Tyr Gln Tyr Thr Ala Ser Gly Val
145                 150                 155                 160

Gln Ala Asn Asn Lys Leu Leu Tyr Asp Leu Ser Glu Met Arg Ala Asp
                165                 170                 175

Ile Gly Asp Met Arg Lys Tyr Ala Val Leu Val Tyr Ser Lys Asp Asp
            180                 185                 190

Lys Leu Glu Glu Asp Glu Ile Val Leu His Val Asp Val Glu His Gln
        195                 200                 205

Arg Ile Pro Ile Ser Arg Met Leu Pro Thr
    210                 215
```

<210> SEQ ID NO 4
<211> LENGTH: 14
<212> TYPE: PRT
<213> ORGANISM: artificial sequence
<220> FEATURE:
<223> OTHER INFORMATION: tetanus toxoid epitope tt830

<400> SEQUENCE: 4

Gln Tyr Ile Lys Ala Asn Ser Lys Phe Ile Gly Ile Thr Glu
1               5                   10

<210> SEQ ID NO 5
<211> LENGTH: 13
<212> TYPE: PRT
<213> ORGANISM: artificial sequence
<220> FEATURE:
<223> OTHER INFORMATION: PADRE

<400> SEQUENCE: 5

Ala Lys Phe Val Ala Ala Trp Thr Leu Lys Ala Ala Ala
1               5                   10

<210> SEQ ID NO 6
<211> LENGTH: 222
<212> TYPE: PRT
<213> ORGANISM: artificial sequence
<220> FEATURE:
<223> OTHER INFORMATION: CMV-Ntt830

<400> SEQUENCE: 6

Met Gly Gln Tyr Ile Lys Ala Asn Ser Lys Phe Ile Gly Ile Thr Glu
1               5                   10                  15

Arg Arg Arg Arg Pro Arg Gly Ser Arg Ser Ala Pro Ser Ser Ala
            20                  25                  30

Asp Ala Asn Phe Arg Val Leu Ser Gln Gln Leu Ser Arg Leu Asn Lys
        35                  40                  45

Thr Leu Ala Ala Gly Arg Pro Thr Ile Asn His Pro Thr Phe Val Gly
    50                  55                  60

Ser Glu Arg Cys Lys Pro Gly Tyr Thr Phe Thr Ser Ile Thr Leu Lys
65                  70                  75                  80

Pro Pro Lys Ile Asp Arg Gly Ser Tyr Tyr Gly Lys Arg Leu Leu Leu
                85                  90                  95

Pro Asp Ser Val Thr Glu Tyr Asp Lys Lys Leu Val Ser Arg Ile Gln
            100                 105                 110

Ile Arg Val Asn Pro Leu Pro Lys Phe Asp Ser Thr Val Trp Val Thr
        115                 120                 125

Val Arg Lys Val Pro Ala Ser Ser Asp Leu Ser Val Ala Ala Ile Ser
    130                 135                 140

Ala Met Phe Ala Asp Gly Ala Ser Pro Val Leu Val Tyr Gln Tyr Ala
145                 150                 155                 160

Ala Ser Gly Val Gln Ala Asn Asn Lys Leu Leu Tyr Asp Leu Ser Ala
                165                 170                 175

Met Arg Ala Asp Ile Gly Asp Met Arg Lys Tyr Ala Val Leu Val Tyr
            180                 185                 190

Ser Lys Asp Asp Ala Leu Glu Thr Asp Glu Leu Val Leu His Val Asp
        195                 200                 205

Val Glu His Gln Arg Ile Pro Thr Ser Gly Val Leu Pro Val
    210                 215                 220

<210> SEQ ID NO 7
<211> LENGTH: 220
<212> TYPE: PRT
<213> ORGANISM: artificial sequence
<220> FEATURE:
<223> OTHER INFORMATION: CMV-Npadr

<400> SEQUENCE: 7

```
Met Ala Lys Phe Val Ala Ala Trp Thr Leu Lys Ala Ala Arg Arg
1               5                   10                  15

Arg Arg Pro Arg Arg Gly Ser Arg Ser Ala Pro Ser Ser Ala Asp Ala
                20                  25                  30

Asn Phe Arg Val Leu Ser Gln Gln Leu Ser Arg Leu Asn Lys Thr Leu
            35                  40                  45

Ala Ala Gly Arg Pro Thr Ile Asn His Pro Thr Phe Val Gly Ser Glu
        50                  55                  60

Arg Cys Lys Pro Gly Tyr Thr Phe Thr Ser Ile Thr Leu Lys Pro Pro
65                  70                  75                  80

Lys Ile Asp Arg Gly Ser Tyr Tyr Gly Lys Arg Leu Leu Leu Pro Asp
                85                  90                  95

Ser Val Thr Glu Tyr Asp Lys Lys Leu Val Ser Arg Ile Gln Ile Arg
            100                 105                 110

Val Asn Pro Leu Pro Lys Phe Asp Ser Thr Val Trp Val Thr Val Arg
        115                 120                 125

Lys Val Pro Ala Ser Ser Asp Leu Ser Val Ala Ala Ile Ser Ala Met
    130                 135                 140

Phe Ala Asp Gly Ala Ser Pro Val Leu Val Tyr Gln Tyr Ala Ala Ser
145                 150                 155                 160

Gly Val Gln Ala Asn Asn Lys Leu Leu Tyr Asp Leu Ser Ala Met Arg
                165                 170                 175

Ala Asp Ile Gly Asp Met Arg Lys Tyr Ala Val Leu Val Tyr Ser Lys
            180                 185                 190

Asp Asp Ala Leu Glu Thr Asp Glu Leu Val Leu His Val Asp Val Glu
        195                 200                 205

His Gln Arg Ile Pro Thr Ser Gly Val Leu Pro Val
    210                 215                 220
```

<210> SEQ ID NO 8
<211> LENGTH: 34
<212> TYPE: DNA
<213> ORGANISM: artificial sequence
<220> FEATURE:
<223> OTHER INFORMATION: primer CMcpF

<400> SEQUENCE: 8
caccatggac aaatctgaat caaccagtgc tggt                          34

<210> SEQ ID NO 9
<211> LENGTH: 37
<212> TYPE: DNA
<213> ORGANISM: artificial sequence
<220> FEATURE:
<223> OTHER INFORMATION: primer CMcpR

<400> SEQUENCE: 9
caaagcttat caaactggga gcaccccaga tgtggga                       37

<210> SEQ ID NO 10
<211> LENGTH: 660

-continued

```
<212> TYPE: DNA
<213> ORGANISM: cucumber mosaic virus

<400> SEQUENCE: 10
atggacaaat ctgaatcaac cagtgctggt cgtagccgtc gacgtcgtcc gcgtcgtggt    60
tcccgctccg cccctcctc cgcggatgct aactttagag tcttgtcgca gcagctttcg    120
cgacttaata agacgttagc agctggtcgt ccaactatta accacccaac ctttgtaggg    180
agtgaacgct gtaaacctgg gtacacgttc acatctatca ccctaaagcc accaaaaata    240
gaccgtgggt cttattatgg taaaaggttg ttattacctg attcagtcac ggaatatgat    300
aagaaacttg tttcgcgcat tcaaattcga gttaatcctt tgccgaaatt tgattcaacc    360
gtgtgggtga cagtccgtaa agttcctgcc tcttcggact tatccgttgc cgccatttct    420
gctatgtttg cggacggagc ctcaccggta ctggtttatc agtacgctgc atctggagtc    480
caagctaaca acaaactgtt gtatgatctt tcggcgatgc gcgctgatat aggcgacatg    540
agaaagtacg ccgtcctcgt gtattcaaaa gacgatgcac tcgagacaga cgagttagta    600
cttcatgttg acgtcgagca ccaacgtatt cccacatctg gggtgctccc agtttgataa    660

<210> SEQ ID NO 11
<211> LENGTH: 20
<212> TYPE: DNA
<213> ORGANISM: artificial sequence
<220> FEATURE:
<223> OTHER INFORMATION: primer pET-220

<400> SEQUENCE: 11
agcaccgccg ccgcaaggaa                                                20

<210> SEQ ID NO 12
<211> LENGTH: 52
<212> TYPE: DNA
<213> ORGANISM: artificial sequence
<220> FEATURE:
<223> OTHER INFORMATION: primer CMV-tt83-1R

<400> SEQUENCE: 12
atttggagtt ggccttaata tactggccca tggtatatct ccttcttaaa gt            52

<210> SEQ ID NO 13
<211> LENGTH: 52
<212> TYPE: DNA
<213> ORGANISM: artificial sequence
<220> FEATURE:
<223> OTHER INFORMATION: primer CMV-tt83Sal-R2

<400> SEQUENCE: 13
gacgtcgacg ctcggtaatc ccgataaatt tggagttggc cttaatatac tg            52

<210> SEQ ID NO 14
<211> LENGTH: 672
<212> TYPE: DNA
<213> ORGANISM: artificial sequence
<220> FEATURE:
<223> OTHER INFORMATION: cDNA coding for CMV-Ntt830

<400> SEQUENCE: 14
atgggccagt atattaaggc caactccaaa tttatcggga ttaccgagcg tcgacgtcgt    60
ccgcgtcgtg gttcccgctc cgcccctcc tccgcggatg ctaactttag agtcttgtcg    120
cagcagcttt cgcgacttaa taagacgtta gcagctggtc gtccaactat taaccaccca    180
```

```
acctttgtag ggagtgaacg ctgtaaacct gggtacacgt tcacatctat caccctaaag      240
ccaccaaaaa tagaccgtgg gtcttattat ggtaaaaggt tgttattacc tgattcagtc      300
acggaatatg ataagaaact tgtttcgcgc attcaaattc gagttaatcc tttgccgaaa      360
tttgattcaa ccgtgtgggt gacagtccgt aaagttcctg cctcttcgga cttatccgtt      420
gccgccattt ctgctatgtt tgcggacgga gcctcaccgg tactggttta tcagtacgct      480
gcatctggag tccaagctaa caacaaactg ttgtatgatc tttcggcgat gcgcgctgat      540
ataggcgaca tgagaaagta cgccgtcctc gtgtattcaa agacgatgc actcgagaca       600 gacgagttag tacttcatgt tgacgtcgag caccaacgta ttcccacatc tggggtgctc      660
ccagtttgat aa                                                          672
```

<210> SEQ ID NO 15
<211> LENGTH: 55
<212> TYPE: DNA
<213> ORGANISM: artificial sequence
<220> FEATURE:
<223> OTHER INFORMATION: primer CMV-padrSal-R

<400> SEQUENCE: 15

```
gacgtcgacg cgcggccgcc ttgagggtcc acgcggccac aaatttcgcc atggt          55
```

<210> SEQ ID NO 16
<211> LENGTH: 666
<212> TYPE: DNA
<213> ORGANISM: artificial sequence
<220> FEATURE:
<223> OTHER INFORMATION: cDNA coding for CMV-Npadr

<400> SEQUENCE: 16

```
atggcgaaat ttgtggccgc gtggaccctc aaggcggccg cgcgtcgacg tcgtccgcgt      60
cgtggttccc gctccgcccc ctcctccgcg gatgctaact ttagagtctt gtcgcagcag     120 cttttcgcgac ttaataagac gttagcagct ggtcgtccaa ctattaacca cccaacctttт    180 gtagggagtg aacgctgtaa acctgggtac acgttcacat ctatcaccct aaagccacca     240
aaaatagacc gtgggtctta ttatggtaaa aggttgttat acctgattc agtcacggaa      300 tatgataaga aacttgtttc gcgcattcaa attcgagtta atccttttgcc gaaatttgat    360 tcaaccgtgt gggtgacagt ccgtaaagtt cctgcctctt cggacttatc cgttgccgcc    420
atttctgcta tgttttgcgga cggagcctca ccggtactgg tttatcagta cgctgcatct    480
ggagtccaag ctaacaacaa actgttgtat gatctttcgg cgatgcgcgc tgatataggc    540
gacatgagaa agtacgccgt cctcgtgtat tcaaaagacg atgcactcga cagacgag      600 ttagtacttc atgttgacgt cgagcaccaa cgtattccca catctggggt gctcccagtt    660
tgataa                                                                666
```

<210> SEQ ID NO 17
<211> LENGTH: 176
<212> TYPE: PRT
<213> ORGANISM: artificial sequence
<220> FEATURE:
<223> OTHER INFORMATION: rFel-2-G3-1

<400> SEQUENCE: 17

```
Val Lys Met Ala Glu Thr Cys Pro Ile Phe Tyr Asp Val Phe Phe Ala
1               5                   10                  15

Val Ala Asn Gly Asn Glu Leu Leu Leu Asp Leu Ser Leu Thr Lys Val
            20                  25                  30
```

```
Asn Ala Thr Glu Pro Glu Arg Thr Ala Met Lys Lys Ile Gln Asp Cys
         35                  40                  45

Tyr Val Glu Asn Gly Leu Ile Ser Arg Val Leu Asp Gly Leu Val Met
 50                  55                  60

Thr Thr Ile Ser Ser Lys Asp Cys Met Gly Glu Ala Val Gln Asn
 65                  70                  75                  80

Thr Val Glu Asp Leu Lys Leu Asn Thr Leu Gly Arg Gly Gly Gly
                 85                  90                  95

Ser Gly Gly Gly Ser Gly Gly Gly Ser Cys Glu Ile Cys Pro
                100                 105                 110

Ala Val Lys Arg Asp Val Asp Leu Phe Leu Thr Gly Thr Pro Asp Glu
         115                 120                 125

Tyr Val Glu Gln Val Ala Gln Tyr Lys Ala Leu Pro Val Val Leu Glu
 130                 135                 140

Asn Ala Arg Ile Leu Lys Asn Cys Val Asp Ala Lys Met Thr Glu Glu
145                 150                 155                 160

Asp Lys Glu Asn Ala Leu Ser Val Leu Asp Lys Ile Tyr Thr Ser Pro
                165                 170                 175
```

<210> SEQ ID NO 18
<211> LENGTH: 176
<212> TYPE: PRT
<213> ORGANISM: artificial sequence
<220> FEATURE:
<223> OTHER INFORMATION: rFel-1-G3-2

<400> SEQUENCE: 18

```
Cys Glu Ile Cys Pro Ala Val Lys Arg Asp Val Asp Leu Phe Leu Thr
 1               5                  10                  15

Gly Thr Pro Asp Glu Tyr Val Glu Gln Val Ala Gln Tyr Lys Ala Leu
             20                  25                  30

Pro Val Val Leu Glu Asn Ala Arg Ile Leu Lys Asn Cys Val Asp Ala
         35                  40                  45

Lys Met Thr Glu Glu Asp Lys Glu Asn Ala Leu Ser Val Leu Asp Lys
 50                  55                  60

Ile Tyr Thr Ser Pro Gly Gly Gly Ser Gly Gly Gly Ser Gly
 65                  70                  75                  80

Gly Gly Gly Ser Val Lys Met Ala Glu Thr Cys Pro Ile Phe Tyr Asp
                 85                  90                  95

Val Phe Phe Ala Val Ala Asn Gly Asn Glu Leu Leu Leu Asp Leu Ser
                100                 105                 110

Leu Thr Lys Val Asn Ala Thr Glu Pro Glu Arg Thr Ala Met Lys Lys
         115                 120                 125

Ile Gln Asp Cys Tyr Val Glu Asn Gly Leu Ile Ser Arg Val Leu Asp
         130                 135                 140

Gly Leu Val Met Thr Thr Ile Ser Ser Lys Asp Cys Met Gly Glu
145                 150                 155                 160

Ala Val Gln Asn Thr Val Glu Asp Leu Lys Leu Asn Thr Leu Gly Arg
                165                 170                 175
```

<210> SEQ ID NO 19
<211> LENGTH: 10
<212> TYPE: PRT
<213> ORGANISM: artificial sequence
<220> FEATURE:
<223> OTHER INFORMATION: alpha-synuclein peptide - GGC

<400> SEQUENCE: 19

Lys Asn Glu Glu Gly Ala Pro Gly Gly Cys
1               5                   10

<210> SEQ ID NO 20
<211> LENGTH: 139
<212> TYPE: PRT
<213> ORGANISM: artificial sequence
<220> FEATURE:
<223> OTHER INFORMATION: murine IL17A protein

<400> SEQUENCE: 20

Ala Ala Ile Ile Pro Gln Ser Ser Ala Cys Pro Asn Thr Glu Ala Lys
1               5                   10                  15

Asp Phe Leu Gln Asn Val Lys Val Asn Leu Lys Val Phe Asn Ser Leu
                20                  25                  30

Gly Ala Lys Val Ser Ser Arg Arg Pro Ser Asp Tyr Leu Asn Arg Ser
            35                  40                  45

Thr Ser Pro Trp Thr Leu His Arg Asn Glu Asp Pro Asp Arg Tyr Pro
        50                  55                  60

Ser Val Ile Trp Glu Ala Gln Cys Arg His Gln Arg Cys Val Asn Ala
65                  70                  75                  80

Glu Gly Lys Leu Asp His His Met Asn Ser Val Leu Ile Gln Gln Glu
                85                  90                  95

Ile Leu Val Leu Lys Arg Glu Pro Glu Ser Cys Pro Phe Thr Phe Arg
            100                 105                 110

Val Glu Lys Met Leu Val Gly Val Gly Cys Thr Cys Val Ala Ser Ile
        115                 120                 125

Val Arg Gln Ala Ala Gly Gly Gly Gly Cys
    130                 135

<210> SEQ ID NO 21
<211> LENGTH: 27
<212> TYPE: PRT
<213> ORGANISM: artificial sequence
<220> FEATURE:
<223> OTHER INFORMATION: aa 2-27 of SEQ ID NO:1

<400> SEQUENCE: 21

Asp Lys Ser Glu Ser Thr Ser Ala Gly Arg Ser Arg Arg Arg Arg Pro
1               5                   10                  15

Arg Arg Gly Ser Arg Ser Ala Pro Ser Ser Ala
                20                  25

<210> SEQ ID NO 22
<211> LENGTH: 11
<212> TYPE: PRT
<213> ORGANISM: artificial sequence
<220> FEATURE:
<223> OTHER INFORMATION: alpha-synuclein petide - GGC

<400> SEQUENCE: 22

Met Asp Val Phe Met Lys Gly Leu Gly Gly Cys
1               5                   10

<210> SEQ ID NO 23
<211> LENGTH: 132
<212> TYPE: PRT
<213> ORGANISM: artificial sequence
<220> FEATURE:
<223> OTHER INFORMATION: m-IL-5

<400> SEQUENCE: 23

```
Met Glu Ile Pro Met Ser Thr Val Val Lys Glu Thr Leu Thr Gln Leu
1               5                   10                  15

Ser Ala His Arg Ala Leu Leu Thr Ser Asn Glu Thr Met Arg Leu Pro
            20                  25                  30

Val Pro Thr His Lys Asn His Gln Leu Cys Ile Gly Glu Ile Phe Gln
                35                  40                  45

Gly Leu Asp Ile Leu Lys Asn Gln Thr Val Arg Gly Gly Thr Val Glu
        50                  55                  60

Met Leu Phe Gln Asn Leu Ser Leu Ile Lys Lys Tyr Ile Asp Arg Gln
65                  70                  75                  80

Lys Glu Lys Cys Gly Glu Glu Arg Arg Arg Thr Arg Gln Phe Leu Asp
                85                  90                  95

Tyr Leu Gln Glu Phe Leu Gly Val Met Ser Thr Glu Trp Ala Met Glu
            100                 105                 110

Gly Leu Glu Pro Lys Ser Thr Pro Pro Gly Ser Ser Gly Gly Ala Pro
        115                 120                 125

Gly Gly Cys Gly
        130
```

<210> SEQ ID NO 24
<211> LENGTH: 24
<212> TYPE: PRT
<213> ORGANISM: artificial sequence
<220> FEATURE:
<223> OTHER INFORMATION: Influenza M2 peptide

<400> SEQUENCE: 24

```
Ser Leu Leu Thr Glu Val Glu Thr Pro Ile Arg Asn Glu Trp Gly Cys
1               5                   10                  15

Arg Cys Asn Asp Ser Ser Asp Gly
            20
```

<210> SEQ ID NO 25
<211> LENGTH: 9
<212> TYPE: PRT
<213> ORGANISM: artificial sequence
<220> FEATURE:
<223> OTHER INFORMATION: Ab1-6-GGC

<400> SEQUENCE: 25

```
Asp Ala Gly Phe Arg His Gly Gly Cys
1               5
```

<210> SEQ ID NO 26
<211> LENGTH: 13
<212> TYPE: PRT
<213> ORGANISM: artificial sequence
<220> FEATURE:
<223> OTHER INFORMATION: HA 307-319

<400> SEQUENCE: 26

```
Pro Lys Tyr Val Lys Gln Asn Thr Leu Lys Leu Ala Thr
1               5                   10
```

<210> SEQ ID NO 27
<211> LENGTH: 20
<212> TYPE: PRT
<213> ORGANISM: artificial sequence
<220> FEATURE:
<223> OTHER INFORMATION: HBVnc 50-69

```
<400> SEQUENCE: 27

Pro His His Thr Ala Leu Arg Gln Ala Ile Leu Cys Trp Gly Glu Leu
1               5                   10                  15

Met Thr Leu Ala
            20

<210> SEQ ID NO 28
<211> LENGTH: 21
<212> TYPE: PRT
<213> ORGANISM: artificial sequence
<220> FEATURE:
<223> OTHER INFORMATION: CS 378-398

<400> SEQUENCE: 28

Asp Ile Glu Lys Lys Ile Ala Lys Met Glu Lys Ala Ser Ser Val Phe
1               5                   10                  15

Asn Val Val Asn Ser
            20

<210> SEQ ID NO 29
<211> LENGTH: 16
<212> TYPE: PRT
<213> ORGANISM: artificial sequence
<220> FEATURE:
<223> OTHER INFORMATION: MT 17-31

<400> SEQUENCE: 29

Tyr Ser Gly Pro Leu Lys Ala Glu Ile Ala Gln Arg Leu Glu Asp Val
1               5                   10                  15

<210> SEQ ID NO 30
<211> LENGTH: 21
<212> TYPE: PRT
<213> ORGANISM: artificial sequence
<220> FEATURE:
<223> OTHER INFORMATION: tt 947-967

<400> SEQUENCE: 30

Phe Asn Asn Phe Thr Val Ser Phe Trp Leu Arg Val Pro Lys Val Ser
1               5                   10                  15

Ala Ser His Leu Glu
            20

<210> SEQ ID NO 31
<211> LENGTH: 10
<212> TYPE: DNA
<213> ORGANISM: artificial sequence
<220> FEATURE:
<223> OTHER INFORMATION: palindromic CpG

<400> SEQUENCE: 31
gacgatcgtc                                                          10

<210> SEQ ID NO 32
<211> LENGTH: 8
<212> TYPE: PRT
<213> ORGANISM: artificial sequence
<220> FEATURE:
<223> OTHER INFORMATION: alpha synuclein peptide

<400> SEQUENCE: 32

Met Asp Val Phe Met Lys Gly Leu
1               5
```

<210> SEQ ID NO 33
<211> LENGTH: 7
<212> TYPE: PRT
<213> ORGANISM: artificial sequence
<220> FEATURE:
<223> OTHER INFORMATION: alpha synuclein peptide

<400> SEQUENCE: 33

Lys Asn Glu Glu Gly Ala Pro
1               5

<210> SEQ ID NO 34
<211> LENGTH: 10
<212> TYPE: PRT
<213> ORGANISM: artificial sequence
<220> FEATURE:
<223> OTHER INFORMATION: aplha synuclein peptide

<400> SEQUENCE: 34

Glu Gly Tyr Gln Asp Tyr Glu Pro Glu Ala
1               5                   10

<210> SEQ ID NO 35
<211> LENGTH: 11
<212> TYPE: PRT
<213> ORGANISM: artificial sequence
<220> FEATURE:
<223> OTHER INFORMATION: HisTag plus linker

<400> SEQUENCE: 35

Leu Glu His His His His His His Gly Gly Cys
1               5                   10

<210> SEQ ID NO 36
<211> LENGTH: 30
<212> TYPE: DNA
<213> ORGANISM: artificial sequence
<220> FEATURE:
<223> OTHER INFORMATION: CpG oligonucleotide

<400> SEQUENCE: 36
gggggggggg gacgatcgtc gggggggggg                                     30

<210> SEQ ID NO 37
<211> LENGTH: 70
<212> TYPE: PRT
<213> ORGANISM: Felis domesticus

<400> SEQUENCE: 37

Glu Ile Cys Pro Ala Val Lys Arg Asp Val Asp Leu Phe Leu Thr Gly
1               5                   10                  15

Thr Pro Asp Glu Tyr Val Glu Gln Val Ala Gln Tyr Lys Ala Leu Pro
            20                  25                  30

Val Val Leu Glu Asn Ala Arg Ile Leu Lys Asn Cys Val Asp Ala Lys
        35                  40                  45

Met Thr Glu Glu Asp Lys Glu Asn Ala Leu Ser Leu Leu Asp Lys Ile
    50                  55                  60

Tyr Thr Ser Pro Leu Cys
65                  70

<210> SEQ ID NO 38
<211> LENGTH: 92
<212> TYPE: PRT
<213> ORGANISM: Felis domesticus

```
<400> SEQUENCE: 38

Val Lys Met Ala Glu Thr Cys Pro Ile Phe Tyr Asp Val Phe Phe Ala
1               5                   10                  15

Val Ala Asn Gly Asn Glu Leu Leu Asp Leu Ser Leu Thr Lys Val
            20                  25                  30

Asn Ala Thr Glu Pro Glu Arg Thr Ala Met Lys Lys Ile Gln Asp Cys
        35                  40                  45

Tyr Val Glu Asn Gly Leu Ile Ser Arg Val Leu Asp Gly Leu Val Met
    50                  55                  60

Thr Thr Ile Ser Ser Ser Lys Asp Cys Met Gly Glu Ala Val Gln Asn
65                  70                  75                  80

Thr Val Glu Asp Leu Lys Leu Asn Thr Leu Gly Arg
                85                  90

<210> SEQ ID NO 39
<211> LENGTH: 90
<212> TYPE: PRT
<213> ORGANISM: Felis domesticus

<400> SEQUENCE: 39

Val Lys Met Ala Glu Thr Cys Pro Ile Phe Tyr Asp Val Phe Phe Ala
1               5                   10                  15

Val Ala Asn Gly Asn Glu Leu Leu Leu Asp Leu Ser Leu Thr Lys Val
            20                  25                  30

Asn Ala Thr Glu Pro Glu Arg Thr Ala Met Lys Lys Ile Gln Asp Cys
        35                  40                  45

Tyr Val Glu Asn Gly Leu Ile Ser Arg Val Leu Asp Gly Leu Val Met
    50                  55                  60

Ile Ala Ile Asn Glu Tyr Cys Met Gly Glu Ala Val Gln Asn Thr Val
65                  70                  75                  80

Glu Asp Leu Lys Leu Asn Thr Leu Gly Arg
                85                  90

<210> SEQ ID NO 40
<211> LENGTH: 78
<212> TYPE: PRT
<213> ORGANISM: Felis domesticus

<400> SEQUENCE: 40

Val Lys Met Ala Glu Thr Cys Pro Ile Phe Tyr Asp Val Phe Phe Ala
1               5                   10                  15

Val Ala Asn Gly Asn Glu Leu Leu Asp Leu Ser Leu Thr Lys Val
            20                  25                  30

Asn Ala Thr Glu Pro Glu Arg Thr Ala Met Lys Lys Ile Gln Asp Cys
        35                  40                  45

Tyr Val Glu Asn Gly Leu Ile Ser Arg Val Leu Asp Gly Leu Val Met
    50                  55                  60

Pro Ser Thr Asn Ile Ala Trp Val Lys Gln Phe Arg Thr Pro
65                  70                  75

<210> SEQ ID NO 41
<211> LENGTH: 115
<212> TYPE: PRT
<213> ORGANISM: Homo sapiens

<400> SEQUENCE: 41

Ile Pro Thr Glu Ile Pro Thr Ser Ala Leu Val Lys Glu Thr Leu Ala
1               5                   10                  15
```

-continued

```
Leu Leu Ser Thr His Arg Thr Leu Leu Ile Ala Asn Glu Thr Leu Arg
         20                  25                  30

Ile Pro Val Pro Val His Lys Asn His Gln Leu Cys Thr Glu Glu Ile
             35                  40                  45

Phe Gln Gly Ile Gly Thr Leu Glu Ser Gln Thr Val Gln Gly Gly Thr
 50                  55                  60

Val Glu Arg Leu Phe Lys Asn Leu Ser Leu Ile Lys Lys Tyr Ile Asp
 65                  70                  75                  80

Gly Gln Lys Lys Lys Cys Gly Glu Arg Arg Val Asn Gln Phe
             85                  90                  95

Leu Asp Tyr Leu Gln Glu Phe Leu Gly Val Met Asn Thr Glu Trp Ile
                100                 105                 110

Ile Glu Ser
        115

<210> SEQ ID NO 42
<211> LENGTH: 132
<212> TYPE: PRT
<213> ORGANISM: Homo sapiens

<400> SEQUENCE: 42

Gly Ile Thr Ile Pro Arg Asn Pro Gly Cys Pro Asn Ser Glu Asp Lys
1               5                   10                  15

Asn Phe Pro Arg Thr Val Met Val Asn Leu Asn Ile His Asn Arg Asn
             20                  25                  30

Thr Asn Thr Asn Pro Lys Arg Ser Ser Asp Tyr Tyr Asn Arg Ser Thr
         35                  40                  45

Ser Pro Trp Asn Leu His Arg Asn Glu Asp Pro Glu Arg Tyr Pro Ser
 50                  55                  60

Val Ile Trp Glu Ala Lys Cys Arg His Leu Gly Cys Ile Asn Ala Asp
 65                  70                  75                  80

Gly Asn Val Asp Tyr His Met Asn Ser Val Pro Ile Gln Gln Glu Ile
             85                  90                  95

Leu Val Leu Arg Arg Glu Pro Pro His Cys Pro Asn Ser Phe Arg Leu
                100                 105                 110

Glu Lys Ile Leu Val Ser Val Gly Cys Thr Cys Val Thr Pro Ile Val
        115                 120                 125

His His Val Ala
        130

<210> SEQ ID NO 43
<211> LENGTH: 141
<212> TYPE: PRT
<213> ORGANISM: Homo sapiens

<400> SEQUENCE: 43

Ser His Thr Leu Pro Val Arg Leu Leu Arg Pro Ser Asp Asp Val Gln
1               5                   10                  15

Lys Ile Val Glu Glu Leu Gln Ser Leu Ser Lys Met Leu Leu Lys Asp
             20                  25                  30

Val Glu Glu Glu Lys Gly Val Leu Val Ser Gln Asn Tyr Thr Leu Pro
         35                  40                  45

Cys Leu Ser Pro Asp Ala Gln Pro Pro Asn Asn Ile His Ser Pro Ala
 50                  55                  60

Ile Arg Ala Tyr Leu Lys Thr Ile Arg Gln Leu Asp Asn Lys Ser Val
 65                  70                  75                  80
```

Ile Asp Glu Ile Ile Glu His Leu Asp Lys Leu Ile Phe Gln Asp Ala
            85                  90                  95

Pro Glu Thr Asn Ile Ser Val Pro Thr Asp Thr His Glu Cys Lys Arg
            100                 105                 110

Phe Ile Leu Thr Ile Ser Gln Gln Phe Ser Gln Cys Met Asp Leu Ala
            115                 120                 125

Leu Lys Ser Leu Thr Ser Gly Ala Gln Gln Ala Thr Thr
            130                 135                 140

<210> SEQ ID NO 44
<211> LENGTH: 136
<212> TYPE: PRT
<213> ORGANISM: artificial sequence
<220> FEATURE:
<223> OTHER INFORMATION: canine IL-31

<400> SEQUENCE: 44

Ser His Met Ala Pro Thr His Gln Leu Pro Pro Ser Asp Val Arg Lys
1               5                   10                  15

Ile Ile Leu Glu Leu Gln Pro Leu Ser Arg Gly Leu Leu Glu Asp Tyr
            20                  25                  30

Gln Lys Lys Glu Thr Gly Val Pro Glu Ser Asn Arg Thr Leu Leu Leu
            35                  40                  45

Cys Leu Thr Ser Asp Ser Gln Pro Pro Arg Leu Asn Ser Ser Ala Ile
50                  55                  60

Leu Pro Tyr Phe Arg Ala Ile Arg Pro Leu Ser Asp Lys Asn Ile Ile
65                  70                  75                  80

Asp Lys Ile Ile Glu Gln Leu Asp Lys Leu Lys Phe Gln His Glu Pro
            85                  90                  95

Glu Thr Glu Ile Ser Val Pro Ala Asp Thr Phe Glu Cys Lys Ser Phe
            100                 105                 110

Ile Leu Thr Ile Leu Gln Gln Phe Ser Ala Cys Leu Glu Ser Val Phe
            115                 120                 125

Lys Ser Leu Asn Ser Gly Pro Gln
            130                 135

<210> SEQ ID NO 45
<211> LENGTH: 129
<212> TYPE: PRT
<213> ORGANISM: Homo sapiens

<400> SEQUENCE: 45

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
            35                  40                  45

Ala Thr Val Leu Arg Gln Phe Tyr Ser His His Glu Lys Asp Thr Arg
50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
            85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser

<210> SEQ ID NO 46
<211> LENGTH: 122
<212> TYPE: PRT
<213> ORGANISM: Homo sapiens

<400> SEQUENCE: 46

Leu Thr Cys Leu Gly Gly Phe Ala Ser Pro Gly Pro Val Pro Pro Ser
1               5                   10                  15

Thr Ala Leu Arg Glu Leu Ile Glu Glu Leu Val Asn Ile Thr Gln Asn
            20                  25                  30

Gln Lys Ala Pro Leu Cys Asn Gly Ser Met Val Trp Ser Ile Asn Leu
        35                  40                  45

Thr Ala Gly Met Tyr Cys Ala Ala Leu Glu Ser Leu Ile Asn Val Ser
    50                  55                  60

Gly Cys Ser Ala Ile Glu Lys Thr Gln Arg Met Leu Ser Gly Phe Cys
65                  70                  75                  80

Pro His Lys Val Ser Ala Gly Gln Phe Ser Ser Leu His Val Arg Asp
                85                  90                  95

Thr Lys Ile Glu Val Ala Gln Phe Val Lys Asp Leu Leu Leu His Leu
            100                 105                 110

Lys Lys Leu Phe Arg Glu Gly Arg Phe Asn
        115                 120

<210> SEQ ID NO 47
<211> LENGTH: 15
<212> TYPE: PRT
<213> ORGANISM: artificial sequence
<220> FEATURE:
<223> OTHER INFORMATION: 15 aa spacer

<400> SEQUENCE: 47

Gly Gly Gly Gly Ser Gly Gly Gly Ser Gly Gly Gly Ser
1               5                   10                  15

<210> SEQ ID NO 48
<211> LENGTH: 9
<212> TYPE: PRT
<213> ORGANISM: artificial sequence
<220> FEATURE:
<223> OTHER INFORMATION: HisTag plus linker

<400> SEQUENCE: 48

His His His His His His Gly Gly Cys
1               5

<210> SEQ ID NO 49
<211> LENGTH: 579
<212> TYPE: DNA
<213> ORGANISM: artificial sequence
<220> FEATURE:
<223> OTHER INFORMATION: F12H6GGC

<400> SEQUENCE: 49
catatggaaa tttgtccggc agttaaacgt gatgttgacc tgtttctgac cggtacaccg      60
gatgaatatg tggaacaggt tgcacagtat aaagcactgc cggttgttct ggaaaatgca     120
cgtattctga aaaattgcgt ggatgccaaa atgaccgaag aggataaaga aaatgccctg     180

-continued

```
agcgttctgg ataaaatcta taccagtccg ctgtgcggtg gtggtggtag tggtggcggt    240
ggttcaggcg gtggcggtag cgttaaaatg gcagaaacct gtccgatctt ttatgatgtt    300
ttttttgccg tggccaatgg caatgaactg ctgctggatc tgagcctgac caaagttaat    360
gcaaccgaac cggaacgtac cgcaatgaaa aaaatccagg attgctatgt ggaaaacggt    420
ctgattagcc gtgttctgga tggtctggtt atgaccacca ttagcagcag caaagattgt    480
atgggtgaag cagtgcagaa taccgttgaa gatctgaaac tgaataccct gggtcgtcat    540
catcatcacc atcatggtgg ttgttaataa ctcgagtaa                           579
```

<210> SEQ ID NO 50
<211> LENGTH: 187
<212> TYPE: PRT
<213> ORGANISM: artificial sequence
<220> FEATURE:
<223> OTHER INFORMATION: F12H6GGC

<400> SEQUENCE: 50

```
Met Glu Ile Cys Pro Ala Val Lys Arg Asp Val Asp Leu Phe Leu Thr
1               5                   10                  15

Gly Thr Pro Asp Glu Tyr Val Glu Gln Val Ala Gln Tyr Lys Ala Leu
            20                  25                  30

Pro Val Val Leu Glu Asn Ala Arg Ile Leu Lys Asn Cys Val Asp Ala
        35                  40                  45

Lys Met Thr Glu Glu Asp Lys Glu Asn Ala Leu Ser Val Leu Asp Lys
    50                  55                  60

Ile Tyr Thr Ser Pro Leu Cys Gly Gly Gly Ser Gly Gly Gly Gly
65                  70                  75                  80

Ser Gly Gly Gly Gly Ser Val Lys Met Ala Glu Thr Cys Pro Ile Phe
                85                  90                  95

Tyr Asp Val Phe Phe Ala Val Ala Asn Gly Asn Glu Leu Leu Leu Asp
            100                 105                 110

Leu Ser Leu Thr Lys Val Asn Ala Thr Glu Pro Glu Arg Thr Ala Met
        115                 120                 125

Lys Lys Ile Gln Asp Cys Tyr Val Glu Asn Gly Leu Ile Ser Arg Val
    130                 135                 140

Leu Asp Gly Leu Val Met Thr Thr Ile Ser Ser Ser Lys Asp Cys Met
145                 150                 155                 160

Gly Glu Ala Val Gln Asn Thr Val Glu Asp Leu Lys Leu Asn Thr Leu
                165                 170                 175

Gly Arg His His His His His His Gly Gly Cys
            180                 185
```

<210> SEQ ID NO 51
<211> LENGTH: 28
<212> TYPE: DNA
<213> ORGANISM: artificial sequence
<220> FEATURE:
<223> OTHER INFORMATION: Primer Fel_BglF

<400> SEQUENCE: 51

```
tgaagatctg aaactgaata ccctgggt                                        28
```

<210> SEQ ID NO 52
<211> LENGTH: 180
<212> TYPE: PRT
<213> ORGANISM: artificial sequence
<220> FEATURE:
<223> OTHER INFORMATION: FELD1-15aa

<400> SEQUENCE: 52

| Met | Val | Lys | Met | Ala | Glu | Thr | Cys | Pro | Ile | Phe | Tyr | Asp | Val | Phe | Phe |
|-----|-----|-----|-----|-----|-----|-----|-----|-----|-----|-----|-----|-----|-----|-----|-----|
| 1 | | | | 5 | | | | | 10 | | | | | 15 | |

Ala Val Ala Asn Gly Asn Glu Leu Leu Leu Asp Leu Ser Leu Thr Lys
            20                25                30

Val Asn Ala Thr Glu Pro Glu Arg Thr Ala Met Lys Lys Ile Gln Asp
            35                40                45

Cys Tyr Val Glu Asn Gly Leu Ile Ser Arg Val Leu Asp Gly Leu Val
   50                     55                60

Met Thr Thr Ile Ser Ser Ser Lys Asp Cys Met Gly Glu Ala Val Gln
65                      70                75              80

Asn Thr Val Glu Asp Leu Lys Leu Asn Thr Leu Gly Arg Gly Gly Gly
            85                90                95

Gly Ser Gly Gly Gly Ser Gly Gly Gly Ser Glu Ile Cys Pro
           100               105             110

Ala Val Lys Arg Asp Val Asp Leu Phe Leu Thr Gly Thr Pro Asp Glu
           115               120             125

Tyr Val Glu Gln Val Ala Gln Tyr Lys Ala Leu Pro Val Val Leu Glu
   130                   135             140

Asn Ala Arg Ile Leu Lys Asn Cys Val Asp Ala Lys Met Thr Glu Glu
145                   150             155          160

Asp Lys Glu Asn Ala Leu Ser Leu Leu Asp Lys Ile Tyr Thr Ser Pro
           165               170             175

Leu Cys Leu Glu
        180

<210> SEQ ID NO 53
<211> LENGTH: 48
<212> TYPE: DNA
<213> ORGANISM: artificial sequence
<220> FEATURE:
<223> OTHER INFORMATION: Reverse Primer Feld-dHR

<400> SEQUENCE: 53
tactcgagtt attaacaacc accacgaccc agggtattca gtttcaga                48

<210> SEQ ID NO 54
<211> LENGTH: 371
<212> TYPE: PRT
<213> ORGANISM: artificial sequence
<220> FEATURE:
<223> OTHER INFORMATION: Amb a1 mature protein

<400> SEQUENCE: 54

Ala Glu Asp Leu Gln Glu Ile Leu Pro Val Asn Glu Thr Arg Arg Leu
1                    5                10                15

Thr Thr Ser Gly Ala Tyr Asn Ile Ile Asp Gly Cys Trp Arg Gly Lys
            20                25                30

Ala Asp Trp Ala Glu Asn Arg Lys Ala Leu Ala Asp Cys Ala Gln Gly
           35                40                45

Phe Gly Lys Gly Thr Val Gly Gly Lys Asp Gly Asp Ile Tyr Thr Val
   50                     55                60

Thr Ser Asp Leu Asp Asp Asp Val Ala Asn Pro Lys Glu Gly Thr Leu
65                      70                75              80

Arg Phe Gly Ala Ala Gln Asn Arg Pro Leu Trp Ile Ile Phe Glu Arg
            85                90                95

```
Asp Met Val Ile Arg Leu Asp Lys Glu Met Val Val Asn Ser Asp Lys
            100                 105                 110

Thr Ile Asp Gly Arg Gly Ala Lys Val Glu Ile Ile Asn Ala Gly Phe
        115                 120                 125

Thr Leu Asn Gly Val Lys Asn Val Ile Ile His Asn Ile Asn Met His
    130                 135                 140

Asp Val Lys Val Asn Pro Gly Gly Leu Ile Lys Ser Asn Asp Gly Pro
145                 150                 155                 160

Ala Ala Pro Arg Ala Gly Ser Asp Gly Asp Ala Ile Ser Ile Ser Gly
                165                 170                 175

Ser Ser Gln Ile Trp Ile Asp His Cys Ser Leu Ser Lys Ser Val Asp
            180                 185                 190

Gly Leu Val Asp Ala Lys Leu Gly Thr Thr Arg Leu Thr Val Ser Asn
        195                 200                 205

Ser Leu Phe Thr Gln His Gln Phe Val Leu Leu Phe Gly Ala Gly Asp
    210                 215                 220

Glu Asn Ile Glu Asp Arg Gly Met Leu Ala Thr Val Ala Phe Asn Thr
225                 230                 235                 240

Phe Thr Asp Asn Val Asp Gln Arg Met Pro Arg Cys Arg His Gly Phe
                245                 250                 255

Phe Gln Val Val Asn Asn Asn Tyr Asp Lys Trp Gly Ser Tyr Ala Ile
            260                 265                 270

Gly Gly Ser Ala Ser Pro Thr Ile Leu Ser Gln Gly Asn Arg Phe Cys
        275                 280                 285

Ala Pro Asp Glu Arg Ser Lys Lys Asn Val Leu Gly Arg His Gly Glu
290                 295                 300

Ala Ala Ala Glu Ser Met Lys Trp Asn Trp Arg Thr Asn Lys Asp Val
305                 310                 315                 320

Leu Glu Asn Gly Ala Ile Phe Val Ala Ser Gly Val Asp Pro Val Leu
                325                 330                 335

Thr Pro Glu Gln Ser Ala Gly Met Ile Pro Ala Glu Pro Gly Glu Ser
            340                 345                 350

Ala Leu Ser Leu Thr Ser Ser Ala Gly Val Leu Ser Cys Gln Pro Gly
        355                 360                 365

Ala Pro Cys
    370

<210> SEQ ID NO 55
<211> LENGTH: 514
<212> TYPE: PRT
<213> ORGANISM: artificial sequence
<220> FEATURE:
<223> OTHER INFORMATION: Cry J2

<400> SEQUENCE: 55

Met Ala Met Lys Phe Ile Ala Pro Met Ala Phe Val Ala Met Gln Leu
1               5                   10                  15

Ile Ile Met Ala Ala Glu Asp Gln Ser Ala Gln Ile Met Leu Asp
                20                  25                  30

Ser Asp Ile Glu Gln Tyr Leu Arg Ser Asn Arg Ser Leu Arg Lys Val
            35                  40                  45

Glu His Ser Arg His Asp Ala Ile Asn Ile Phe Asn Val Glu Lys Tyr
        50                  55                  60

Gly Ala Val Gly Asp Gly Lys His Asp Cys Thr Glu Ala Phe Ser Thr
65                  70                  75                  80
```

```
Ala Trp Gln Ala Ala Cys Lys Lys Pro Ser Ala Met Leu Leu Val Pro
             85                  90                  95

Gly Asn Lys Lys Phe Val Val Asn Asn Leu Phe Phe Asn Gly Pro Cys
        100                 105                 110

Gln Pro His Phe Thr Phe Lys Val Asp Gly Ile Ile Ala Ala Tyr Gln
        115                 120                 125

Asn Pro Ala Ser Trp Lys Asn Asn Arg Ile Trp Leu Gln Phe Ala Lys
        130                 135                 140

Leu Thr Gly Phe Thr Leu Met Gly Lys Gly Val Ile Asp Gly Gln Gly
145                 150                 155                 160

Lys Gln Trp Trp Ala Gly Gln Cys Lys Trp Val Asn Gly Arg Glu Ile
                165                 170                 175

Cys Asn Asp Arg Asp Arg Pro Thr Ala Ile Lys Phe Asp Phe Ser Thr
            180                 185                 190

Gly Leu Ile Ile Gln Gly Leu Lys Leu Met Asn Ser Pro Glu Phe His
        195                 200                 205

Leu Val Phe Gly Asn Cys Glu Gly Val Lys Ile Gly Ile Ser Ile
        210                 215                 220

Thr Ala Pro Arg Asp Ser Pro Asn Thr Asp Gly Ile Asp Ile Phe Ala
225                 230                 235                 240

Ser Lys Asn Phe His Leu Gln Lys Asn Thr Ile Gly Thr Gly Asp Asp
                245                 250                 255

Cys Val Ala Ile Gly Thr Gly Ser Ser Asn Ile Val Ile Glu Asp Leu
            260                 265                 270

Ile Cys Gly Pro Gly His Gly Ile Ser Ile Gly Ser Leu Gly Arg Glu
        275                 280                 285

Asn Ser Arg Ala Glu Val Ser Tyr Val His Val Asn Gly Ala Lys Phe
        290                 295                 300

Ile Asp Thr Gln Asn Gly Leu Arg Ile Lys Thr Trp Gln Gly Gly Ser
305                 310                 315                 320

Gly Met Ala Ser His Ile Ile Tyr Glu Asn Val Glu Met Ile Asn Ser
                325                 330                 335

Glu Asn Pro Ile Leu Ile Asn Gln Phe Tyr Cys Thr Ser Ala Ser Ala
            340                 345                 350

Cys Gln Asn Gln Arg Ser Ala Val Gln Ile Gln Asp Val Thr Tyr Lys
        355                 360                 365

Asn Ile Arg Gly Thr Ser Ala Thr Ala Ala Ile Gln Leu Lys Cys
        370                 375                 380

Ser Asp Ser Met Pro Cys Lys Asn Ile Asn Leu Ser Asp Ile Ser Leu
385                 390                 395                 400

Lys Leu Thr Ser Gly Lys Ile Ala Ser Cys Leu Asn Asp Asn Ala Asn
                405                 410                 415

Gly Tyr Phe Ser Gly His Val Ile Pro Ala Cys Lys Asn Leu Ser Pro
            420                 425                 430

Ser Ala Lys Arg Lys Glu Ser Lys Ser His Lys Pro Lys Thr Val
        435                 440                 445

Met Val Glu Asn Met Gly Ala Tyr Asp Lys Gly Asn Arg Thr Arg Ile
        450                 455                 460

Leu Leu Gly Ser Arg Pro Asn Cys Thr Asn Lys Cys His Gly Cys
465                 470                 475                 480

Ser Pro Cys Lys Ala Lys Leu Val Ile Val His Arg Ile Met Pro Gln
                485                 490                 495

Glu Tyr Tyr Pro Gln Arg Trp Met Cys Ser Cys His Gly Lys Ile Tyr
```

```
                500           505           510
His Pro
```

<210> SEQ ID NO 56
<211> LENGTH: 181
<212> TYPE: PRT
<213> ORGANISM: artificial sequence
<220> FEATURE:
<223> OTHER INFORMATION: F12GGC

<400> SEQUENCE: 56

```
Met Glu Ile Cys Pro Ala Val Lys Arg Asp Val Asp Leu Phe Leu Thr
1               5                   10                  15

Gly Thr Pro Asp Glu Tyr Val Glu Gln Val Ala Gln Tyr Lys Ala Leu
            20                  25                  30

Pro Val Val Leu Glu Asn Ala Arg Ile Leu Lys Asn Cys Val Asp Ala
        35                  40                  45

Lys Met Thr Glu Glu Asp Lys Glu Asn Ala Leu Ser Val Leu Asp Lys
50                  55                  60

Ile Tyr Thr Ser Pro Leu Cys Gly Gly Gly Ser Gly Gly Gly Gly
65                  70                  75                  80

Ser Gly Gly Gly Gly Ser Val Lys Met Ala Glu Thr Cys Pro Ile Phe
                85                  90                  95

Tyr Asp Val Phe Phe Ala Val Ala Asn Gly Asn Glu Leu Leu Leu Asp
            100                 105                 110

Leu Ser Leu Thr Lys Val Asn Ala Thr Glu Pro Glu Arg Thr Ala Met
        115                 120                 125

Lys Lys Ile Gln Asp Cys Tyr Val Glu Asn Gly Leu Ile Ser Arg Val
130                 135                 140

Leu Asp Gly Leu Val Met Thr Thr Ile Ser Ser Ser Lys Asp Cys Met
145                 150                 155                 160

Gly Glu Ala Val Gln Asn Thr Val Glu Asp Leu Lys Leu Asn Thr Leu
                165                 170                 175

Gly Arg Gly Gly Cys
            180
```

<210> SEQ ID NO 57
<211> LENGTH: 144
<212> TYPE: PRT
<213> ORGANISM: artificial sequence
<220> FEATURE:
<223> OTHER INFORMATION: Ara h6

<400> SEQUENCE: 57

```
Ala Lys Ser Thr Ile Leu Val Ala Leu Leu Ala Leu Val Leu Val Ala
1               5                   10                  15

His Ala Ser Ala Met Arg Arg Glu Arg Gly Arg Gln Gly Asp Ser Ser
            20                  25                  30

Ser Cys Glu Arg Gln Val Asp Arg Val Asn Leu Lys Pro Cys Glu Gln
        35                  40                  45

His Ile Met Gln Arg Ile Met Gly Glu Gln Glu Gln Tyr Asp Ser Tyr
    50                  55                  60

Asp Ile Arg Ser Thr Arg Ser Ser Asp Gln Gln Gln Arg Cys Cys Asp
65                  70                  75                  80

Glu Leu Asn Glu Met Glu Asn Thr Gln Arg Cys Met Cys Glu Ala Leu
                85                  90                  95

Gln Gln Ile Met Glu Asn Gln Cys Asp Arg Leu Gln Asp Arg Gln Met
```

```
                100             105               110
Val Gln Gln Phe Lys Arg Glu Leu Met Asn Leu Pro Gln Gln Cys Asn
        115                 120                 125

Phe Arg Ala Pro Gln Arg Cys Asp Leu Asp Val Ser Gly Gly Arg Cys
        130                 135                 140
```

<210> SEQ ID NO 58
<211> LENGTH: 4
<212> TYPE: PRT
<213> ORGANISM: artificial sequence
<220> FEATURE:
<223> OTHER INFORMATION: linker sequence

<400> SEQUENCE: 58

```
Gly Gly Cys Gly
1
```

<210> SEQ ID NO 59
<211> LENGTH: 178
<212> TYPE: PRT
<213> ORGANISM: artificial sequence
<220> FEATURE:
<223> OTHER INFORMATION: F12

<400> SEQUENCE: 59

```
Met Glu Ile Cys Pro Ala Val Lys Arg Asp Val Asp Leu Phe Leu Thr
1               5                   10                  15

Gly Thr Pro Asp Glu Tyr Val Glu Gln Val Ala Gln Tyr Lys Ala Leu
            20                  25                  30

Pro Val Val Leu Glu Asn Ala Arg Ile Leu Lys Asn Cys Val Asp Ala
        35                  40                  45

Lys Met Thr Glu Glu Asp Lys Glu Asn Ala Leu Ser Val Leu Asp Lys
    50                  55                  60

Ile Tyr Thr Ser Pro Leu Cys Gly Gly Gly Ser Gly Gly Gly Gly
65                  70                  75                  80

Ser Gly Gly Gly Gly Ser Val Lys Met Ala Glu Thr Cys Pro Ile Phe
                85                  90                  95

Tyr Asp Val Phe Phe Ala Val Ala Asn Gly Asn Glu Leu Leu Leu Asp
            100                 105                 110

Leu Ser Leu Thr Lys Val Asn Ala Thr Glu Pro Glu Arg Thr Ala Met
        115                 120                 125

Lys Lys Ile Gln Asp Cys Tyr Val Glu Asn Gly Leu Ile Ser Arg Val
    130                 135                 140

Leu Asp Gly Leu Val Met Thr Thr Ile Ser Ser Lys Asp Cys Met
145                 150                 155                 160

Gly Glu Ala Val Gln Asn Thr Val Glu Asp Leu Lys Leu Asn Thr Leu
                165                 170                 175

Gly Arg
```

<210> SEQ ID NO 60
<211> LENGTH: 153
<212> TYPE: PRT
<213> ORGANISM: Homo sapiens

<400> SEQUENCE: 60

```
Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
            20                  25                  30
```

```
Gly Gln Asp Met Glu Gln Val Val Phe Ser Met Ser Phe Val Gln
            35                  40                  45

Gly Glu Glu Ser Asn Asp Lys Ile Pro Val Ala Leu Gly Leu Lys Glu
 50                  55                  60

Lys Asn Leu Tyr Leu Ser Cys Val Leu Lys Asp Asp Lys Pro Thr Leu
 65                  70                  75                  80

Gln Leu Glu Ser Val Asp Pro Lys Asn Tyr Pro Lys Lys Met Glu
            85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
            115                 120                 125

Asn Met Pro Val Phe Leu Gly Gly Thr Lys Gly Gly Gln Asp Ile Thr
 130                 135                 140

Asp Phe Thr Met Gln Phe Val Ser Ser
 145                 150

<210> SEQ ID NO 61
<211> LENGTH: 114
<212> TYPE: PRT
<213> ORGANISM: artificial sequence
<220> FEATURE:
<223> OTHER INFORMATION: cIL-5 mature protein

<400> SEQUENCE: 61

Ala Val Glu Asn Pro Met Asn Arg Leu Val Ala Glu Thr Leu Thr Leu
 1               5                  10                  15

Leu Ser Thr His Arg Thr Trp Leu Ile Gly Asp Gly Asn Leu Met Ile
            20                  25                  30

Pro Thr Pro Glu Asn Lys Asn His Gln Leu Cys Ile Lys Glu Val Phe
            35                  40                  45

Gln Gly Ile Asp Thr Leu Lys Asn Gln Thr Ala His Gly Glu Ala Val
 50                  55                  60

Asp Lys Leu Phe Gln Asn Leu Ser Leu Ile Lys Glu His Ile Glu Arg
 65                  70                  75                  80

Gln Lys Lys Arg Cys Ala Gly Glu Arg Trp Arg Val Thr Lys Phe Leu
            85                  90                  95

Asp Tyr Leu Gln Val Phe Leu Gly Val Ile Asn Thr Glu Trp Thr Pro
            100                 105                 110

Glu Ser

<210> SEQ ID NO 62
<211> LENGTH: 109
<212> TYPE: PRT
<213> ORGANISM: artificial sequence
<220> FEATURE:
<223> OTHER INFORMATION: cIL-4 mature protein

<400> SEQUENCE: 62

Gly His Asn Phe Asn Ile Thr Ile Lys Glu Ile Ile Lys Met Leu Asn
 1               5                  10                  15

Ile Leu Thr Ala Arg Asn Asp Ser Cys Met Glu Leu Thr Val Lys Asp
            20                  25                  30

Val Phe Thr Ala Pro Lys Asn Thr Ser Asp Lys Glu Ile Phe Cys Arg
            35                  40                  45

Ala Ala Thr Val Leu Arg Gln Ile Tyr Thr His Asn Cys Ser Asn Arg
 50                  55                  60
```

```
Tyr Leu Arg Gly Leu Tyr Arg Asn Leu Ser Ser Met Ala Asn Lys Thr
 65                  70                  75                  80

Cys Ser Met Asn Glu Ile Lys Lys Ser Thr Leu Lys Asp Phe Leu Glu
                 85                  90                  95

Arg Leu Lys Val Ile Met Gln Lys Lys Tyr Tyr Arg His
            100                 105

<210> SEQ ID NO 63
<211> LENGTH: 113
<212> TYPE: PRT
<213> ORGANISM: artificial sequence
<220> FEATURE:
<223> OTHER INFORMATION: cIL-13 mature protein

<400> SEQUENCE: 63

Ser Pro Ser Pro Val Thr Pro Ser Pro Thr Leu Lys Glu Leu Ile Glu
  1               5                  10                  15

Glu Leu Val Asn Ile Thr Gln Asn Gln Ala Ser Leu Cys Asn Gly Ser
                 20                  25                  30

Met Val Trp Ser Val Asn Leu Thr Ala Gly Met Tyr Cys Ala Ala Leu
             35                  40                  45

Glu Ser Leu Ile Asn Val Ser Asp Cys Ser Ala Ile Gln Arg Thr Gln
 50                  55                  60

Arg Met Leu Lys Ala Leu Cys Ser Gln Lys Pro Ala Ala Gly Gln Ile
 65                  70                  75                  80

Ser Ser Glu Arg Ser Arg Asp Thr Lys Ile Glu Val Ile Gln Leu Val
                 85                  90                  95

Lys Asn Leu Leu Thr Tyr Val Arg Gly Val Tyr Arg His Gly Asn Phe
            100                 105                 110

Arg

<210> SEQ ID NO 64
<211> LENGTH: 601
<212> TYPE: PRT
<213> ORGANISM: artificial sequence
<220> FEATURE:
<223> OTHER INFORMATION: Ara h1 mature protein

<400> SEQUENCE: 64

Lys Ser Ser Pro Tyr Gln Lys Lys Thr Glu Asn Pro Cys Ala Gln Arg
  1               5                  10                  15

Cys Leu Gln Ser Cys Gln Gln Glu Pro Asp Asp Leu Lys Gln Lys Ala
                 20                  25                  30

Cys Glu Ser Arg Cys Thr Lys Leu Glu Tyr Asp Pro Arg Cys Val Tyr
             35                  40                  45

Asp Pro Arg Gly His Thr Gly Thr Thr Asn Gln Arg Ser Pro Pro Gly
 50                  55                  60

Glu Arg Thr Arg Gly Arg Gln Pro Gly Asp Tyr Asp Asp Asp Arg Arg
 65                  70                  75                  80

Gln Pro Arg Arg Glu Glu Gly Gly Arg Trp Gly Pro Ala Gly Pro Arg
                 85                  90                  95

Glu Arg Glu Arg Glu Glu Asp Trp Arg Gln Pro Arg Glu Asp Trp Arg
            100                 105                 110

Arg Pro Ser His Gln Gln Pro Arg Lys Ile Arg Pro Glu Gly Arg Glu
            115                 120                 125

Gly Glu Gln Glu Trp Gly Thr Pro Gly Ser His Val Arg Glu Glu Thr
130                 135                 140
```

```
Ser Arg Asn Asn Pro Phe Tyr Phe Pro Ser Arg Arg Phe Ser Thr Arg
145                 150                 155                 160

Tyr Gly Asn Gln Asn Gly Arg Ile Arg Val Leu Gln Arg Phe Asp Gln
                165                 170                 175

Arg Ser Arg Gln Phe Gln Asn Leu Gln Asn His Arg Ile Val Gln Ile
            180                 185                 190

Glu Ala Lys Pro Asn Thr Leu Val Leu Pro Lys His Ala Asp Ala Asp
        195                 200                 205

Asn Ile Leu Val Ile Gln Gln Gly Gln Ala Thr Val Thr Val Ala Asn
    210                 215                 220

Gly Asn Asn Arg Lys Ser Phe Asn Leu Asp Glu Gly His Ala Leu Arg
225                 230                 235                 240

Ile Pro Ser Gly Phe Ile Ser Tyr Ile Leu Asn Arg His Asp Asn Gln
                245                 250                 255

Asn Leu Arg Val Ala Lys Ile Ser Met Pro Val Asn Thr Pro Gly Gln
            260                 265                 270

Phe Glu Asp Phe Phe Pro Ala Ser Ser Arg Asp Gln Ser Ser Tyr Leu
        275                 280                 285

Gln Gly Phe Ser Arg Asn Thr Leu Glu Ala Ala Phe Asn Ala Glu Phe
    290                 295                 300

Asn Glu Ile Arg Arg Val Leu Leu Glu Glu Asn Ala Gly Gly Glu Gln
305                 310                 315                 320

Glu Glu Arg Gly Gln Arg Arg Trp Ser Thr Arg Ser Ser Glu Asn Asn
                325                 330                 335

Glu Gly Val Ile Val Lys Val Ser Lys Glu His Val Glu Glu Leu Thr
            340                 345                 350

Lys His Ala Lys Ser Val Ser Lys Lys Gly Ser Glu Glu Glu Gly Asp
        355                 360                 365

Ile Thr Asn Pro Ile Asn Leu Arg Glu Gly Glu Pro Asp Leu Ser Asn
    370                 375                 380

Asn Phe Gly Lys Leu Phe Glu Val Lys Pro Asp Lys Lys Asn Pro Gln
385                 390                 395                 400

Leu Gln Asp Leu Asp Met Met Leu Thr Cys Val Glu Ile Lys Glu Gly
                405                 410                 415

Ala Leu Met Leu Pro His Phe Asn Ser Lys Ala Met Val Ile Val Val
            420                 425                 430

Val Asn Lys Gly Thr Gly Asn Leu Glu Leu Val Ala Val Arg Lys Glu
        435                 440                 445

Gln Gln Gln Arg Gly Arg Arg Glu Glu Glu Glu Asp Glu Glu
    450                 455                 460

Glu Glu Gly Ser Asn Arg Glu Val Arg Arg Tyr Thr Ala Arg Leu Lys
465                 470                 475                 480

Glu Gly Asp Val Phe Ile Met Pro Ala Ala His Pro Val Ala Ile Asn
                485                 490                 495

Ala Ser Ser Glu Leu His Leu Leu Gly Phe Gly Ile Asn Ala Glu Asn
            500                 505                 510

Asn His Arg Ile Phe Leu Ala Gly Asp Lys Asp Asn Val Ile Asp Gln
        515                 520                 525

Ile Glu Lys Gln Ala Lys Asp Leu Ala Phe Pro Gly Ser Gly Glu Gln
    530                 535                 540

Val Glu Lys Leu Ile Lys Asn Gln Lys Glu Ser His Phe Val Ser Ala
545                 550                 555                 560
```

```
Arg Pro Gln Ser Gln Ser Gln Ser Pro Ser Ser Pro Glu Lys Glu Ser
                565                 570                 575

Pro Glu Lys Glu Asp Gln Glu Glu Glu Asn Gln Gly Gly Lys Gly Pro
            580                 585                 590

Leu Leu Ser Ile Leu Lys Ala Phe Asn
        595                 600

<210> SEQ ID NO 65
<211> LENGTH: 511
<212> TYPE: PRT
<213> ORGANISM: artificial sequence
<220> FEATURE:
<223> OTHER INFORMATION: Ara h3

<400> SEQUENCE: 65

Met Ala Lys Leu Leu Ala Leu Ser Leu Cys Phe Cys Val Leu Val Leu
1               5                   10                  15

Gly Ala Ser Ser Val Thr Phe Arg Gln Gly Gly Glu Glu Asn Glu Cys
                20                  25                  30

Gln Phe Gln Arg Leu Asn Ala Gln Arg Pro Asp Asn Arg Ile Glu Ser
            35                  40                  45

Glu Gly Gly Tyr Ile Glu Thr Trp Asn Pro Asn Asn Gln Glu Phe Gln
    50                  55                  60

Cys Ala Gly Val Ala Leu Ser Arg Thr Val Leu Arg Arg Asn Ala Leu
65                  70                  75                  80

Arg Arg Pro Phe Tyr Ser Asn Ala Pro Leu Glu Ile Tyr Val Gln Gln
                85                  90                  95

Gly Ser Gly Tyr Phe Gly Leu Ile Phe Pro Gly Cys Pro Ser Thr Tyr
            100                 105                 110

Glu Glu Pro Ala Gln Glu Gly Arg Arg Tyr Gln Ser Gln Lys Pro Ser
    115                 120                 125

Arg Arg Phe Gln Val Gly Gln Asp Asp Pro Ser Gln Gln Gln Gln Asp
130                 135                 140

Ser His Gln Lys Val His Arg Phe Asp Glu Gly Asp Leu Ile Ala Val
145                 150                 155                 160

Pro Thr Gly Val Ala Phe Trp Met Tyr Asn Asp Glu Asp Thr Asp Val
                165                 170                 175

Val Thr Val Thr Leu Ser Asp Thr Ser Ser Ile His Asn Gln Leu Asp
            180                 185                 190

Gln Phe Pro Arg Arg Phe Tyr Leu Ala Gly Asn Gln Glu Gln Glu Phe
    195                 200                 205

Leu Arg Tyr Gln Gln Gln Gly Ser Arg Pro His Tyr Arg Gln Ile
210                 215                 220

Ser Pro Arg Val Arg Gly Asp Glu Gln Glu Asn Glu Gly Ser Asn Ile
225                 230                 235                 240

Phe Ser Gly Phe Ala Gln Glu Phe Leu Gln His Ala Phe Gln Val Asp
                245                 250                 255

Arg Gln Thr Val Glu Asn Leu Arg Gly Glu Asn Glu Arg Glu Glu Gln
            260                 265                 270

Gly Ala Ile Val Thr Val Lys Gly Gly Leu Arg Ile Leu Ser Pro Asp
    275                 280                 285

Glu Glu Asp Glu Ser Ser Arg Ser Pro Pro Asn Arg Arg Glu Glu Phe
    290                 295                 300

Asp Glu Asp Arg Ser Arg Pro Gln Gln Arg Gly Lys Tyr Asp Glu Asn
305                 310                 315                 320
```

-continued

```
Arg Arg Gly Tyr Lys Asn Gly Ile Glu Glu Thr Ile Cys Ser Ala Ser
                325                 330                 335

Val Lys Lys Asn Leu Gly Arg Ser Ser Asn Pro Asp Ile Asn Pro Gln
            340                 345                 350

Ala Gly Ser Leu Arg Ser Val Asn Glu Leu Asp Leu Pro Ile Leu Gly
            355                 360                 365

Trp Leu Gly Leu Ser Ala Gln His Gly Thr Ile Tyr Arg Asn Ala Met
    370                 375                 380

Phe Val Pro His Tyr Thr Leu Asn Ala His Thr Ile Val Val Ala Leu
385                 390                 395                 400

Asn Gly Arg Ala His Val Gln Val Val Asp Ser Asn Gly Asn Arg Val
                405                 410                 415

Tyr Asp Glu Glu Leu Gln Glu Gly His Val Leu Val Val Pro Gln Asn
                420                 425                 430

Phe Ala Val Ala Ala Lys Ala Gln Ser Glu Asn Tyr Glu Tyr Leu Ala
            435                 440                 445

Phe Lys Thr Asp Ser Arg Pro Ser Ile Ala Asn Gln Ala Gly Glu Asn
    450                 455                 460

Ser Ile Ile Asp Asn Leu Pro Glu Val Val Ala Asn Ser Tyr Arg
465                 470                 475                 480

Leu Pro Arg Glu Gln Ala Arg Gln Leu Lys Asn Asn Asn Pro Phe Lys
                485                 490                 495

Phe Phe Val Pro Pro Phe Asp His Gln Ser Met Arg Glu Val Ala
                500                 505                 510
```